US008469893B2

(12) United States Patent
Chiang et al.

(10) Patent No.: US 8,469,893 B2
(45) Date of Patent: Jun. 25, 2013

(54) PORTABLE ULTRASOUND IMAGING SYSTEM

(75) Inventors: Alice Chiang, Weston, MA (US); Steven R. Broadstone, Woburn, MA (US)

(73) Assignee: Teratech Corp., Burlington, MA (US)

( * ) Notice: Subject to any disclaimer, the term of this patent is extended or adjusted under 35 U.S.C. 154(b) by 1026 days.

(21) Appl. No.: 12/008,098

(22) Filed: Jan. 8, 2008

(65) Prior Publication Data

US 2008/0300490 A1   Dec. 4, 2008

Related U.S. Application Data

(60) Division of application No. 09/619,123, filed on Jul. 19, 2000, now Pat. No. 7,500,952, which is a continuation-in-part of application No. 09/123,991, filed on Jul. 28, 1998, now Pat. No. 6,106,472, which is a continuation of application No. 08/971,938, filed on Nov. 17, 1997, now Pat. No. 5,957,846, which is a continuation of application No. PCT/US96/11166, filed on Jun. 28, 1996, now Pat. No. 5,964,709, which is a continuation-in-part of application No. 08/599,816, filed on Feb. 12, 1996, now Pat. No. 5,690,114, which is a continuation-in-part of application No. 08/496,804, filed on Jun. 29, 1995, now Pat. No. 5,590,658.

(51) Int. Cl.
*A61B 8/14* (2006.01)

(52) U.S. Cl.
USPC ............... 600/459; 600/407; 600/437

(58) Field of Classification Search
USPC ............... 600/459, 437, 440, 441, 444, 446, 600/447, 453, 457; 348/77, 163, 198, 442, 348/572, 726
See application file for complete search history.

(56) References Cited

U.S. PATENT DOCUMENTS

| 3,626,417 | A | 12/1971 | Gilbert |
| 3,742,947 | A | 7/1973 | Hashem |
| 3,964,296 | A | 6/1976 | Matzuk |
| 3,965,296 | A | 6/1976 | Miller |
| 4,058,003 | A | 11/1977 | Macovski |
| 4,080,838 | A | 3/1978 | Kuroda et al. |
| 4,110,835 | A | 8/1978 | Dubil et al. |
| 4,127,034 | A | 11/1978 | Lederman et al. |

(Continued)

FOREIGN PATENT DOCUMENTS

| DE | 42 41 712 | 6/1993 |
| DE | 43 02 538 | 4/1994 |

(Continued)

OTHER PUBLICATIONS

Mustafa Karaman; "A VLSI Receive Beamformer for Digital Ultrasound Imaging"; IEEE; (1992); V-657-V-660.

(Continued)

*Primary Examiner* — Unsu Jung
*Assistant Examiner* — Daniel Huntley
(74) *Attorney, Agent, or Firm* — McCarter & English, LLP

(57) ABSTRACT

A portable ultrasound imaging system includes a scan head coupled by a cable to a portable battery-powered data processor and display unit. The scan head enclosure houses an array of ultrasonic transducers and the circuitry associated therewith, including pulse synchronizer circuitry used in the transmit mode for transmission of ultrasonic pulses and beam forming circuitry used in the receive mode to dynamically focus reflected ultrasonic signals returning from the region of interest being imaged.

47 Claims, 36 Drawing Sheets

U.S. PATENT DOCUMENTS

| | | | |
|---|---|---|---|
| 4,140,022 A | 2/1979 | Maslak | |
| 4,152,678 A | 5/1979 | Shott et al. | |
| 4,154,113 A | 5/1979 | Engeler | |
| 4,170,766 A | 10/1979 | Pridham et al. | |
| 4,173,007 A | 10/1979 | McKeighen et al. | |
| 4,180,790 A | 12/1979 | Thomas | |
| 4,208,916 A | 6/1980 | Thomenius et al. | |
| 4,213,195 A | 7/1980 | Pridham | |
| 4,227,417 A | 10/1980 | Glenn | |
| 4,267,584 A | 5/1981 | McKeighen et al. | |
| 4,280,203 A | 7/1981 | Gilmour | |
| 4,288,764 A | 9/1981 | Ong | |
| 4,386,528 A | 6/1983 | Engle | |
| 4,386,529 A | 6/1983 | Engle | |
| 4,387,597 A | 6/1983 | Brandestini | |
| 4,401,957 A | 8/1983 | McKeighen et al. | |
| 4,413,629 A | 11/1983 | Durley, III | |
| 4,458,324 A | 7/1984 | Burke et al. | |
| 4,464,726 A | 8/1984 | Chiang | |
| 4,471,785 A | 9/1984 | Wilson et al. | |
| 4,512,350 A | 4/1985 | Cimilluca | |
| 4,542,653 A | 9/1985 | Liu | |
| 4,561,019 A | 12/1985 | Lizzi et al. | |
| 4,561,308 A | 12/1985 | Bele | |
| 4,598,589 A | 7/1986 | Riley et al. | |
| 4,632,124 A | 12/1986 | Hiller et al. | |
| 4,663,973 A | 5/1987 | Iida | |
| 4,699,009 A | 10/1987 | Maslak et al. | |
| 4,707,813 A | 11/1987 | Moeller et al. | |
| 4,787,392 A | 11/1988 | Saugeon | |
| 4,809,184 A | 2/1989 | O'Donnell et al. | |
| 4,811,740 A | 3/1989 | Ikeda et al. | |
| 5,030,953 A | 7/1991 | Chiang | |
| 5,063,541 A | 11/1991 | Kondo et al. | |
| 5,089,983 A | 2/1992 | Chiang | |
| 5,092,337 A | 3/1992 | Uchiumi et al. | |
| 5,119,342 A | 6/1992 | Harrison, Jr. et al. | |
| 5,121,361 A | 6/1992 | Harrison, Jr. et al. | |
| 5,123,415 A | 6/1992 | Daigle | |
| 5,126,962 A | 6/1992 | Chiang | |
| 5,127,409 A | 7/1992 | Daigle | |
| 5,129,399 A | 7/1992 | Hirama | |
| 5,142,649 A | 8/1992 | O'Donnell | |
| 5,143,075 A | 9/1992 | Ishizuka | |
| 5,156,152 A | 10/1992 | Yamazaki et al. | |
| 5,163,434 A | 11/1992 | Kumazawa | |
| 5,173,837 A | 12/1992 | Blackwell et al. | |
| 5,184,623 A | 2/1993 | Mallart | |
| 5,197,477 A | 3/1993 | Peterson et al. | |
| 5,199,437 A | 4/1993 | Langberg | |
| 5,203,335 A | 4/1993 | Noujaim et al. | |
| 5,229,933 A | 7/1993 | Larson, III | |
| 5,230,340 A | 7/1993 | Rhyne | |
| 5,235,982 A | 8/1993 | O'Donnell | |
| 5,235,983 A | 8/1993 | Iida et al. | |
| 5,249,578 A | 10/1993 | Karp et al. | |
| 5,257,629 A | 11/1993 | Kitney et al. | |
| 5,269,307 A | 12/1993 | Fife et al. | |
| 5,287,753 A | 2/1994 | Routh et al. | |
| 5,293,351 A | 3/1994 | Noponen | |
| 5,295,485 A | 3/1994 | Shinomura et al. | |
| 5,322,068 A | 6/1994 | Thiele et al. | |
| 5,343,864 A | 9/1994 | Sugiyama | |
| 5,345,426 A | 9/1994 | Lipschutz | |
| 5,345,939 A | 9/1994 | Engeler et al. | |
| 5,357,962 A | 10/1994 | Green | |
| 5,360,005 A | 11/1994 | Wilk | |
| 5,365,929 A | 11/1994 | Peterson | |
| 5,368,037 A | 11/1994 | Eberle et al. | |
| 5,369,624 A | 11/1994 | Fukukita et al. | |
| 5,373,317 A | 12/1994 | Salvati et al. | |
| 5,381,795 A | 1/1995 | Nordgren et al. | |
| 5,386,830 A | 2/1995 | Powers et al. | |
| 5,388,079 A | 2/1995 | Kim et al. | |
| 5,390,674 A | 2/1995 | Robinson et al. | |
| 5,394,875 A | 3/1995 | Lewis et al. | |
| 5,396,285 A | 3/1995 | Hedberg et al. | |
| 5,402,793 A | 4/1995 | Gruner et al. | |
| 5,413,105 A | 5/1995 | Forestieri | |
| 5,414,803 A | 5/1995 | Malzbender | |
| 5,417,217 A | 5/1995 | Morita et al. | |
| 5,419,330 A | 5/1995 | Nishigaki et al. | |
| 5,423,086 A | 6/1995 | Cannon et al. | |
| 5,435,313 A | 7/1995 | Noda et al. | |
| 5,437,281 A | 8/1995 | Lin et al. | |
| 5,438,994 A | 8/1995 | Starosta et al. | |
| 5,450,851 A | 9/1995 | Hancock | |
| 5,456,257 A | 10/1995 | Johnson et al. | |
| 5,460,180 A | 10/1995 | Klepper et al. | |
| 5,462,057 A | 10/1995 | Hunt et al. | |
| 5,465,011 A | 11/1995 | Miller et al. | |
| 5,465,720 A | 11/1995 | Kurzynski et al. | |
| 5,483,963 A | 1/1996 | Butler et al. | |
| 5,515,341 A | 5/1996 | Toda et al. | |
| 5,517,994 A | 5/1996 | Burke et al. | |
| 5,520,187 A | 5/1996 | Snyder | |
| 5,522,391 A | 6/1996 | Beaudin et al. | |
| 5,528,302 A | 6/1996 | Basoglu et al. | |
| 5,538,004 A | 7/1996 | Bamber | |
| 5,544,128 A | 8/1996 | Kim et al. | |
| 5,544,654 A | 8/1996 | Murphy et al. | |
| 5,546,807 A | 8/1996 | Oxaal et al. | |
| 5,549,111 A | 8/1996 | Wright et al. | |
| 5,551,433 A | 9/1996 | Wright et al. | |
| 5,551,434 A | 9/1996 | Iinuma | |
| 5,555,534 A | 9/1996 | Maslak et al. | |
| 5,588,435 A | 12/1996 | Weng et al. | |
| 5,590,658 A | 1/1997 | Chiang et al. | |
| 5,603,323 A | 2/1997 | Pflugrath et al. | |
| 5,617,864 A | 4/1997 | Stouffer et al. | |
| 5,623,930 A | 4/1997 | Wright et al. | |
| 5,628,321 A | 5/1997 | Scheib et al. | |
| 5,634,465 A | 6/1997 | Schmiesing et al. | |
| 5,640,960 A | 6/1997 | Jones et al. | |
| 5,642,732 A | 7/1997 | Wang | |
| 5,655,535 A | 8/1997 | Friemel et al. | |
| 5,655,536 A | 8/1997 | Takamizawa | |
| 5,690,114 A | 11/1997 | Chiang et al. | |
| 5,697,372 A | 12/1997 | Hughes | |
| 5,709,209 A | 1/1998 | Friemel et al. | |
| 5,722,412 A | 3/1998 | Pflugrath et al. | |
| 5,724,974 A | 3/1998 | Goodsell, Jr. et al. | |
| 5,732,705 A | 3/1998 | Yokoyama et al. | |
| 5,763,785 A | 6/1998 | Chiang | |
| 5,782,769 A | 7/1998 | Hwang et al. | |
| 5,785,655 A | 7/1998 | Goodsell, Jr. et al. | |
| 5,795,297 A | 8/1998 | Daigle | |
| 5,817,024 A | 10/1998 | Ogle et al. | |
| 5,839,442 A | 11/1998 | Chiang et al. | |
| 5,893,363 A | 4/1999 | Little et al. | |
| 5,921,932 A | 7/1999 | Wright et al. | |
| 5,957,846 A | 9/1999 | Chiang et al. | |
| 5,964,709 A | 10/1999 | Chiang et al. | |
| 6,106,472 A | 8/2000 | Chiang et al. | |
| 6,135,961 A | 10/2000 | Pflugrath et al. | |
| 6,416,475 B1 | 7/2002 | Hwang et al. | |
| 7,500,952 B1 | 3/2009 | Chiang et al. | |
| 8,241,217 B2 | 8/2012 | Chiang et al. | |
| 2008/0294046 A1 | 11/2008 | Chiang et al. | |
| 2009/0112091 A1 | 4/2009 | Chiang et al. | |

FOREIGN PATENT DOCUMENTS

| | | |
|---|---|---|
| EP | 0430450 A2 | 6/1991 |
| EP | 0 585 070 | 3/1994 |
| EP | 0 627 635 | 12/1994 |
| EP | 1 016 875 | 5/2000 |
| GB | 2 219 089 | 11/1989 |
| JP | 55-158706 | 11/1980 |
| JP | 55151952 A | 11/1980 |
| JP | 57-175352 | 10/1982 |
| JP | 62227326 A | 10/1987 |
| JP | 63-309246 | 12/1988 |
| JP | 3-206986 | 9/1991 |
| JP | 3234246 A | 10/1991 |
| JP | 4-314437 | 11/1992 |
| JP | 5-103397 | 4/1993 |
| JP | 05228141 A | 9/1993 |

| JP | 7051270 A | 2/1995 |
| JP | 7079981 A | 3/1995 |
| JP | 07116163 A | 5/1995 |
| JP | 7124160 A | 5/1995 |
| JP | 7222744 A | 8/1995 |
| JP | 8038473 A | 2/1996 |
| JP | 8112279 A | 5/1996 |
| JP | 8117227 A | 5/1996 |
| JP | 8505556 | 6/1996 |
| JP | 8173431 A | 7/1996 |
| JP | 8224237 A | 9/1996 |
| WO | WO-9624053 A1 | 8/1996 |

OTHER PUBLICATIONS

O'Donnell, M.; "Real-Time Phased Array Imaging Using Digital Beam Forming and Autonomous Channel Control"; IEEE Ultrasonic Symposium; (1990); 1499-1502.

Hatfield, J.V.; "Transmit and Receive ASICs for an Ultrasound Imaging Multi-Element Array Transducer"; The Institution of Electrical Engineers; (1994); Jun. 1-Jun. 5; IEE Savoy Place, London.

Schwarz, et al.; "Experience rounding with a hand-held two-dimensional cardiac ultrasound device"; The American Journal of Cardiology; (1988); 157-159.

Smith, et al.; "Two-dimensional arrays for medical ultrasound"; Ultrasonic Imaging 14; (1992); 213-233.

Roelandt, et al.; "The ultrasound cardioscope: A hand-held scanner for real-time cardiac imaging"; Clin. Ultrasound; (1980); 8(3): 221-225.

Shattuck, et al.; "Explososcan: A parallel processing technique for high speed ultrasound imaging with linear phrased arrays"; J. Acoust. Soc. Am.; (1984); 75(4).

Von Ramm, et al.; "High-speed ultrasound volumetric imaging system—Part II: Parallel processing and image display"; IEEE Transactions on ultrasonics, ferroelectrics and frequency control; (1991); 38(2).

Sasaki, K., et al.; "A 7-ns 140 mW 1-Mb CMOS SRAM with Current Sense Amplifer"; IEEE Journal of Solid State Circuits; (1992); 27(11): 1511-1518.

Scales, N.R., et al.; "A programmable Multi-Channel CMOS Pulser Chip to Drive Ultrasonic array Transducers"; IEEE Journal of Solid State Circuits; (1994); 29(8): 992-994.

Kerr, S., et al. "Session VI: Integrated signal-Processing Subsystems: A Mixed Analog-Digital Chip for a Phased-Array Signal Processor"; (1988); IEEE International Solid-State Circuits Conference, Feb. 17-19, 1988, Digest of Technical Papers, pp. 58-59 & 296.

O'Donnell, M. "Applications of VLSI Circuits to Medial Imaging"; Proceedings of the IEEE; (1988); 76(9): 1106-1114.

Karaman, M. and O'Donnell, M.; "Synthetic Aperture Imaging for Small Scale systems"; IEEE Transactions on Ultrasonics, Ferroelectrics and Frequency Control; (1995); 42(3): 429-442.

Minivisor Service Manual; Organon Teknika (Sep. 1979).

Daft, C.M.W. and Engeler, W.E.; "Windowing of Wide-Band Ultrasound Transducers"; IEEE Ultrasonic Symposium; (1996); 1541-1544.

ARPA/ONR Medical Ultrasonic Imaging Technology Workshop, Presentation Abstracts, Office of Naval Research, Lansdown, Virginia, Jan. 24-26, 1995.

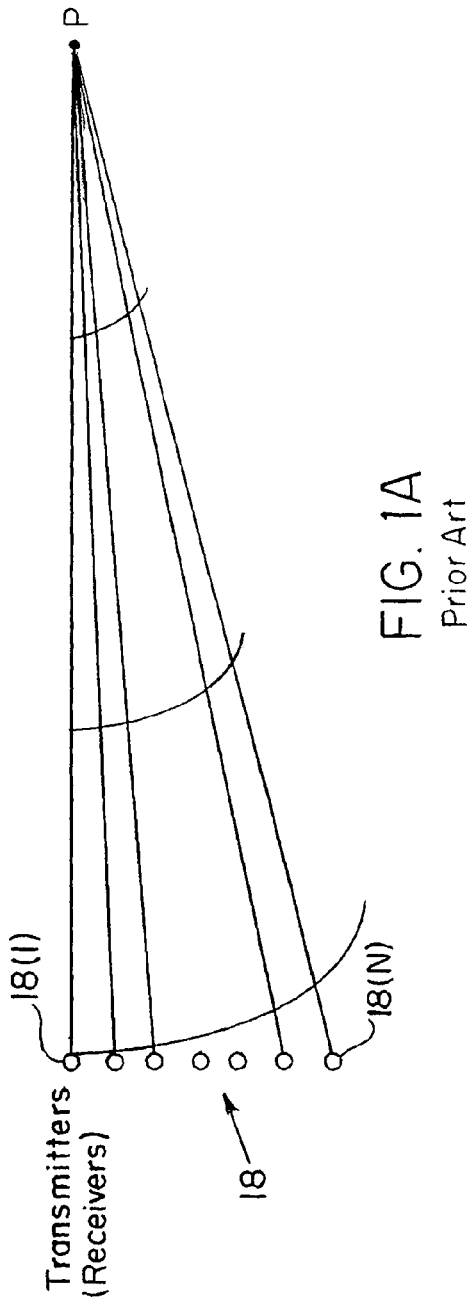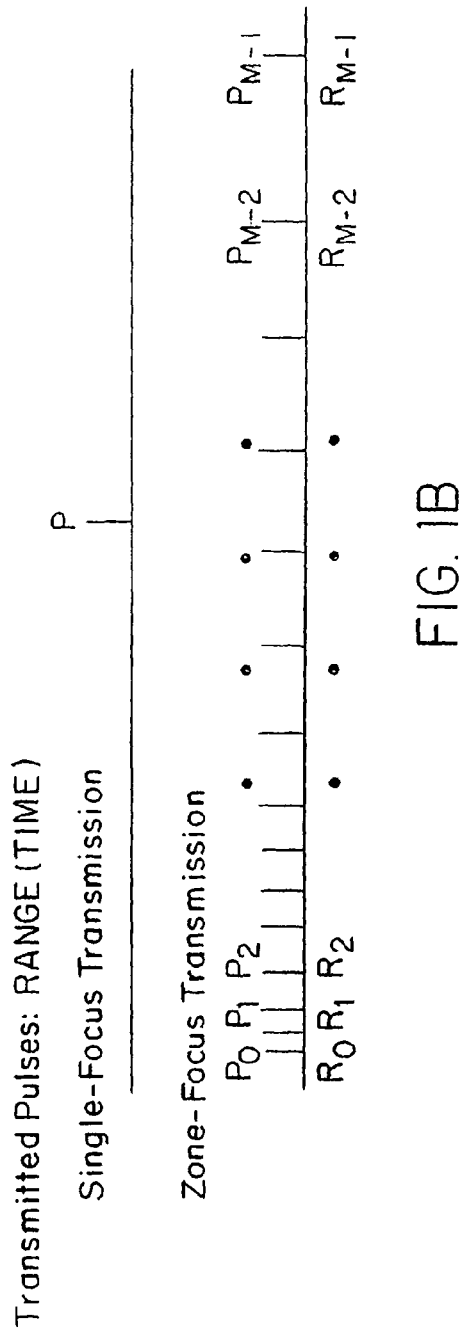
FIG. 1A
Prior Art
FIG. 1B
Prior Art (A) Optical System (B) Time Delay Focus (C) Phase Focus

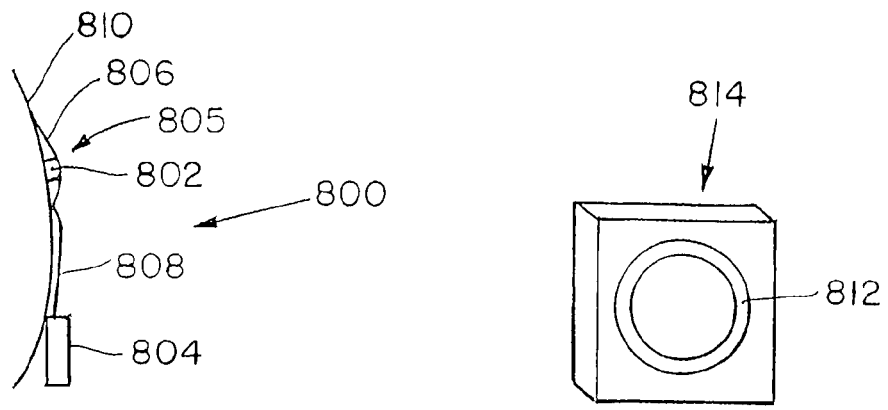
FIG. 39A
FIG. 39B
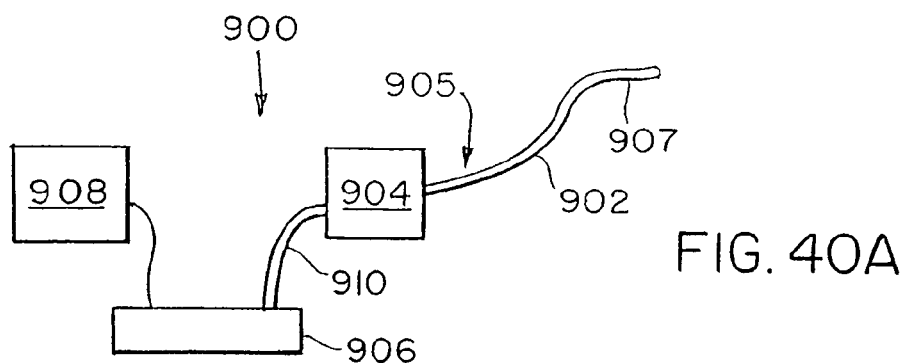
FIG. 40A
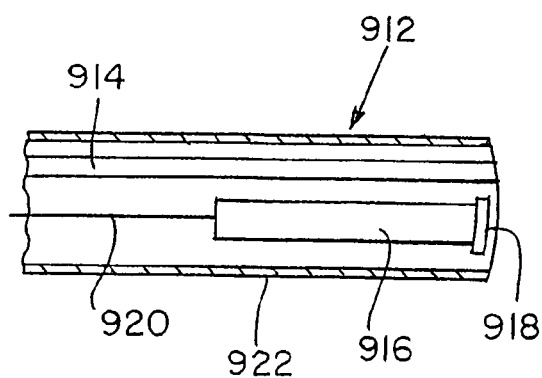
FIG. 40B

PORTABLE ULTRASOUND IMAGING SYSTEM

CROSS REFERENCE TO RELATED APPLICATIONS

This application is a divisional of U.S. application Ser. No. 09/619,123 filed Jul. 19, 2000, now U.S. Pat. No. 7,500,952, which is a continuation-in-part of U.S. application Ser. No. 09/123,991 filed Jul. 28, 1998, now U.S. Pat. No. 6,106,472, which is a continuation of U.S. application Ser. No. 08/971,938 filed Nov. 17, 1997, now U.S. Pat. No. 5,957,846, which is a continuation of PCT/US96/11166 filed Jun. 28, 1996, now U.S. Pat. No. 5,964,709, which is a continuation-in-part of U.S. application Ser. No. 08/599,816 filed Feb. 12, 1996, now U.S. Pat. No. 5,690,114, which is a continuation-in-part of U.S. application No. 08/496,804 filed Jun. 29, 1995, now U.S. Pat. No. 5,590,658. The entire content of the above applications are being incorporated herein by reference.

BACKGROUND OF THE INVENTION

Typical conventional ultrasound systems can have transducer arrays which consist of 128 ultrasonic transducers. Each of the transducers is associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beam forming circuits of the processing circuitry introduce the appropriate delay into each low-level electrical signal from the transducers to dynamically focus the signals such that an accurate image can subsequently be generated.

A schematic block diagram of an imaging array 18 of N piezoelectric ultrasonic transducers 18(1)-18(N) as used in an ultrasound imaging system is shown in FIG. 1A. The array of piezoelectric transducer elements 18(1)-18(N) generate acoustic pulses which propagate into the image target (typically a region of human tissue) or transmitting media with a narrow beam. The pulses propagate as a spherical wave with a constant velocity. Acoustic echoes in the form of returning signals from image points P or reflectors are detected by the same array 18 of transducer elements or another receiving array and can be displayed in a fashion to indicate the location of the reflecting structure P.

The acoustic echo from the point P in the transmitting media reaches each transducer element 18(1)-18(N) of the receiving array after various propagation times. The propagation time for each transducer element is different and depends on the distance between each transducer element and the point P. This holds true for typical ultrasound transmitting media, i.e. soft bodily tissue, where the velocity of sound is assumed (or relatively) constant. Thereafter, the received information is displayed in a manner to indicate the location of the reflecting structure.

In two-dimensional B-mode scanning, the pulses can be transmitted along a number of lines-of-sight as shown in FIG. 1A. If the echoes are sampled and their amplitudes are coded as brightness, a grey scale image can be displayed on a CRT. An image typically contains 128 such scanned lines at 0.75° angular spacing, forming a 900 sector image. Since the velocity of sound in water is $1.54 \times 10^5$ cm/sec, the round-trip time to a depth of 16 cm will be 208/µs. Thus, the total time required to acquire data along 128 lines of sight (for one image) is 26.6 ms. If other signal processors in the system are fast enough to keep up with this data acquisition rate, two-dimensional images can be produced at rates corresponding to standard television video. For example, if the ultrasound imager is used to view reflected or back scattered sound waves through the chest wall between a pair of ribs, the heart pumping can be imaged in real time.

The ultrasonic transmitter is typically a linear array of piezoelectric transducers 18(1)-18(N) (typically spaced half-wavelength apart) for steered arrays whose elevation pattern is fixed and whose azimuth pattern is controlled primarily by delay steering. The radiating (azimuth) beam pattern of a conventional array is controlled primarily by applying delayed transmitting pulses to each transducer element 18(1)-18(N) in such a manner that the energy from all the transmitters summed together at the image point P produce a desired beam shape. Therefore, a time delay circuit is needed in association with each transducer element 18(1)-18(N) for producing the desired transmitted radiation pattern along the predetermined direction.

For a given azimuth angle, as can be seen in FIG. 1B, there can be two different transmitting patterns: a "single-focus" and a "zone-focus" pattern. The single-focus method employs a single pulse focused at mid-range of the image line along a particular line of sight. In a single pulse mode, the azimuth focus depth can be electronically varied, but remains constant for any predetermined direction. In zone-focus operation, multiple pulses, each focused at a different depth (zone), are transmitted along each line of sight or direction. For multiple pulse operation, the array of transmitters is focused at M focal zones along each scan direction, i.e., a series of M pulses is generated $P_0, P_1, \ldots, P_{M-1}$, each pulse being focused at its corresponding range $R_0, R_1, \ldots, R_{M-1}$, respectively.

The pulses are generated in a repeated sequence so that, after start up, every Mth pulse either begins a look down a new direction or corresponds to the initial pulse $P_o$ to repeat the series of looks down the present direction. For the zone-focused mode, a programmable time-delay circuit is needed in association with each transducer element to produce beam patterns focused at different focal zones.

As previously described, the same array 18 of transducer elements 18(1)-18(N) can be used for receiving the return signals. The reflected or echoed beam energy waveform originating at the image point reaches each transducer element after a time delay equal to the distance from the image point to the transducer element divided by the assumed constant speed of the waveform of signals in the media. Similar to the transmitting mode, this time delay is different for each transducer element. At each receiving transducer element, these differences in path length should be compensated for by focusing the reflected energy at each receiver from the particular image point for any given depth. The delay at each receiving element is a function of the distance measured from the element to the center of the array and the viewing angular direction measured normal to the array. It should be noted that in ultrasound, acoustic pulses generated by each transducer are not wideband signals and should be represented in terms of both magnitude and phase.

The beam forming and focusing operations involve forming a sum of the scattered waveforms as observed by all the transducers, but in this sum, the waveforms must be differentially delayed so that they will all arrive in phase and in amplitude in the summation. Hence, a beam forming circuit is required which can apply a different delay on each channel, and vary that delay with time. Along a given direction, as echoes return from deeper tissue, the receiving array varies its focus continually with depth. This process is known as dynamic focusing.

FIGS. 2A-2C show schematic block diagrams of three different conventional imaging or beam focusing techniques. A non-programmable physical lens acoustic system 50 using an acoustic lens 51 is shown in FIG. 2A. In turn, dynamic focusing systems where associated signal processing electronics are employed to perform real-time time delay and phase delay focusing functions are respectively shown in FIGS. 2B and 2C. FIG. 2B shows a time delay system 52 using time delay elements 53, and FIG. 2C shows a phase delay system 54 using phase delay elements 55.

In the lensless systems of FIGS. 2B and 2C, the signal processing elements 53, 55 are needed in association with each receiving transducer element, thus defining processing channels, to provide time delay and focus incident energy from a field point to form an image. Accordingly, a beam forming circuit is required which can provide a different delay on each processing channel, and to further vary that delay with time. Along a predetermined direction, as echoes return from distances further away from the array of transducer elements, the receiving array varies its focus continually with depth to perform dynamic focusing.

After the received beam is formed, it is digitized in a conventional manner. The digital representation of each received pulse is a time sequence corresponding to a scattering cross section of ultrasonic energy returning from a field point as a function of range at the azimuth formed by the beam. Successive pulses are pointed in different directions, covering a field of view from −45° to +45°. In some systems, time averaging of data from successive observations of the same point (referred to as persistence weighting) is used to improve image quality.

For example, in an ultrasound imaging system operating at a 2-5 MHz frequency range, an electronic circuit capable of providing up to 10 to 20 j·1s delay with sub-microsecond time resolution is needed for the desired exact path compensation. As shown in FIG. 2B, a delay line is inherently matched to the time-delay function needed for dynamic focusing in a lensless ultrasound system.

More specifically, in an exemplary ultrasound imaging system with a 5 MHz operating frequency and an array of 128 transducer elements on half-wavelength centers, a straightforward delay implementation requires each processing channel/transducer element to include either a 480-stage delay line with a clock period programmable with a 25 ns resolution or a 480-stage tapped delay line clocked at 40 MHz in conjunction with a programmable 480-to-one time-select switch to set the appropriate delay. There are two problems associated with these conventional techniques. First, a simple variable-speed clock generator has not been developed to date. Secondly, for an N-stage tapped delay line, the area associated with the tap select circuit is proportional to $N^2$, thus such a circuit would require a large amount of microchip area to realize an integrated tap architecture.

Due to the difficulty and complexity associated with the generation of the control circuits of the conventional approach, only a few time-delay structures could be integrated on one microchip, and therefore a large number of chips would be needed to perform a multi-element dynamic beam forming function. For these reasons, none of the prior art ultrasound imaging systems utilize the straightforward time-delay implementation. Instead, a plane-wave mixer approximation is used. In this approximation process, the total delay is separated into two parts: an analog plane-wave mixer technique is used to approximate the required fine delay time and a true coarsely spaced delay line is used to achieve the coarse delay time.

In accordance with the plane-wave approximation, the fine delay can be achieved by modifying the phase of AC waves received by each receiving processing channel and implemented by heterodyning the received waves from each receiving transducer element with different phases of a local oscillator, i.e., creating analog phase shifting at each processing channel. Specifically, by selecting a local oscillator with a proper phase angle of the form $\cos(\omega_o t + \Omega_n(t))$, where $\Omega_n$ is chosen to satisfy the expression $\Omega_n(t) = \omega_o(T'_n(t) - T_n(t))$, $T_n(t)$ is the ideal compensating delay and $T'_n(t)$ is a coarsely quantized approximation of $T_n$. It will be appreciated that when the mixer output is delayed by $T'_n$ the phase of one of its intermediate frequency (IF) sidebands provides phase coherence among all the processing channels.

In the conventional implementation of the aforementioned technique, a tap select is used which connects any received down-conversion mixer output to any tap on a coarsely spaced, serially connected delay line. The tap select is essentially a multiposition switch that connects its input to one of a number of output leads. One output lead is provided for each tap on the delay line. Therefore, each mixer output can be connected to a few coarsely spaced taps on a delay line, and all the tap outputs can be summed together coherently. However, for an exemplary 5 MHz operation, if a single mixer arrangement as described above is used, a delay line with delay resolution less than one microsecond is needed.

In summary, the conventional technique described heretofore involves heterodyning the received signals with an oscillator output by selecting a local oscillator frequency so as to down convert the output to an IF frequency. This down converted signal is then applied to another mixer. By selecting the proper phase angle of the second oscillator, the phase of the intermediate frequency waves produced by the second heterodyning is controlled. The output of the second mixer is then connected through a tap select to only one, or at most a few, coarsely spaced taps on a delay line during the focal scanning along each direction.

The aforementioned approximation technique is used due to the fact that given an image that is somewhat out of focus, the image can be focused in an economically feasible manner by utilizing readily available techniques such as analog mixers and RC networks. Unfortunately, the mixer approximation method suffers from image misregistration errors as well as signal loss relative to the ideally-focused (perfect delay) case.

Modem ultrasound systems require extensive complex signal processing circuitry in order to function. For example, hundreds of delay-and-sum circuits are needed for dynamic beam forming. Also, pulsed or continuous Doppler processors are needed for providing two-dimensional depth and Doppler information in color flow images, and adaptive filters are needed for clutter cancellation. Each of these applications requires more than 10,000 MOPS (million operations per second) to be implemented. Even state-of-the-art CMOS chips only offer several hundred MOPS per chip, and each chip requires a few watts of electric power. Thus, an ultrasound machine with a conventional implementation requires hundreds of chips and dissipates hundreds of watts of power. As a result, conventional systems are implemented in the standard large rack-mounted cabinets.

Another drawback in conventional ultrasound systems is that the cable connecting the scan head to the processing and display unit is required to be extremely sophisticated and, hence, expensive. Since all the beam forming circuitry is located in the console, all of the low-level electrical signals from the ultrasonic transducers must be coupled from the scan head to the processing circuitry. Because the signals are of such a low level, they are extremely susceptible to noise, crosstalk and loss. With a typical transducer array of 128 transducers, the cable between the scan head and the processing and display console is required to contain 128 low-noise, low-crosstalk and low-loss coaxial cables. Such a cable requires expensive materials and extensive assembly time and is therefore very expensive.

SUMMARY OF THE INVENTION

The present invention is directed to a portable ultrasound imaging system and method. The imaging system of the invention includes a hand-held scan head coupled to portable processing circuitry by a cable. The scan head includes a housing which houses the array of ultrasonic transducers which transmit the ultrasonic signals into the region of interest being imaged and which receive reflected ultrasonic signals from the region of interest and which convert the received ultrasonic signals into electrical signals. The housing of the scan head also contains the beam forming circuitry used in the imaging system of the invention to combine the electrical signals from the ultrasonic transducers into an electronic representation of the region of interest. The electronic representation of the region of interest is forwarded over an interface via the system cable to data processing and display circuitry which uses the representation to generate an image of the region of interest.

In one embodiment, the portable processing circuitry is implemented in the form of a lap-top computer which can include an integrated keyboard, a PCMCIA standard modem card for transferring image data and a flip-top flat panel display, such as an active matrix LCD. The lap-top computer, and, therefore the entire system, can be powered by a small lightweight battery. The entire system, including scan head, cable and computer is therefore very lightweight and portable. The total weight of the system preferably does not exceed ten pounds. The interior of the scan head can also include a Faraday shield to shield the electronics of the scan head from interference from extraneous RF sources.

In one embodiment, the system also includes an interface unit between the scan head and the lap-top computer. Instead of being connected directly to the computer, the system cable is connected to the interface unit. Another cable couples the interface unit to the computer. The interface unit performs control and signal/data processing functions not performed by the computer. This reduces the overall processing load on the computer.

In another embodiment, higher quality images are displayed on a cathode ray tube (CRT) display. In that embodiment, signals from the scan head are transferred over the cable to a processor such as a personal computer or lap-top which is in turn interfaced to the CRT display. Signals received from the scan head are received by the processor, which processes the signals and generates appropriate display signals and forwards them to the CRT.

To allow implementation of the functions of the ultrasound imaging system of the invention in the scan head, much of the signal processing circuitry associated with the ultrasonic transducers is integrated on small CMOS chips. For example, the beam forming circuitry used to introduce individual delays into the received ultrasonic signals can be implemented on a single chip for a 64-element array. Thus, two chips are used for 128-element systems. The pulse synchronizing circuitry used to generate transducer driving pulses can also be implemented on a chip. In addition, high voltage driver circuits used in the transmit mode to drive the transducers and preamplifying circuits and gain control circuits used in a receive mode to condition the electrical signals from the transducers can also be integrated on single chips. Also, control circuits such as multiplexer circuits for selecting signals from the transducers and other such control circuits can be formed on single chips.

In one preferred embodiment of the invention, the signal processing circuitry in the scan head is implemented in low-power, high-speed CMOS technology. The integrated circuitry can also be adapted to be operated at lower voltages than conventional circuitry. As a result, the power dissipated in the integrated circuitry and, consequently, the thermal effects caused thereby, are substantially lower than those of conventional circuits. In one embodiment, the total power dissipated in the scan head is less than two watts. This allows the temperature of the scan head to be maintained below 41° C. With such low power dissipation and temperature, the circuits can be implemented in the relatively small volume of the scan head housing without suffering any degradation in performance due to thermal effects. The patient being examined also suffers no harmful thermal effects. Also, because the system requires comparatively little power, it can be powered by a battery located in the data processor and display unit.

As discussed above, in ultrasound systems, individual delays are typically introduced into each individual transmitted ultrasonic pulse and into each signal from each transducer indicative of received reflected ultrasonic energy. These individual delays are used to ensure that the image of the region of interest is properly focused.

The form or pattern of delays introduced into each transducer element are affected by the shape of the array and the desired region scan pattern. For example, in phased arrays, different individual beam steering delays are introduced into each pulse and/or each returning signal for every scan line to produce a properly focused image of a curved region.

Linear and curve linear arrays are typically flat or curved. The arrays can be used to perform linear scanning in which a uniform pattern of delays is introduced to all the transducers. The delays are the same for each scan line. Curved arrays have different delay patterns for each scan line. The present invention is also capable of performing trapezoidal region scans.

In one embodiment, a linear array is used in a sub-aperture scanning process. For example, in this embodiment, the transducer array can include 192 adjacent transducers arranged in a line. During the sub-aperture scanning, only a small portion of the transducers, e.g., 64, are used to generate and receive signals. The transducers at opposite ends of the linear array are used to perform the phased-array scanning process to produce a curved image region at opposite ends of the overall trapezoidal-shaped scan region. Since the phased-array approach is used at the ends of the array, different delay patterns must be introduced for each individual scan line. Between the phased array portions, linear scanning is used. Consequently, during the linear scanning portion of the process, one set of delays can be used for all scan lines. Hence, the trapezoidal scanning embodiment of the invention involves a combination of phased array scanning at both ends of the region and linear scanning in the middle of the region.

In a typical ultrasound imaging system, electronic circuitry capable of providing up to 10-20~s delay with sub-microsecond time resolution is needed to provide precise signal path compensation. In one preferred embodiment of the present invention, this wide range of delays with fine resolution is provided by a dual-stage programmable tapped delay line using CCD technology. The first stage introduces a fine delay and the second stage introduces a coarse delay. The delays are controlled by tapping clock frequencies, the fine delay being controlled by a higher clock frequency than the coarse delay. In one embodiment, the fine delay clock frequency is set at eight times the ultrasound signal frequency, and the coarse delay clock frequency is set at one-tenth the fine delay clock frequency. The clock frequencies are separately controllable to facilitate varying the ultrasound signal frequency to vary imaging depth.

Such devices are described in copending U.S. patent application Ser. No. 08/496,915, entitled, "Integrated Beam Forming and Focussing Processing Circuit for Use in an Ultrasound System," by Alice M. Chiang and copending U.S. patent application Ser. No. 08/496,463, entitled, "Integrated Delay Processing Circuit," by Alice M. Chiang, both of which were filed on Jun. 29, 1995. Both patent applications are incorporated herein by reference.

In one embodiment, the frequency of the ultrasound signals is variable to allow for imaging at varying depths. This can be accomplished by internal or external adjustment of transducer signal driving frequency. Alternatively, for wider variations in frequency, the system of the invention accommodates different scan heads having arrays which operate at different frequencies. Also, the scan head of the invention can be provided with a facility for changing arrays based on the desired operating frequency.

In an alternative preferred embodiment of the present invention, the delay processing circuits utilize a single charge-coupled device delay line with a programmable input sampling selection circuit. The programmable input sampling selection circuit allows nonuniformly sampled imaging signals to be loaded into the programmable delay line to provide the required variable delay.

In this embodiment, each delay processing circuit includes a programmable input sampling circuit and a programmable delay unit. According to a user specified selection pattern, the programmable sampling circuit converts a continuous-time input waveform into a sequence of discrete-time analog sample data, which can be uniformly or nonuniformly spaced, and which are loaded into the programmable delay unit. A control circuit is included to provide programmable delay to each selected sampled data. A summation circuit is incorporated for summing the sampled, delayed data from each of the delay units to produce a focused image.

In one embodiment, the control circuit used to control the delay of each sample includes a counter and a storage circuit, which can be a shift register or a memory circuit. The shift register can be formed using CCD technology or other logic circuit technology. Before each scan line is generated, the storage circuit is loaded with a series of data values which define the delays used for each focus point along a scan line. Under control of a sampling clock, counter outputs are compared one at a time to values stored in the shift register. A matched value results in a sample being taken of the signal. Hence, by storing appropriate values in the memory circuit (shift register), sample delay can be controlled.

In one embodiment, the shift register also stores a value that addresses the appropriate stage of the programmable delay line depending upon the predetermined delay for the sample. Preferably, this delay tap value is stored as a series of data bits with the corresponding value used to provide sampling delay as described above. In one embodiment, the two values are combined into a single data word comprising nine data bits, three for the sample delay selection and six for the delay tap selection in the delay line. In one embodiment of the invention, each scan line includes 512 focus points. Thus, the shift register is a 512-stage 9-bit shift register. Alternatively, four bits can be used for sample delay selection and seven for the delay top selection, resulting in a 512-stage II-bit shift register being used.

In another embodiment, the 9-bit data words are compressed to permit more efficient storage of the data. In this embodiment, instead of storing each individual delay, only the differences in delay between adjacent focus points are stored. Each first difference requires fewer bits to store than does the actual absolute delay value. In another embodiment, second differences, Le., the difference between adjacent first differences, is stored at each register location. This requires even fewer bits. To process each delay, a processor of the invention reads each difference and integrates it to generate an actual delay value which is used to control both the sampling and tapping of the delay line. In the first difference embodiment, a single summing stage is used to perform the integration. In the case of second difference storage, a two-stage adder is used.

In one embodiment of the invention, a process referred to as sub-aperture scanning can be implemented. Under this process, processing circuits are shared by the transducers such that the total number of processing circuits is fewer than the number of transducer elements. For example, the array can include 128 transducer elements but only 64 processing channels. In this embodiment, a multiplexing process is used whereby only a portion of the 128 transducers, i.e., a "sub-aperture," is used at one time. A multiplexing circuit is used to route signals from the active transducers to the processing circuitry. In one embodiment, 64 transducers are used at once, and they are serviced by the 64 channels of processing circuitry. After image data is obtained for a first group of 64 transducers, a next group of transducers is activated to collect more data. Typically, a sliding scanning process is used in which each successive group of 64 elements slides over one element, resulting in overlapping sub-aperture scanning regions. During sub-aperture scanning, a spatial windowing process is used to reduce image clutter, i.e., energy in the image obtained through the side lobes rather than the main lobe of the array response. Either a dynamically varying spatial window or a truncated non-varying spatial window can be used. However, it has been found that the truncated window is easier to implement.

In this embodiment, to set the delays for each group of active elements, in the linear scanning mode, the same set of delays is downloaded to memory for the sets of elements. As the sub-aperture moves to successive groups, the digital words representing the individual delays are effectively rotated through the memory and control circuits of each processing channel. That is, for the first, group of elements, delay sets numbered 1-64 are loaded into processing channels 1-64, respectively. For the next set, delay sets 1-64 are loaded into processing channels 2-64, 1, respectively. For the next set, delays 1-64 are loaded into channels 3-64, 1-2, respectively, and so forth. This rotational multiplexing of delay data values substantially enhances the efficiency of the invention since the amount of memory required to store all the delays is substantially reduced. The amount of hardware required is also reduced.

In another, alternative preferred embodiment, an adaptive beam forming circuit is used instead of the dual-stage delay line to provide the required delays at the required resolution. In the adaptive beam forming technique, a feedback circuit senses summed received signals from a tapped delay line and generates correction signals. The correction signals control individual multiplier weights in the beam forming circuitry to adjust the summed signal and eliminate the effects of clutter and interference from the Image.

As described above, after the beam forming circuits dynamically focus and sum the signals from the ultrasonic transducers, the summed signal is forwarded over the system cable to the data processing and display subsystem of the imaging system. The data processing subsystem includes, among other things, demodulation, log compression and scan conversion circuitry for converting the polar coordinates of received ultrasonic signals to rectangular coordinates suitable for further processing such as display. The scan conversion process of the present invention provides a higher quality image and requires far less complex circuitry than that of prior systems.

In the scan conversion of conventional systems, the value of each point on the (x,y) coordinate system is computed from the values of the four nearest neighbors on the polar (r,8) array by simple linear interpolation. This is accomplished by use of a finite state machine to generate the (x,y) traversal pattern, a bi-directional shift register to hold the (r,8) data samples and a large number of digital logic and memory units to control the process and ensure that the correct samples of (r,8) data arrive for interpolation at the right time for each (x,y) point since the (x,y) data points are received asynchronously.

In the present invention, hardware complexity and cost are reduced by using a number-theoretic scheme for reliably generating the (x,y) grid traversal path in natural order, i.e., using the (r,8) samples as they are acquired. This provides greater flexibility and better fidelity to the actual medical data since it permits the array traversals to be designed so that they do not impose an unnatural image reconstruction scheme. The approach taken in the present invention provides greater flexibility in that multiple effective paths through the (x,y) array are possible. As a result, full advantage is taken of different ultrasound scan frequencies and, hence, imaging depth.

After the image data is scan converted, it is post processed in accordance with its eventual intended presentation format. For example, the data can be digitized and formatted for presentation on a display. Alternatively, the (x,y) data values can be presented to a video compression subsystem which compresses the data to allow for data transmission to remote sites by modem or other known communication means.

The ultrasound imaging system of the invention also allows for imaging of moving objects by including a pulsed Doppler processing subsystem. Data from the beam forming circuitry is forwarded to the pulsed Doppler processor to generate data used to image the moving object. For example, the pulsed Doppler processor can be used to produce color flow map images of blood flowing through tissue.

In another preferred embodiment, the data processing and display unit can be a single small battery-operated unit. It can be hand-held or worn clipped to the user or in the user's pocket. This, in conjunction with the hand-held scan head of the invention, makes the ultrasound system of the invention completely portable.

The ultrasound imaging system of the invention has several advantages over prior conventional systems. Because much of the signal processing circuitry is integrated on small chips, the signal processing can be carried out in the scan head. Because of the proximity of the transducers to the processing circuitry, signal loss is substantially reduced. This results in greatly improved system performance in the form of high-resolution high-quality images. Also, since the signal summing is also performed in the scan head, only a single or very few cable conductor lines are required to transmit image signals to the data processing circuitry. The required cable is far less complex and expensive than that used in conventional systems.

The portability of the imaging system of the invention is also a very important asset. As described above, the system includes a small hand-held scan head, a small cable and a portable data processing and display unit such as a lap-top computer or hand-held computer with integrated liquid crystal or other flat panel display and keypad. It can be battery powered and hence can easily be carried to persons needing immediate attention at remote locations to perform quick diagnostic evaluation. By using the video data compression of the invention, the image data gathered at a remote site can be transferred by modem or wireless cellular link or other known means to a hospital for evaluation. Treatment instructions can then be relayed back to the operator where the patient can be administered treatment immediately.

Another preferred embodiment of the invention involves the above described circuits and methods for a two-dimensional transducer array device. The transducer device provides focusing in a second dimension and can employ a coarser spacing between the rows of a multi-linear array, for example.

Another preferred embodiment of the invention involves the use of an ultrasound transducer device in an electronic stethoscope. This system provides both audio information to the user as well as an ultrasound imaging capability.

Another preferred embodiment of the invention involves the use of an ultrasound transducer device in a skinpatch. This can be used for cardiac monitoring by positioning the transducer device to transmit and receive between the ribs of a patient.

Another preferred embodiment of the invention incorporates the processing and control circuitry described herein in a distal end of an ultrasound internal probe or imaging catheter. This provides a more flexible and less expensive imaging probe that is useful for both diagnosis and treatment.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 1A and 1B respectively show a block diagram of a conventional imaging array as used in an ultrasound imaging system and associated transmitting pulse patterns of a single pulse and multiple pulses in a zone-focused mode.

FIGS. 39A and 39B illustrate an ultrasound transducer patch system in accordance with the invention.

FIGS. 40A and 40B illustrate an ultrasound probe or catheter in accordance with the invention.

Figure 2A:
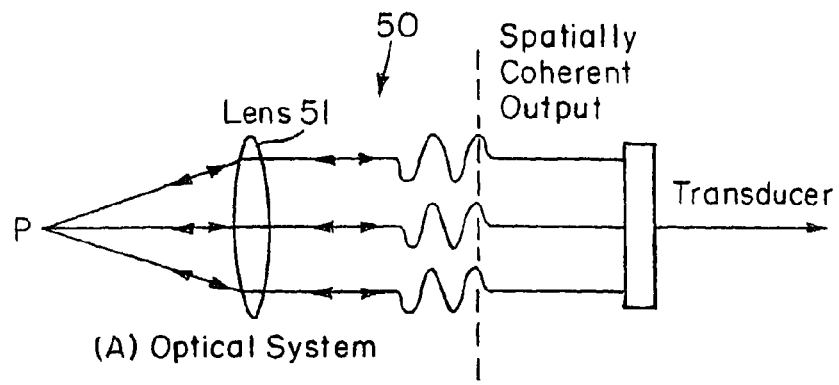
FIGS. 2A-2C respectively show block diagrams of three different conventional imaging or beam focusing techniques involving optical lens, time delay and phase delay operations.
Figure 2B:
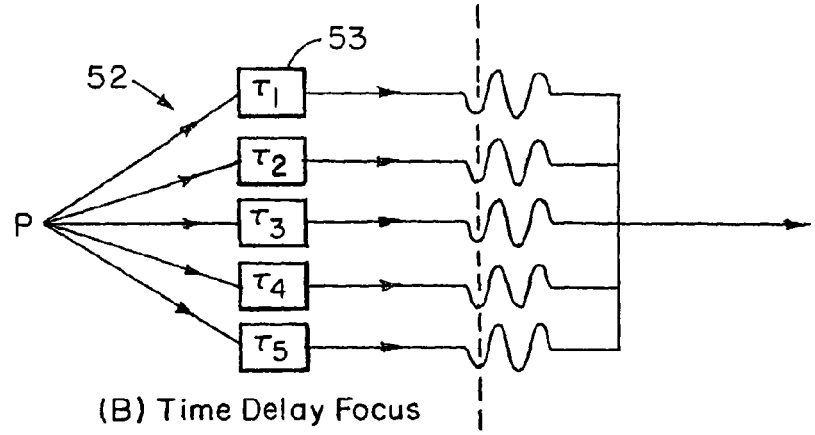
Figure 2C:
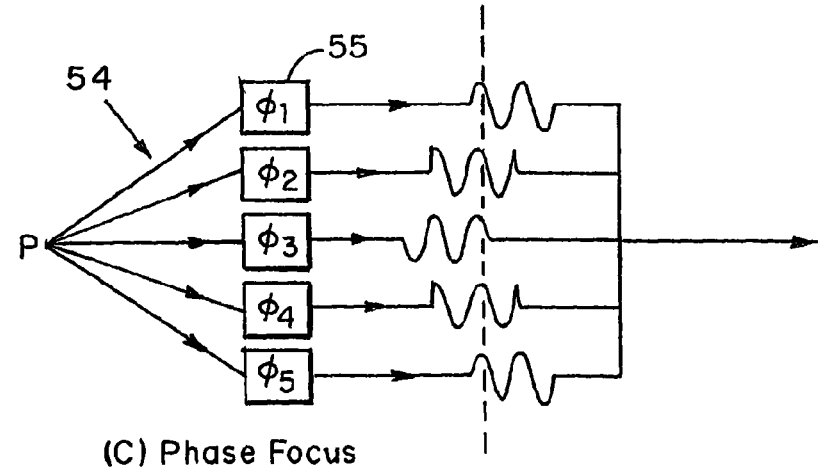

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 3:
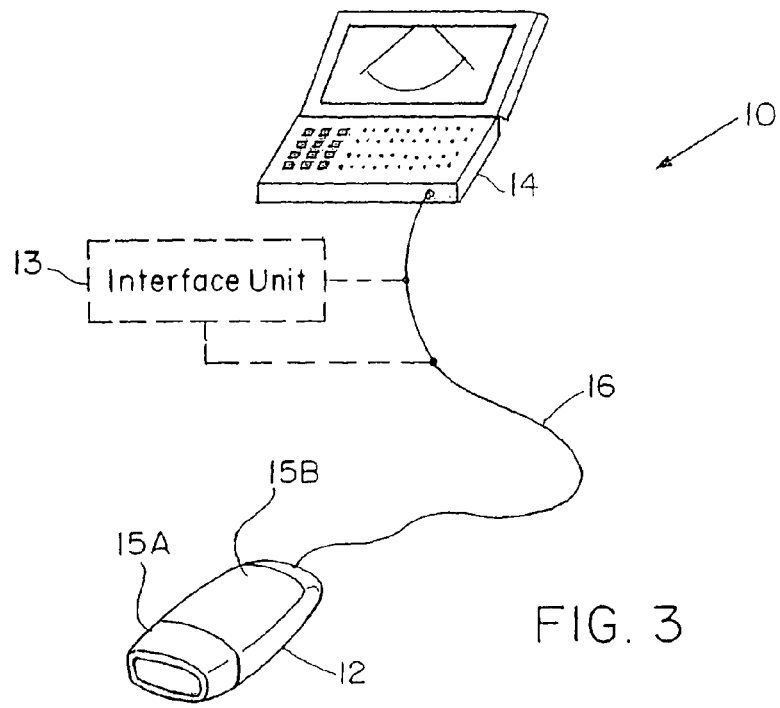
FIG. 3 is a schematic pictorial view of a preferred embodiment of the ultrasound imaging system of the present invention.

FIG. 3 is a schematic pictorial view of the ultrasound imaging system 10 of the present invention. The system includes a hand-held scan head 12 coupled to a portable data processing and display unit 14 which can be a lap-top computer. Alternatively, the data processing and display unit 14 can include a personal computer or other computer interfaced to a cathode ray tube (CRT) for providing display of ultrasound images. The data processor display unit 14 can also be a small, lightweight, single-piece unit small enough to be hand-held or worn or carried by the user. The hand-held display is less than 1000 cm$^3$ in volume and preferably less than 500 cm$^3$. Although FIG. 3 shows an external scan head, the scan head of the invention can also be an internal scan head adapted to be inserted through a lumen into the body for internal imaging. For example, the head can be a transesophogeal probe used for cardiac imaging.

The scan head 12 is connected to the data processor 14 by a cable 16. In an alternative embodiment, the system 10 includes an interface unit 13 (shown in phantom) coupled between the scan head 12 and the data processing and display unit 14. The interface unit 13 preferably contains controller and processing circuitry including a digital signal processor (DSP). The interface unit 13 performs required signal processing tasks and provides signal outputs to the data processing unit 14 and/or scan head 12.

The hand-held housing 12 includes a transducer section 15A and a handle section 15B. The transducer section 15A is maintained at a temperature below 41° C. so that the portion of the housing that is in contact with the skin of the patient does not exceed this temperature. The handle section 15B does not exceed a second higher temperature preferably 50° C. The hand-held scan-head occupies a volume of less than 1000 cm$^3$ and preferably less than 500 cm$^3$, and is less than twenty centimeters in length along it's major axis.

Figure 4:
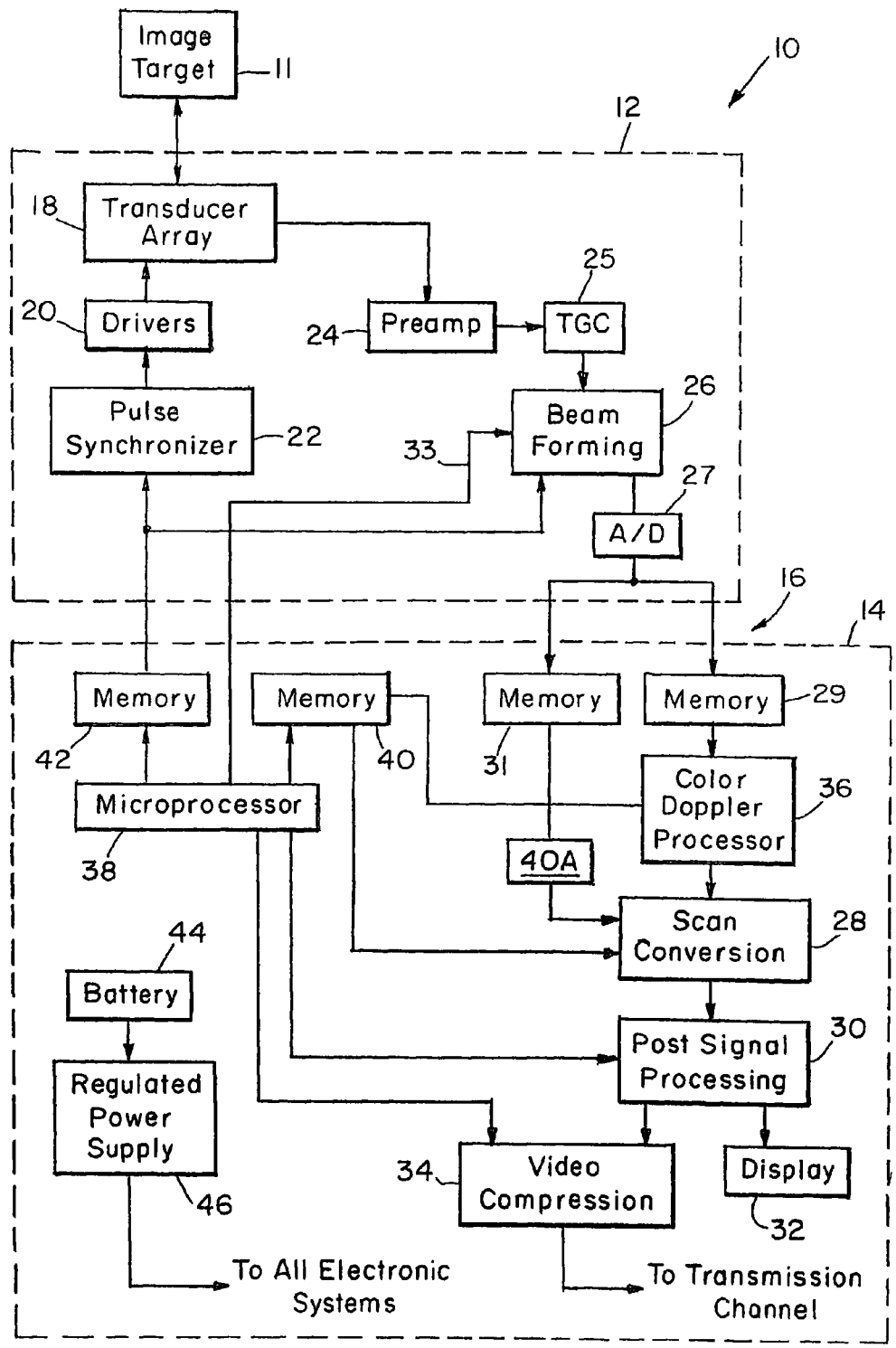
FIG. 4 is a schematic functional block diagram of a preferred embodiment of the ultrasound imaging system of the invention.

FIG. 4 is a schematic functional block diagram of one embodiment of the ultrasound imaging system 10 of the invention. As shown in FIG. 4, the scan head 12 includes an ultrasonic transducer array 18 which transmits ultrasonic signals into a region of interest or image target 11, such as a region of human tissue, and receives reflected ultrasonic signals returning from the image target. The scan head 12 also includes transducer driver circuitry 20 and pulse synchronization circuitry 22. The pulse synchronizer 22 forwards a series of precisely timed and delayed pulses to high voltage driver circuits in the drivers 20. As each pulse is received by the drivers 20, the high-voltage driver circuits are activated to forward a high-voltage drive signal to each transducer in the transducer array 18 to activate the transducer to transmit an ultrasonic signal into the image target 11.

Ultrasonic echoes reflected by the image target 11 are detected by the ultrasonic transducers in the array 18. Each transducer converts the received ultrasonic signal into a representative electrical signal which is forwarded to preamplification circuits 24 and time-varying gain control (TGC) circuitry 25. The preamp circuitry 24 sets the level of the electrical signals from the transducer array 18 at a level suitable for subsequent processing, and the TGC circuitry 25 is used to compensate for attenuation of the sound pulse as it penetrates through human tissue and also drives the beam forming circuits 26 (described below) to produce a line image. The conditioned electrical signals are forwarded to the beam forming circuitry 26 which introduces appropriate differential delay into each of the received signals to dynamically focus the signals such that an accurate image can be created. The signals delayed by the beam forming circuitry 26 are summed to generate a single signal which is forwarded over the cable 16 to the data processor and display unit 14. The details of the beam forming circuitry 26 and the delay circuits used to introduce differential delay into received signals and the pulses generated by the pulse synchronizer 22 will be described below in detail.

In one preferred embodiment, the dynamically focused and summed signal is forwarded to an A/D converter 27 which digitizes the summed signal. Digital signal data is then forwarded from the A/D 27 over the cable 16 to buffer memories 29 and 31. It should be noted that the A/D converter 27 is not used in an alternative embodiment in which the analog summed signal is sent directly over the system cable 16. The AID converter 27 is omitted from further illustrations for simplicity.

Data from buffer memory 31 is forwarded through demodulation and log compression circuitry 40A to scan conversion circuitry 28 in the data processing unit 14. The scan conversion circuitry 28 converts the digitized signal data from the beam forming circuitry 26 from polar coordinates (r,8) to rectangular coordinates (x,y). After the conversion, the rectangular coordinate data is forwarded to post signal processing stage 30 where it is formatted for display on the display 32 and/or for compression in the video compression circuitry 34. The video compression circuitry 34 will be described below in detail.

Digital signal data is forwarded from buffer memory 29 to a pulsed or continuous Doppler processor 36 in the data processor unit 14. The pulsed or continuous Doppler processor 36 generates data used to image moving target tissue 11 such as flowing blood. In the preferred embodiment, with pulsed Doppler processing, a color flow map is generated. The pulsed Doppler processor 36 forwards its processed data to the scan conversion circuitry 28 where the polar coordinates of the data are translated to rectangular coordinates suitable for display or video compression.

A control circuit preferably in the form of a microprocessor 38 controls the operation of the ultrasound imaging system 10. The control circuit 38 controls the differential delays introduced in both the pulsed synchronizer 22 and the beam forming circuitry 26 via a memory 42 and a control line 33. In one embodiment, the differential delays are introduced by programmable tapped CCD delay lines to be described below in detail. The delay lines are tapped as dictated by data stored in the memory 42. The microprocessor 38 controls downloading the coarse and fine delay line tap data from memory 42 to on-chip memories in both the pulsed synchronizer 22 and the beam forming circuitry 26. In another embodiment, the delays are controlled by delay processing circuitry which includes programmable input sampling circuits coupled to programmable delay units as described in detail below.

The microprocessor 38 also controls a memory 40 which stores data used by the pulsed Doppler processor 36 and the scan conversion circuitry 28. It will be understood that memories 40 and 42 can be a single memory or can be multiple memory circuits. The microprocessor 38 also interfaces with the post signal processing circuitry 30 and the video compression circuitry 34 to control their individual functions. The video compression circuitry 34 as described below in detail compresses data to permit transmission of the image data to remote stations for display and analysis via a transmission channel. The transmission channel can be a modem or wireless cellular communication channel or other known communication means.

The portable ultrasound imaging system 10 of the invention can preferably be powered by a battery 44. The raw battery voltage out of the battery 44 drives a regulated power supply 46 which provides regulated power to all of the subsystems in the imaging system 10 including those subsystems located in the scan head 12. Thus, power to the scan head is provided from the data processing and display unit 14 over the cable 16.

Figure 5:
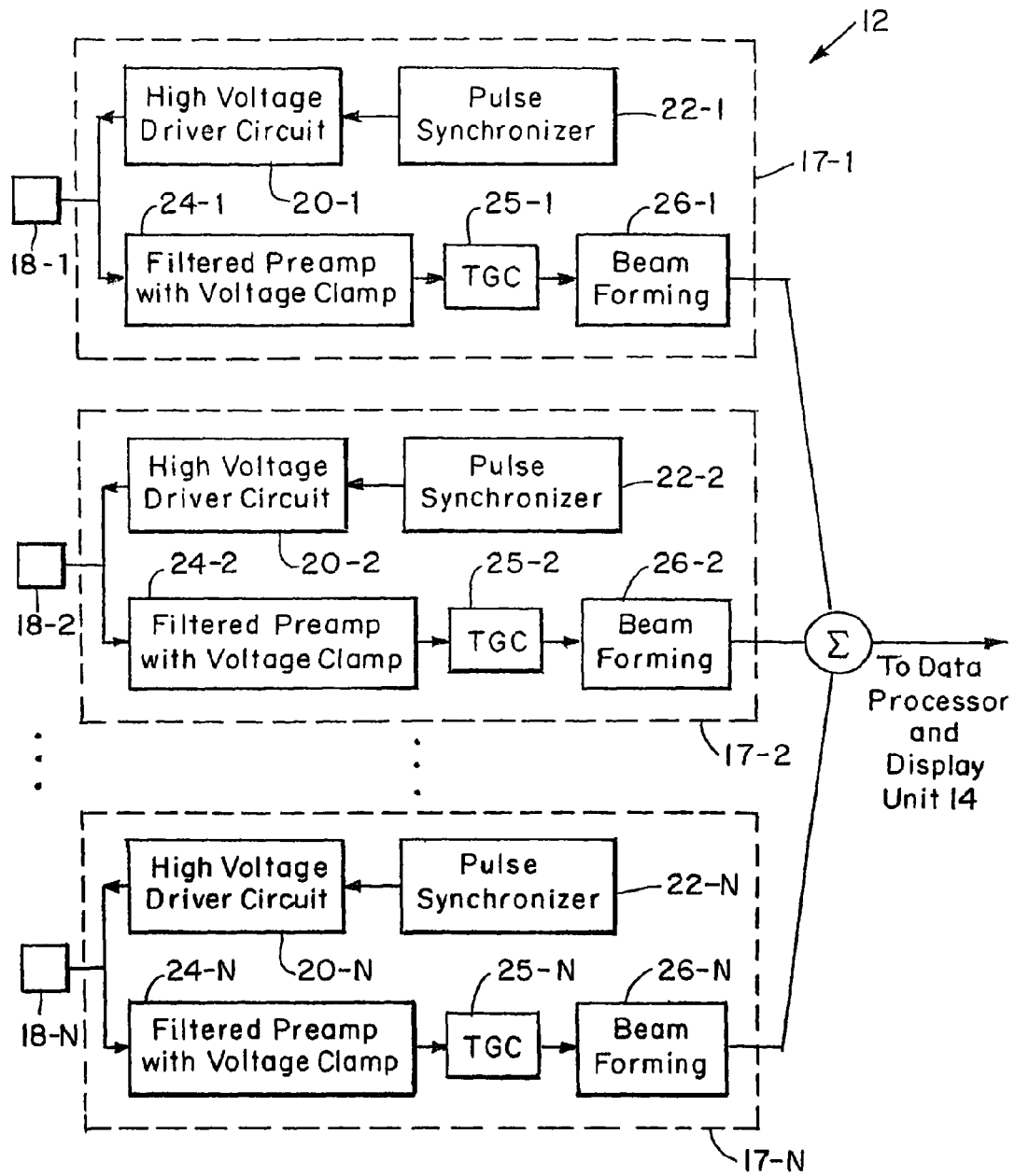
FIG. 5 is a schematic functional block diagram of a preferred embodiment of the ultrasound scan head of the present invention.

FIG. 5 is a detailed schematic functional block diagram of one embodiment of the scan head 12 used in the ultrasound imaging system 10 of the invention. As described above, the scan head 12 includes an array of ultrasonic transducers labeled in FIG. 3 as 18-(1), 18-(2), . . . , 18-(N), where N is the total number of transducers in the array, typically 128. Each transducer 18(1)-18(N) is coupled to a respective processing channel 17(1)-17(N).

Each processing channel 17(1)-17(N) includes a respective pulse synchronizer 22(1)-22(N) which provides timed activation pulses to a respective high voltage driver circuit 20(1)-20(N) which in turn provides a driving signal to a respective transducer 18(1)-18(N) in the transmit mode. Each processing channel 17(1)-17(N) also includes respective filtered preamplification circuits 24(1)-24(N) which include voltage clamping circuits which, in the receive mode, amplify and clamp signals from the transducers 18(1)-18(N) at an appropriate voltage level. The time varying gain control circuitry (TGC) 25(1)-25(N) controls the level of the signals, and the beam forming circuitry 26(1)-26(N) performs dynamic focusing of the signals by introducing differential delays into each of the signals as described below in detail. The outputs from beam forming circuits 26(1)-26(N) are summed at a summing node 19 to generate the final focused signal which is transmitted over the cable 16 to the data processor and display unit 14 for subsequent processing.

In the present invention, one embodiment of the beam forming and focusing circuit 26 can be integrated on a single microchip and utilizes cascaded charge-coupled device (CCD) tapped delay lines to provide individual coarse and fine delays resulting in a wide range of delays with fine time resolution. This embodiment of the beam forming system of the invention, referred to herein as charge domain processing (CDP) circuitry, includes a plurality of processing circuits which, in a receiving mode, differentially delay signals representative of image waveforms received as reflected ultrasonic energy from the target object in order to generate a focused image. In a transmitting mode, the processing circuits differentially delay signals, which are to be transmitted as ultrasonic energy to a target object by the array 18 of transducers 18(1)18(N), in order to generate a focused directional beam.

Each of the processing circuits includes a first delay line having a plurality of delay units operable in the receiving mode for receiving an image waveform and converting same into sampled data such as charge packets. In the transmitting mode, the first delay line receives the imaging signals and converts them into sampled data such as charge packets. A selection control circuit is operable for reading the sampled data from a selected first delay unit of the first delay line so as to correspond to a selected first time delay to accommodate fine delay resolution of the image waveform or imaging signals. A second delay line having a plurality of delay units is operable for sensing the sampled data from the selected first delay unit. The control circuit is further operable for reading the sampled data from a selected second delay unit of said second delay line so as to correspond to a selected second delay time to accommodate coarse delay resolution of the image waveform or imaging signals.

In the receiving mode, a summation circuit is provided for summing the sampled data from each of the selected second delay units in each of the processing circuits in order to produce a focused image. In the transmitting mode, an output circuit is provided for converting the sampled data from each of the selected second delay units in each of the processing circuits into signals representative of the focused directional beam.

The beam forming and focusing operations involve forming a summation of the waveforms as observed by all of the transducer elements. However, in this summation, the waveforms must be differentially delayed so that they all arrive in phase at a summation circuit 19 (see FIG. 5). Accordingly, each beam forming circuit 26 in accordance with the present invention provides a different time delay on each processing channel, and further varies that delay with time. The signals which are added in phase to produce a focused signal are then forwarded to the data processor and display unit 14.

For each nominal scanning direction, the differential delay required for information received by a transducer element 18($k$) in the array, relative to the first element 18(1), varies predominantly with k, with a small correction as a function of time to correct focus for depth. The overall control of delay can involve very fine time resolution as well as a large range of delays. However, for a selected beam forming direction, this set of delays is achieved by a combination of a coarse delay in each channel to approximately compensate for direction, and a fine delay for each channel which combines the functions of focusing and refining the original coarse correction.

Figure 6:
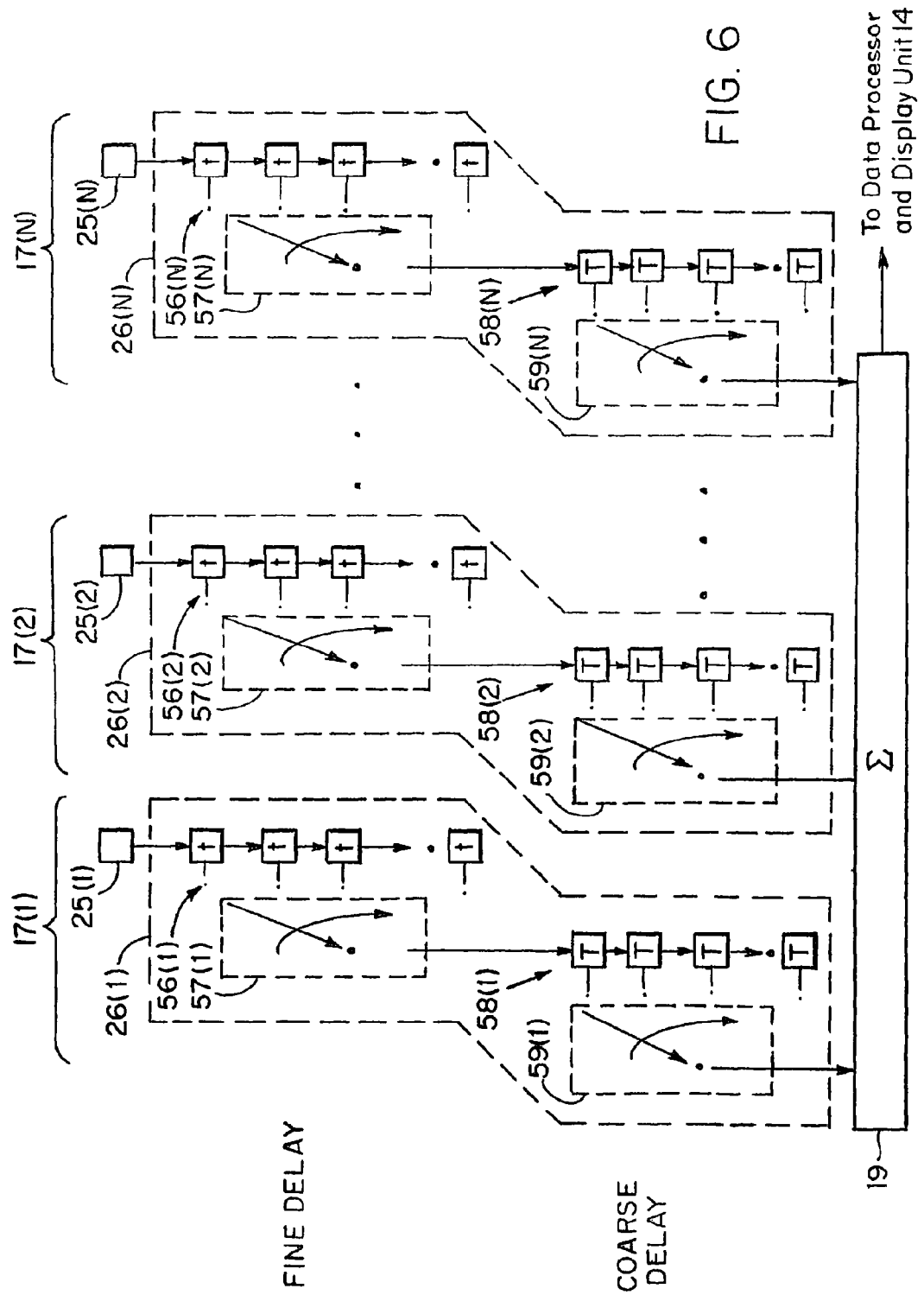
FIG. 6 shows an operational block diagram of an array of the beam forming and focusing circuits in accordance with the present invention.

According to one preferred embodiment of the beam forming circuitry 26 shown in operational block diagram form in FIG. 6, each of the beam forming circuits 26 is respectively arranged in a predetermined one of the N-parallel processing channels 17(1)-17(N), one for each of the array of transducer elements 18(1)-18(N). Each beam forming circuit 26 includes two cascading tapped delay lines 56(1)-56(N), 58(1)-58(N). Each circuit 26 receives as an input a signal from a TGC circuit 25 (see FIG. 3). The first delay line 56 in each channel provides a fine time delay for its received signal, while the cascaded second delay line 58 provides a coarse time delay. Each fine delay line has an associated programmable tap-select circuit 57(1)-57(N), and each coarse delay line has a programmable tap-select circuit 59(1)-59(N), both of which will be described in more detail hereinafter. The tap-select circuits are operable for effecting a variable delay time as a function of tap location.

During the operation of the circuits 26, signals which are received by each transducer element 18 are applied continuously to the input of its corresponding processing channel 17. The input signals to each processing channel are converted into a sequence of sampled data for initial propagation through the respective fine tapped delay lines 56. In accordance with a preferred embodiment of the present invention, both the fine 56 and coarse 58 tapped delay lines are charge-coupled device (CCD) tapped delay lines. Exemplary programmable CCD tapped delay lines are described in, for example, Beynon et al., Charge-coupled Devices and Their Applications, McGraw Hill (1980), incorporated herein by reference. Accordingly, in the exemplary configuration of the processing circuit 26 using CCD delay lines, the input signals to each of the processing channels are converted to a sequence of charge packets for subsequent propagation through the fine and coarse delay lines.

At a predetermined time, which is dependent on the tap location selected by the system 10, a delayed sample is either destructively or nondestructively sensed from the selected tap of the fine delay line 56. The delayed sample is in turn input to the front end of the corresponding coarse delay line 58. The selected delay samples thereafter propagate through the coarse delay line, and are again destructively or nondestructively sensed at a properly selected tap location corresponding to a predetermined time delay designated in accordance with the operation of the ultrasound imaging system 10. The sensed sampled data from the coarse delay line of each processing channel is simultaneously summed by a summation circuit 19 to form the output beam.

Figure 7:
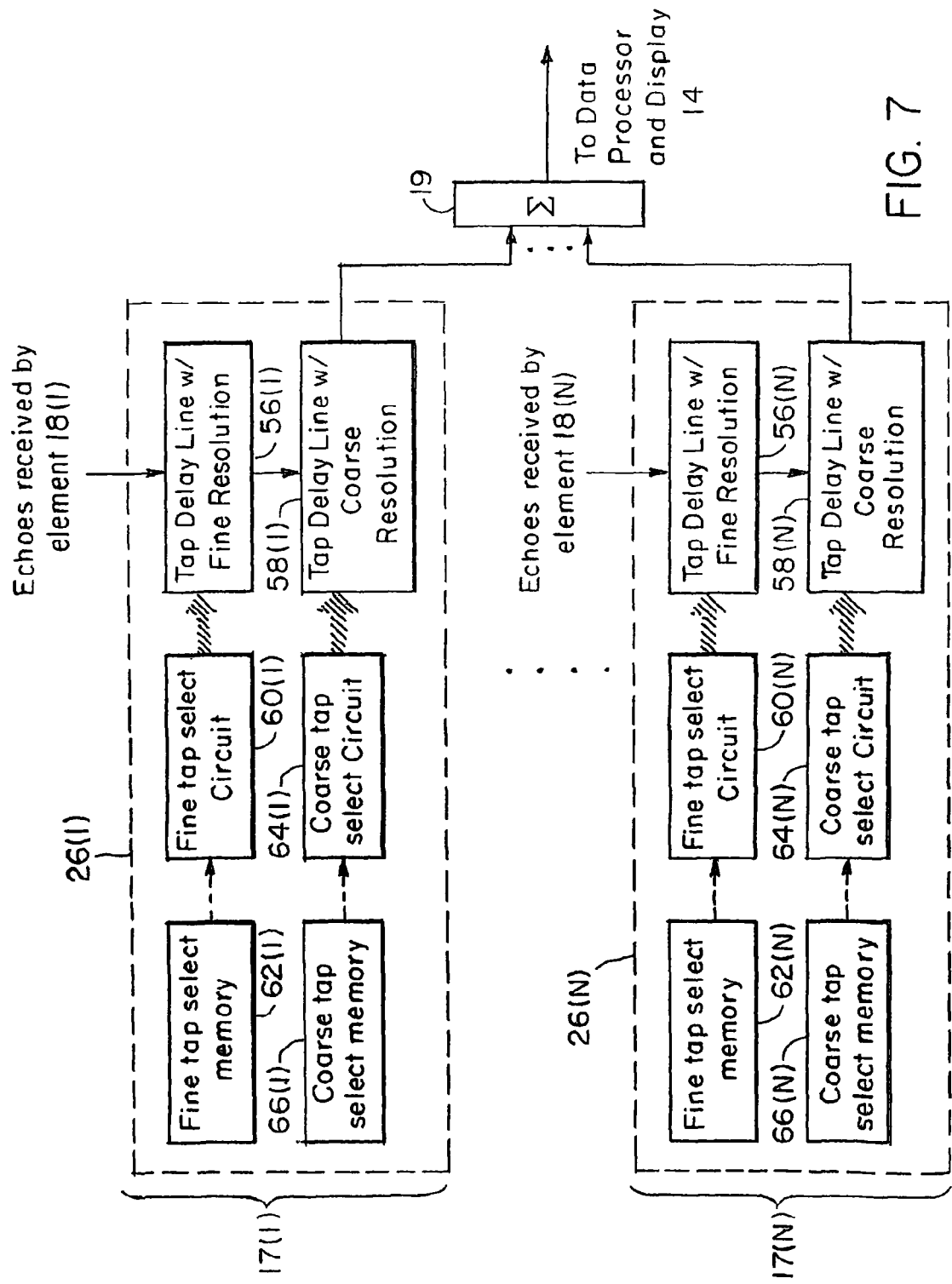
FIG. 7 shows a more detailed operational block diagram of an array of the beam forming and focusing circuits in accordance with the present invention.

With reference now to FIG. 7, a more detailed operational block diagram of the beam forming circuits 26(1)-26(N) of FIGS. 5 and 6 is shown. As illustrated, the programmable tap-select circuits 57(1)-57(N) for the fine delay lines each include respective fine tap select circuits 60(1)-60(N) and fine tap select memory units 62(1)62(N). In turn, the programmable tap-select circuits 59(1)-59(N) for the coarse delay lines each include respective coarse tap select circuits 64(1)-64(N) and coarse tap select memory units 66(1)-66(N).

In accordance with a preferred embodiment of the beam forming circuits, the fine and coarse delay lines have differing clock rates. The fine delay line is clocked at a higher rate than the coarse delay line and is therefore capable of providing a much finer delay time than that of the coarse delay line. For instance, in an exemplary configuration, each circuit 26 has a 32-stage fine tapped delay line clocked at 40 MHz and a 32-stage coarse-tapped delay line clocked at 2 MHz. Such a configured circuit can provide up to a 161 µs delay with a programmable 25 ns delay resolution. In contrast, it will be appreciated that if a single delay line were used, it would require approximately 640 stages of delays. Furthermore, due to the cascaded delay line structure of the beam forming circuits of the present invention, a local memory of 5-bit wide by 64-stage is adequate for providing the dynamic focusing function for a depth up to 15 cm. However, if a single delay structure were used, it would require a local memory of 640 bit wide by 1280-stage long.

During operation of an individual beam forming circuit 26, the fine delay line taps are changed continuously by the microprocessor 38 via the memory 42 (see FIG. 4) during each echo receiving time to provide dynamic focusing. The fine tap select circuit 60, in the form of a digital decoder, and the local fine tap select memory 62 are used to select the desired tap position of the fine delay line 56. For example, the microprocessor instructs the memory 42 to download a data word to memory 62 to provide a digital address representative of the selected tap position to the select circuit 60 for decoding. In turn, the select circuit 60 effects the sampling of data from the selected tap. In an exemplary embodiment, a 5-bit decoder is used to provide a 32-tap selection.

The tap position of the coarse delay line 58 is set once before each echo return and is not changed during each azimuth view direction. As with the operation of the fine delay line, the coarse tap select circuit 64, in the form of a digital decoder, is used in conjunction with the local coarse tap select memory 66 to select the desired tap position of the coarse delay line.

Figure 8:
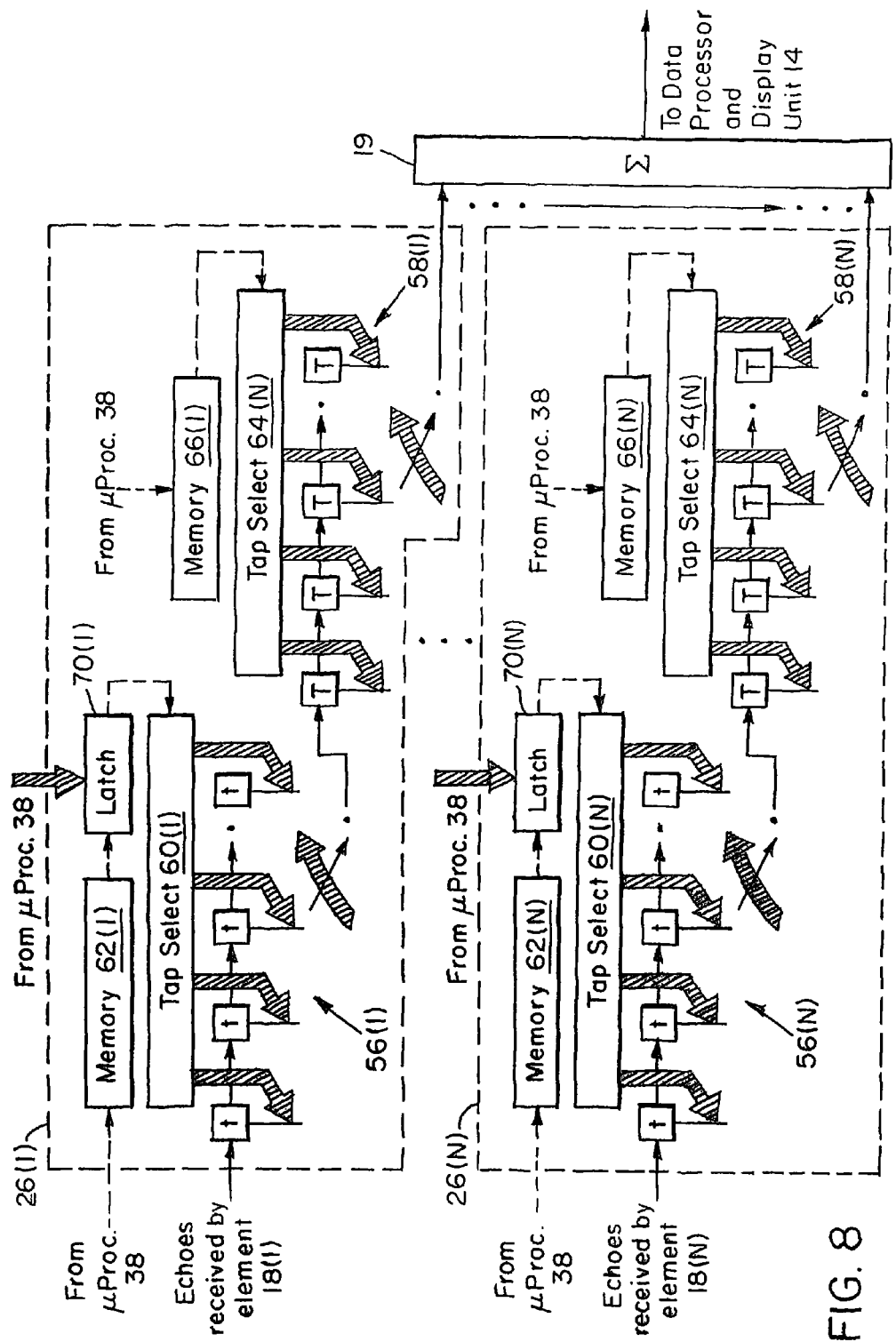
FIG. 8 shows an operational block diagram of an alternative embodiment of the present invention in which each of the beam forming and focusing circuits incorporates a latching circuit.

FIG. 8 shows an operational block diagram of an alternative embodiment of the beam forming circuitry 26 of the present invention in which each circuit 26 includes a respective latching circuit 70(1)-70(N) that generates a tap setting signal to each of the fine tap select circuits 60(1)-60(N). When the tap setting signal is provided to the fine tap select circuits, the tap selection will be fixed at the last tap of the fine tap delay lines (i.e. focusing point), thus the dynamic focusing function is not operable. This operation is controlled by the imaging system in situations where, for example, the imaging point is at a distance from the transducer elements which does not require a precise fine delay time. In this manner, the size of the fine tap select memory 62 is reduced.

Figure 9:
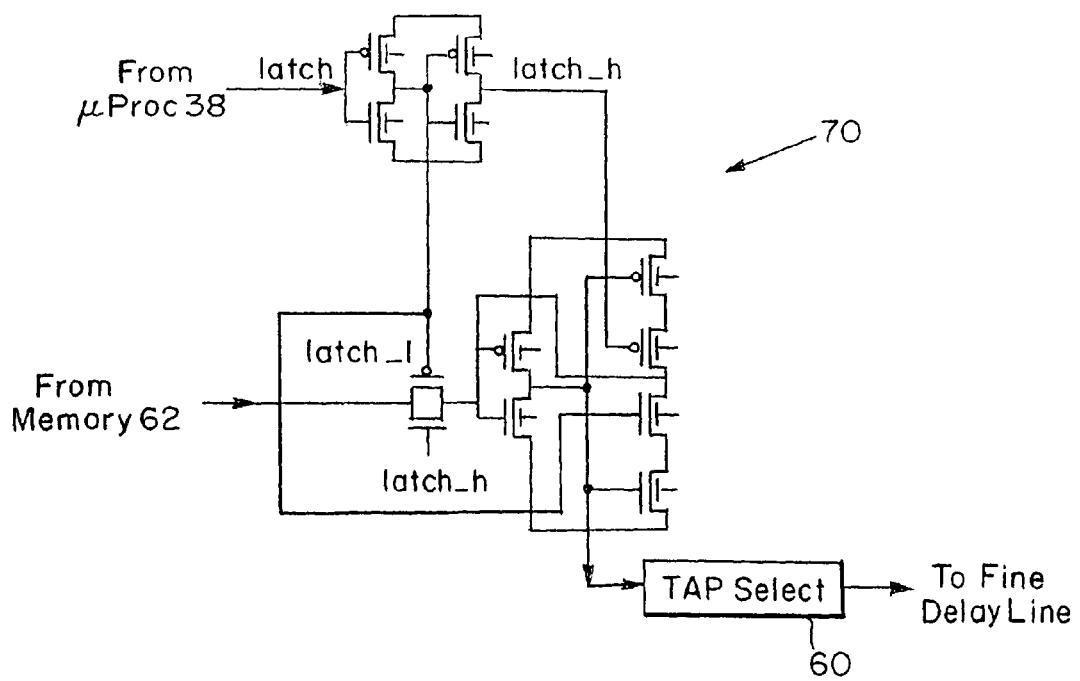
FIG. 9 shows a schematic block diagram of an exemplary embodiment of the latching circuit used in accordance with the present invention.

An exemplary embodiment of the latching circuit 70 in accordance with the present invention is shown in FIG. 9. In operation, when the latch is set high by the microprocessor 38, digital data from the memory 62 will pass through the CMOS passing transistors, and the defined transistor inverter provides an input to the appropriate tap select circuit (decoder) 60 so as to implement the dynamic focusing function. In contrast, when the latch is set low, the passing transistors are disabled, and thus the inverter output will be latched to the last data address in the memory, i.e., the last tap select position.

Using a 1.2-µm CCD/CMOS fabrication process provided by a conventionally known silicon foundry, Orbit Semiconductor, Inc., a prototype 10-channel beam forming microchip based on the fine/coarse delay architecture described above has been designed and fabricated. Due to the compactness of each fine and coarse delay line, and the simplification of its corresponding control circuits, this approach accommodates configuring the beam forming electronics of a 64-element receiver array to be integrated on one single microchip.

In the prototypical beam forming microchip of the present embodiment, each processing circuit includes two cascaded programmable tapped delay lines (each 16 stages long), two 4-bit CMOS decoders and a 4×64-bit local memory for storing the tap locations. The prototype is configured with 10 processing channels, each of which includes the processing circuit of the present invention fabricated on a single silicon microchip. Each processing circuit can provide up to 10 µs of programmable delay with a 25 ns delay resolution. The beam forming chip operates such that at each azimuth viewing angle, echo return signals from an image point at a given range resolution received by a transducer element are sampled by the corresponding processing channel. Each processing circuit provides ideally compensated delays to each received return signal. All of the delayed outputs are then summed together to form a single beam or a focused image point. The chip area associated with each processing channel is only 500×2000 µm$^2$, It follows that the dynamic beam forming electronics for a 64-element receiver array can be integrated in a single microchip with chip area as small as 64 mm$^2$, which corresponds to at least three to four order of magnitude size reduction compared to conventional devices.

The fine/coarse tapping architecture of the present invention accommodates a 12 µs delay with a 25 ns resolution with the two cascaded CCD tapped delay lines. Specifically, the architecture includes a first 16-stage long delay line clocked at 40 MHz and a second 32-stage long delay line clocked at 2 MHz. The shorter delay lines and the simplicity of the tapping circuit associated with these shorter delay lines allows all of the image-generating electronics to be integrated on a single chip. A single chip performs the electronic focus function for a 128-element array with more than two orders of magnitude reduction in chip area, power consumption and weight when compared with conventional implementations.

Figure 10:
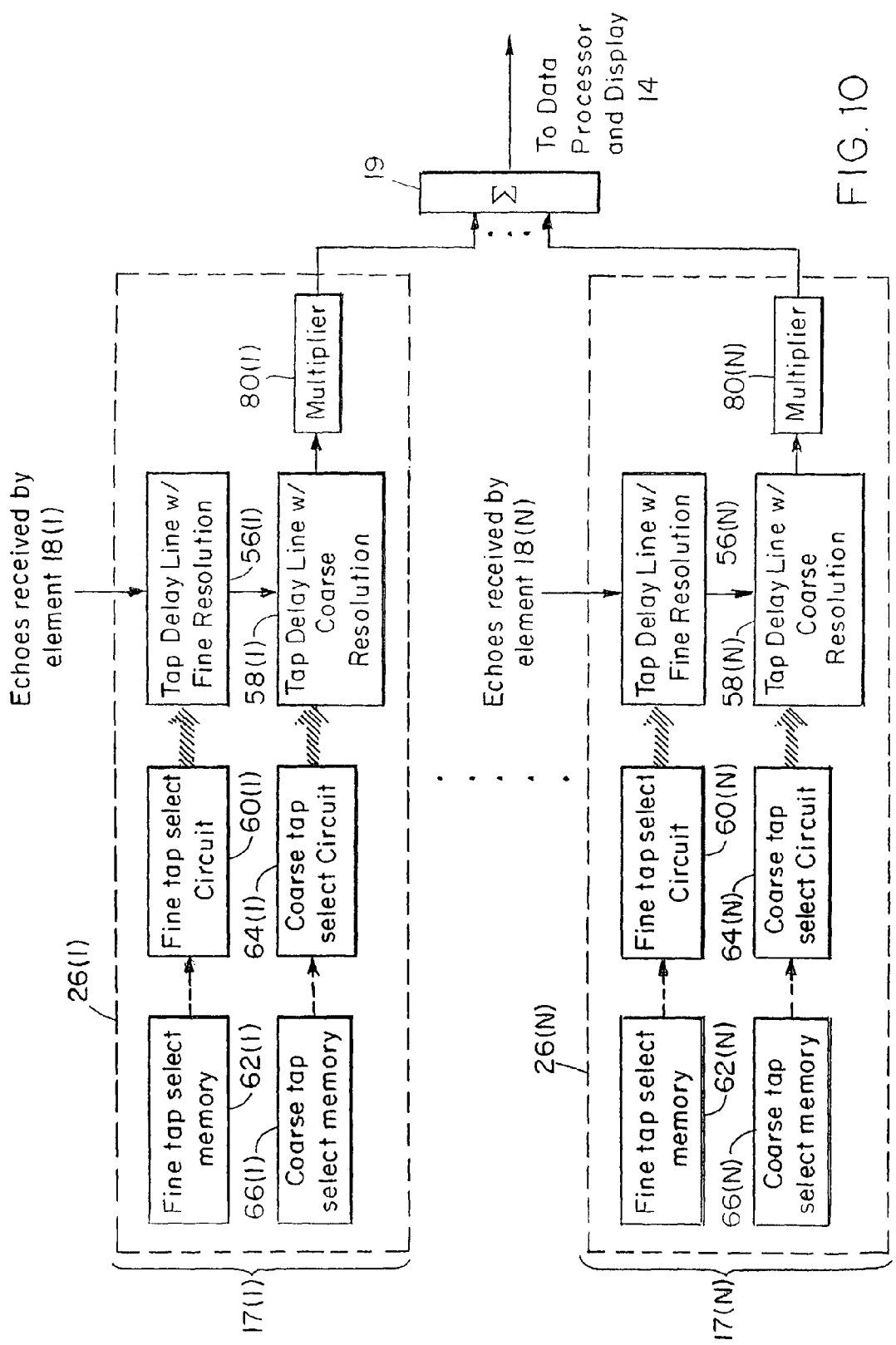
FIG. 10 shows an operational block diagram of an alternative embodiment of the present invention in which the selected outputs of each beam forming and focusing circuit are applied to respective multiplier circuits.

An operational block diagram of another alternative embodiment of the beam forming circuitry 26 of the present invention is shown in FIG. 10, in which the selected outputs of each coarse delay line 58(1)-58(N) are applied to respective multiplier circuits 80(1)-80(N) prior to being provided to the summation circuit 19. An exemplary multiplier for use in the aforementioned embodiment of the beam forming circuits is described in co-pending U.S. patent application Ser. No. 08/388,170, entitled "Single-Chip Adaptive Filter Utilizing Updatable Weighting Techniques," filed Feb. 10, 1995 by Alice M. Chiang, which is incorporated herein by reference.

The configuration of the multipliers 80 will accommodate the use of apodization techniques, such as incorporating a conventionally known Hamming weighting or code at the receiving array to reduce the sidelobe level and generate better quality imagery. Similar to the embodiment shown in FIG. 8, latch circuits 70(1)-70(N) may be included in association with each of the beam forming circuits 26(1)-26(N) in order to control the latching of the tap select position for the fine delay lines 56(1)-56(N). Conventional apodization and Hamming weighting techniques are described in, for example, Gordon S. Kino, Acoustic Waves: Devices, Imaging, and Analog Signal Processing, Prentice Hall, Inc. (1987), which is incorporated herein by reference.

Figure 11:
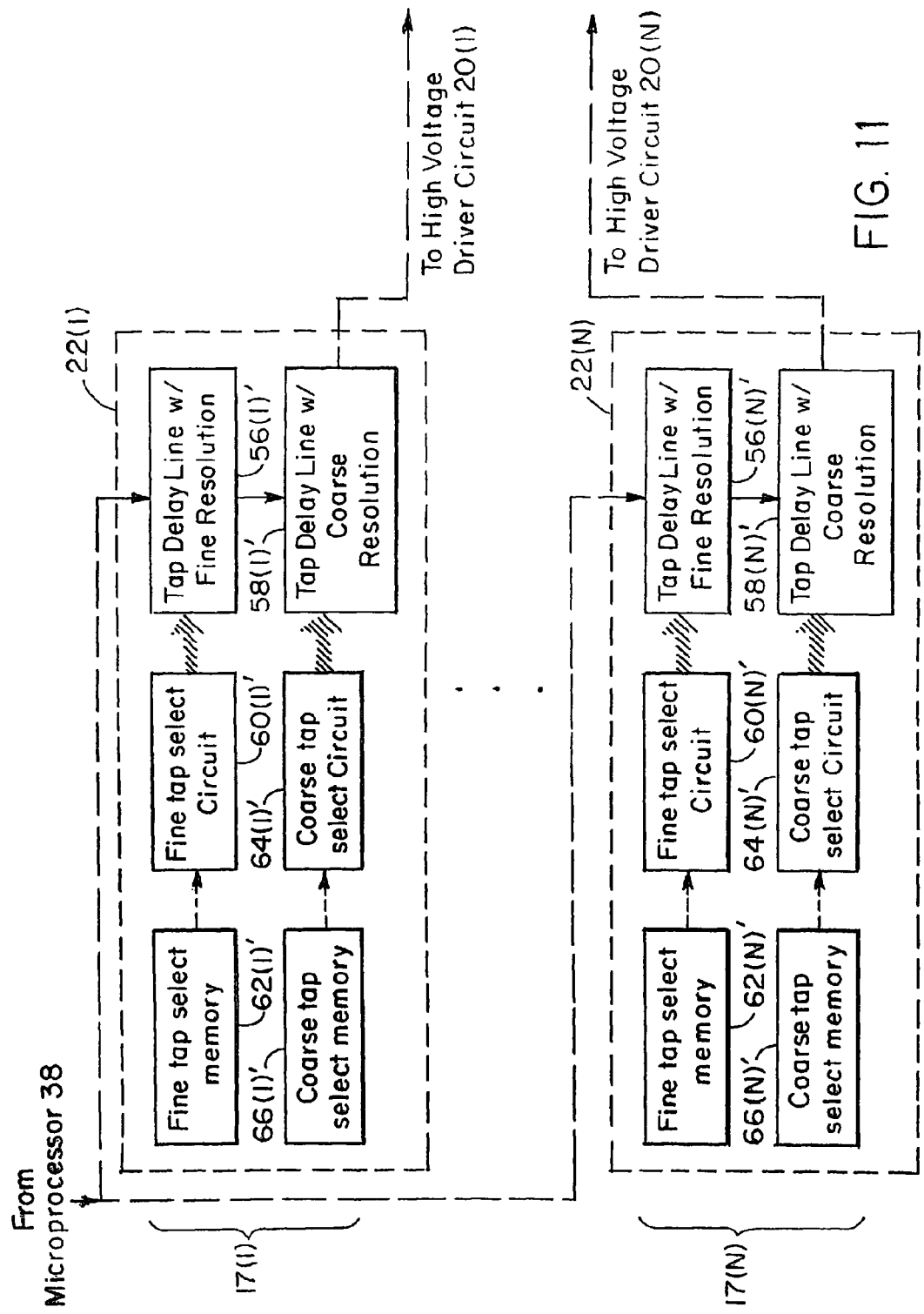
FIG. 11 shows an operational block diagram of an alternative embodiment of the present invention in which a plurality of beam forming and focusing circuits of the present invention are arranged for operation in a transmission mode.

FIG. 11 shows an operational block diagram of the cascaded dual tapped CCD delay lines used in pulse synchronizers 22(1)-22(N) to introduce delay into individual transmitted signals in the transmit mode of the ultrasound system 10 of the present invention. Each pulse synchronizer circuit 22(1)-22(N) includes two cascading tapped delay lines 56(1)'-56(N)' and 58(1)'-58(N)'. The first delay line 56' in each processing channel provides a fine time delay for the signals to be transmitted, while the cascaded second delay line 58' provides a coarse time delay. Each fine delay line has an associated programmable fine tap select circuit 60(1)'-60(N)', which receive tap select addresses from respective fine tap select memory units 62(1)'-62(N)'. Each coarse delay line has an associated programmable coarse tap select circuit 64(1)'-64(N)', which receive tap select addresses from respective fine tap select memory units 66(1)'-66(N)'. The tap-select circuits are operable for effecting a variable delay time as a function of tap location.

During the operation of the pulse synchronizers 22 in the transmission mode, signals which are provided from the microprocessor 38 via the memory 42 (see FIG. 4), are applied continuously to the inputs of each processing channel 17(1)-17(N). The input signals to each processing channel are converted into a sequence of sampled data for initial propagation through the respective fine tapped delay line 56. In an exemplary configuration of the pulse synchronizer circuits 22(1)-22(N) using CCD delay lines, the input signals to each of the processing channels are converted to a sequence of charge packets for subsequent propagation through the fine and coarse delay lines.

At a predetermined time which is dependent on the tap location selected by the imaging system, a delayed sample is either destructively or nondestructively sensed from the selected tap of the fine delay line 56. The delayed sample is in turn input to the front end of the corresponding coarse delay line 58. The selected delay samples thereafter propagate through the coarse delay line, and are again sensed at a properly selected tap location corresponding to a predetermined time delay designated in accordance with the operation of the microprocessor 38 of the ultrasound imaging system 10. The sensed sampled data from each of the coarse delay lines 58(1)-58(N) are then converted and transmitted as ultrasonic pulse signals by the corresponding transducer elements 18(1)-18(N). In accordance with a preferred embodiment of the present invention, the fine and coarse delay lines of each pulse synchronizer circuit have differing clock rates. In the transmission mode, the fine delay line can be clocked at either a higher or lower rate than that of the coarse delay line in order to accomplish the desired beam forming and focusing.

In another embodiment of the invention, an adaptive beam forming imaging (ABI) technique is used in both the beam forming circuits 26 and the pulse synchronizer circuits 22 to introduce the appropriate delays to produce a focused image. The adaptive beam forming technique improves image quality and spatial resolution by suppressing artifacts due to scattering sources and clutter in the sidelobes of the transducer array response. This adaptive beam forming circuitry can also be implemented on a single chip.

ABI is a model-based approach to image reconstruction derived from super resolution techniques. ABI offers improvements in resolution and reduction in sidelobes, clutter, and speckle. Super resolution algorithms modified for imaging include the two-dimensional maximum likelihood method (MLM) and two-dimensional multiple-signal classification (MUSIC). ABI incorporates models for the desired backscatter (amplitude and phase), providing better detection performance than conventional imaging methods.

Figure 12:
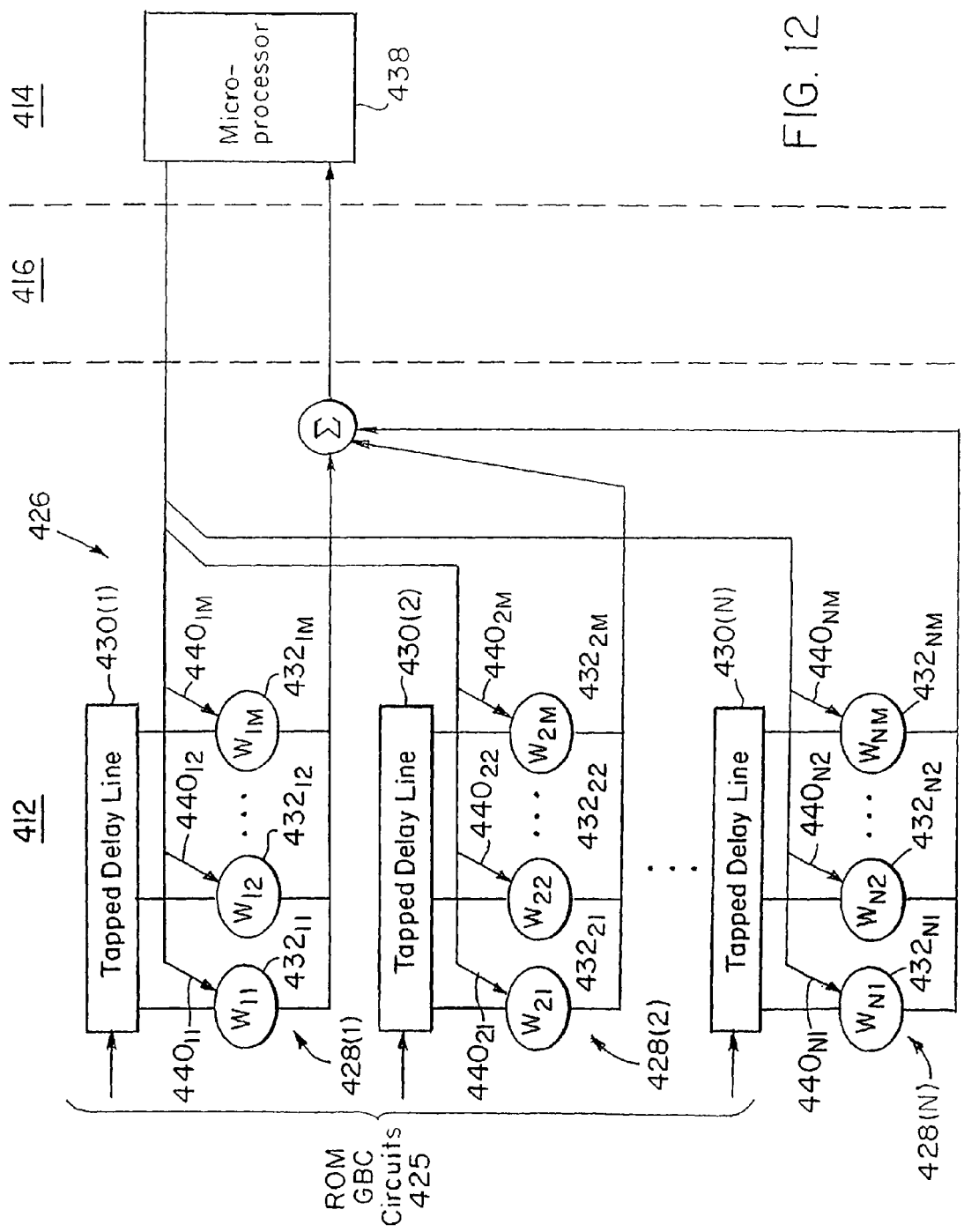
FIG. 12 is a schematic functional block diagram of one preferred embodiment of adaptive beam forming circuitry in accordance with the present invention.

FIG. 12 is a schematic functional block diagram depicting one embodiment of adaptive beam forming circuits 426 located in the scan head 412 in accordance with the present invention. In the adaptive beam forming circuits 426, individual multiplier weights of the finite impulse response (FIR) filter are controlled by a feedback loop, in such a way as to reduce clutter and interference or finite impulse response (FIR) filters. In either case, the adaptive circuits are used to remove clutter and interference such as that caused by ultrasonic signal in the sidelobes of the array pattern to produce an image with much higher accuracy and resolution.

Each processing channel 428(1)-428(N) of the beam forming circuits 426 receives a signal from a respective time-varying gain control (TGC) circuit 25 at a respective tapped delay line 430. The beam forming circuits 426 includes N processing channels 428, one for each transducer in the array 18. Signals tapped off of each tapped delay line 430 are received by a set of weighted multiplying D/A converters 432. Each processing channel k includes M weighted multipliers 432, labelled $432_{k1}$-$432_{kM}$. The weights of the multipliers 432 are set to generate an output signal from each processing channel which is summed at a summing node 419. The summed signal is forwarded over the system cable 416 to the system control circuit such as the microprocessor 438 in the data processing and display unit 414. The microprocessor 438 analyzes the signal for known characteristics of such effects as clutter, sidelobes and interference. In response to detecting such effects, the microprocessor 438 generates control signals used to drive the multiplier weights 432 to adjust the signals to eliminate these effects from the output signal and forwards the control signals to the multipliers via the system cable 416 on lines 440. Thus, the adaptive beam forming circuitry comprises a feedback circuit which alters received signals from a tapped delay line of each channel prior to summation of the signals. The summed signal is sensed and correction signals based on the sensing are forwarded in the feedback loop to the multipliers to correct the summed signal.

The ABI results in an image of much higher resolution and overall quality than is obtainable in prior systems. The ABI technique results in at least two to three times better resolution than that provided by conventional imaging techniques. As an example, in conventional ultrasound, at a frequency of 5 MHz, a resolution of about 1 mm can be obtained. Using ABI techniques, a lateral resolution of approximately 300 μm is obtained.

Figure 13:
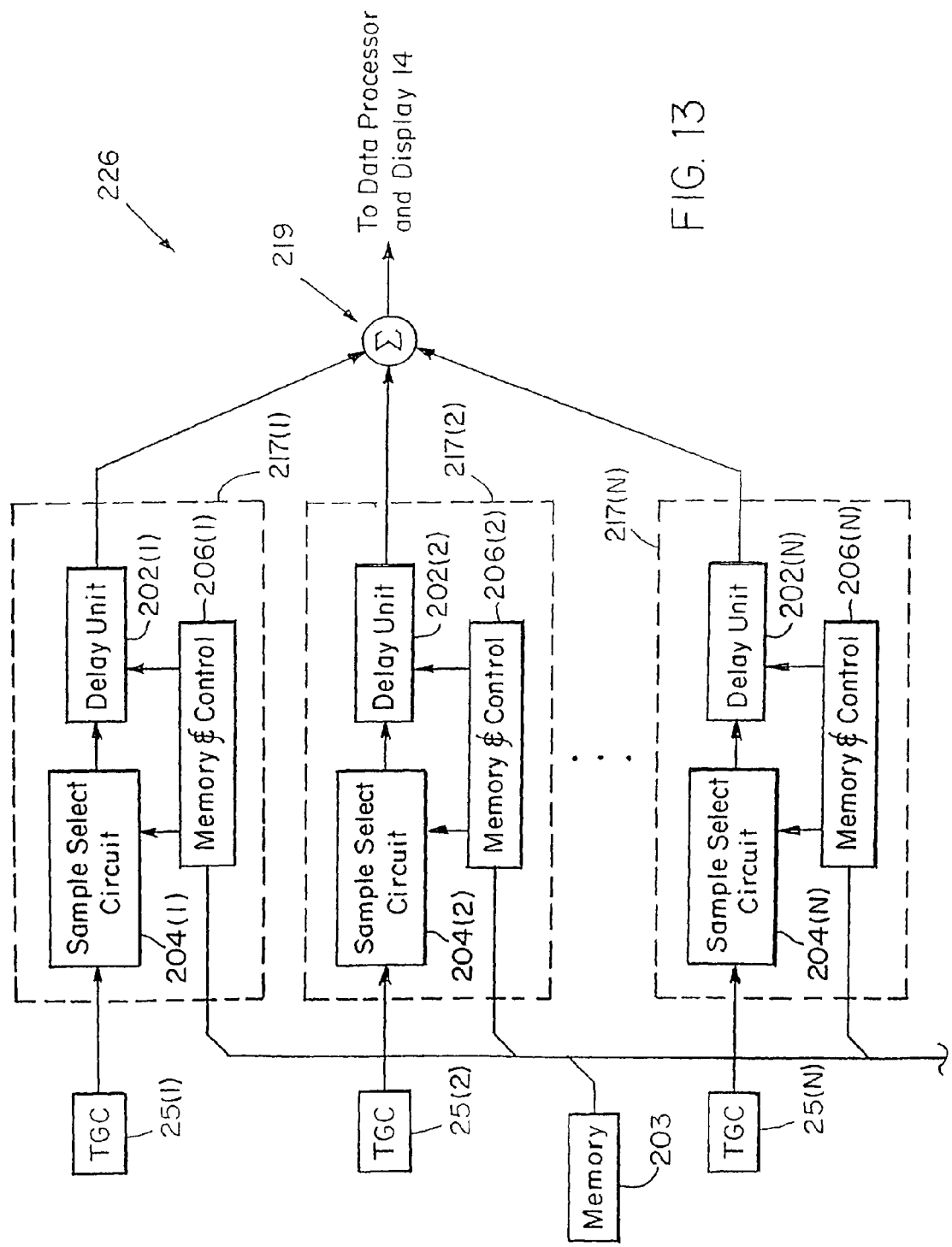
FIG. 13 shows a schematic block diagram of an alternative embodiment of an array of beam forming and focusing circuits in accordance with the present invention using a programmable sample selection circuit and a programmable delay unit.

FIG. 13 is a detailed block diagram of an alternative embodiment of the beam forming circuits of the invention to those of FIGS. 6 and 12. Referring to FIG. 13, the beam forming circuits 226 can be used for dynamic beam forming and scanning in the receive mode.

As shown in FIG. 13, the beam forming circuits 226 include N parallel processing channels 217(1)-217(N), one for each element 18 in the ultrasound transducer array (see FIG. 5). Each channel 217(1)-217(N) includes a respective delay unit 202(1)-202(N), a respective programmable input sampling circuit 204(1)-204(N), respective local memory and control circuitry 206(1)-206(N) for storing and generating proper timing for the sampling circuit 204(1)-204(N) and for storing and selecting the proper delay in the delay circuit 202(1)-202(N) for the sampled image data from the sampling circuit 204(1)-204(N).

The beam forming circuits 226 also include a central memory 203 which stores all of the delay values needed for all of the processing channels 217(1)-217(N). In one embodiment, for each scan line, the central memory 203 downloads delay data values to the memory and control circuits 206(1)-206(N) for all of the processing channels 217(1)-217(N). The delay values stored in each local memory 206(1)-206(N) are used to control the sample selection performed by each respective sample selection circuit 204(1)-204(N) and the sample delay effected by each respective programmable delay unit 202(1)-202(N). In one preferred embodiment, each imaging scan line requires a specific set of delays for all of the processing channels, such as in the case of phased array beam forming. In that embodiment, new delay value sets are downloaded to the local memories 206(1)-206(N) before each scan line is executed. Due to the compactness of each delay unit 202(1)-202(N) and the simplification of its corresponding sample and control circuits 204(1)-204(N) and 206(1)-206(N), this approach allows the beam forming electronics of a 128-element receiver array to all be integrated on a single chip.

The operation of the beam forming circuits 226 will now be described. Returned echoes received by a transducer 18(1)-18(N) are first amplified in a preamplification circuit 24(1)-24(N) and a TGC circuit 25(1)-25(N) (see FIG. 5) and then applied to the input of a corresponding respective sampling circuit 204(1)-204(N). The sampling rate, $f_s$, of this circuit 204(1)-204(N) is chosen to be higher than the clock rate $f_c$, of the corresponding delay unit 202(1)-202(N), i.e., in one clock period of the delay unit 202(1)-202(N), there are fife possible samples. In the present invention, one of these fife possible samples is selected and then loaded into the delay unit 202(1)-202(N). Thus, it will be recognized that uniformly or nonuniformly sampled data can be selected from the returned echoes and loaded into the delay unit 202(1)-202(N).

For example, if a sampling rate is eight times faster than that of the delay clock rate, $f_s=8f_c$, is chosen, eight sample data points are generated during each period of the delay line clock. The selection circuit 204(1)-204(N) is used to select one of the eight possible samples and to load it into the respective delay unit 202(1)-202(N). In addition, a control circuit is incorporated within each delay unit 202(1)-202(N) such that a programmable delay with a maximum delay of $M/f_c$ can be provided to each sampled data loaded into the delay unit, where M is the number of delay stages in a delay line of the delay unit 202(1)-202(N), as described below in connection with FIG. 15.

At each clock period of the delay unit clock, outputs from each processing channel 217(1)-217(N) are summed together in summing circuit 219 to provide a focused image point. The summed signal produced by the summing circuit 219 is forwarded to an A/D converter where it is digitized for transmission to the data processing and display device 14, or it can be forwarded in analog form directly to the processing and display device 14.

Figure 14A:
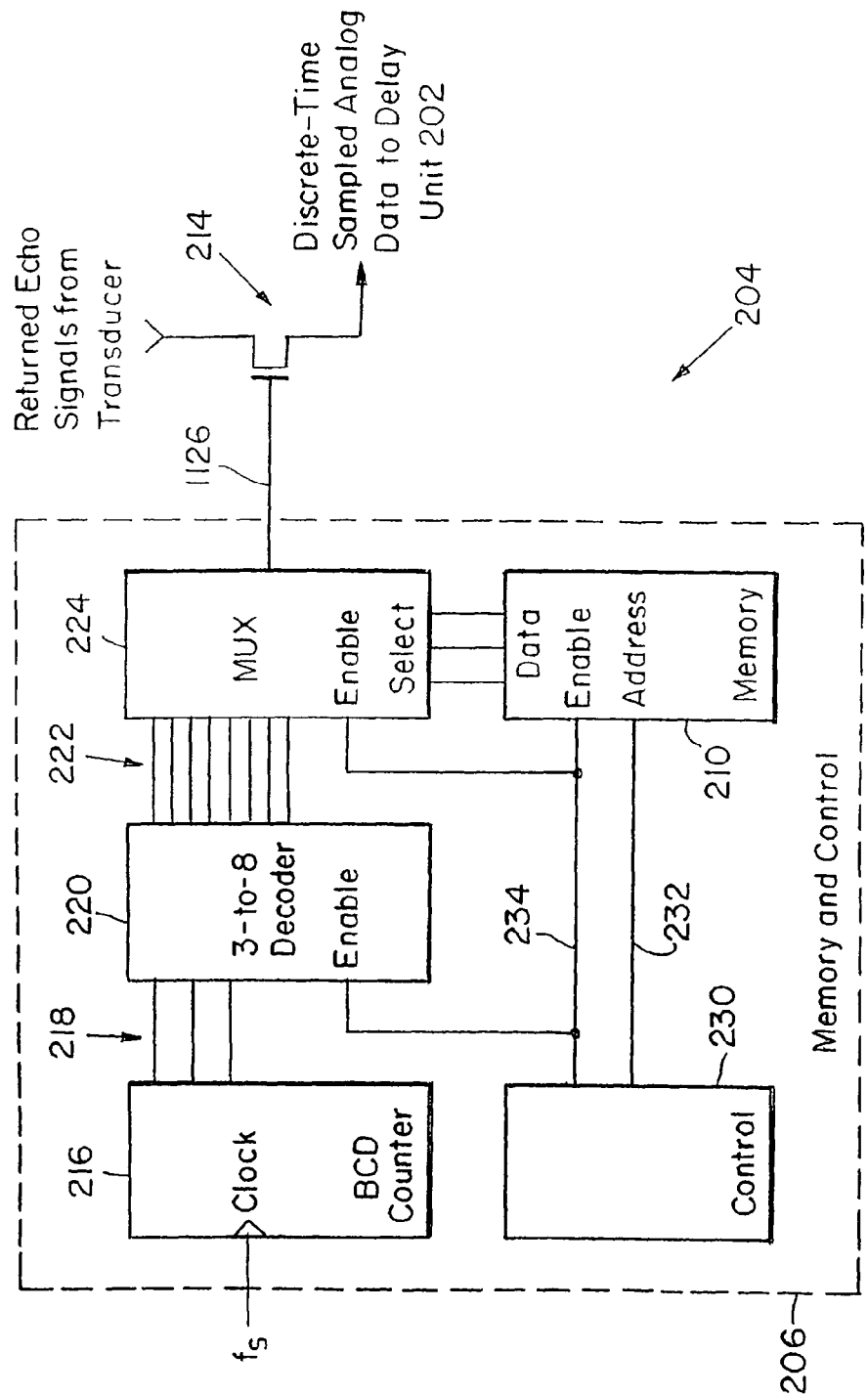
FIG. 14A shows a schematic diagram of an exemplary embodiment of a memory controlled programmable sample selection circuit used in accordance with the present invention.
Figure 14B:
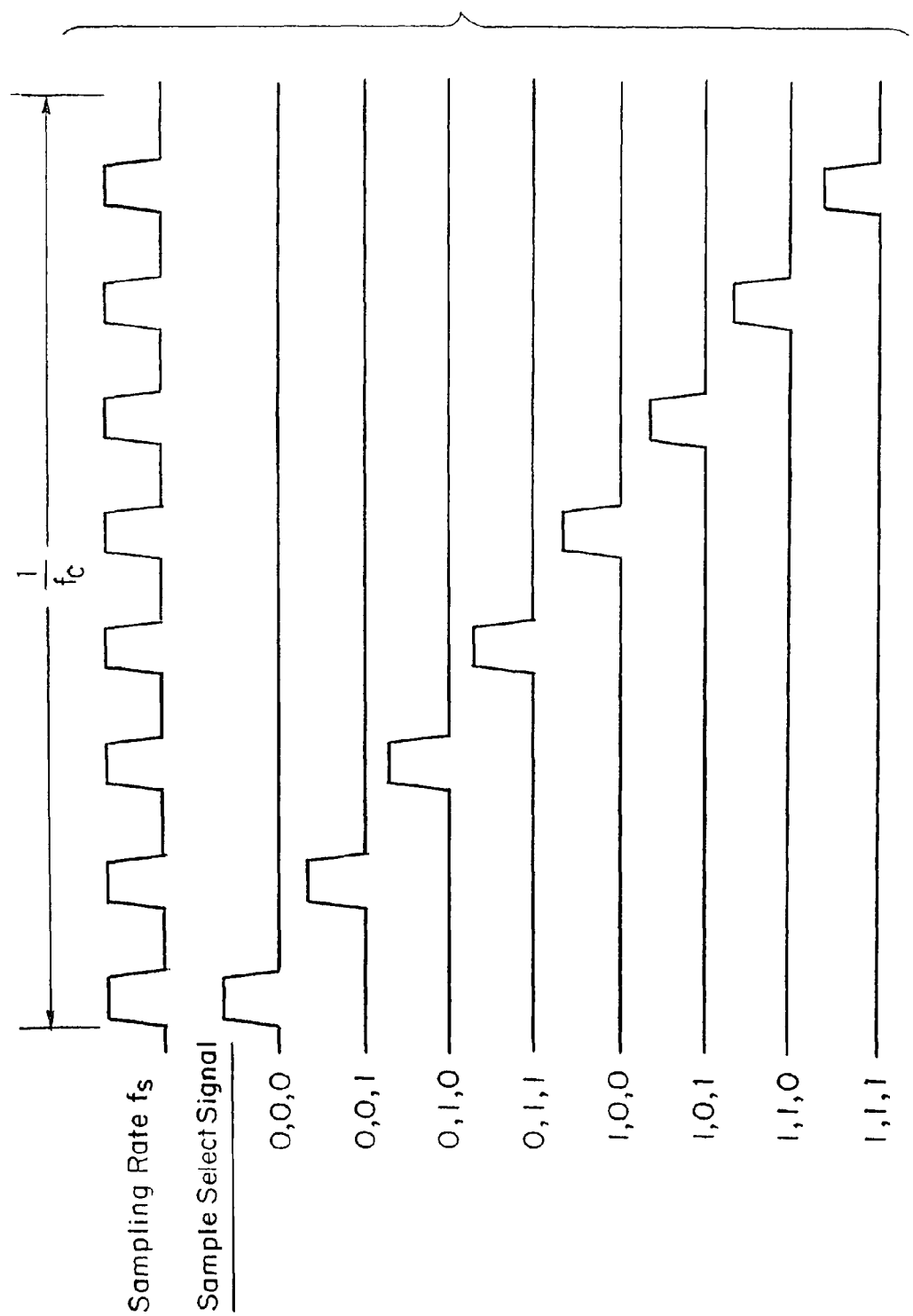
FIG. 14B contains timing diagrams for the sample selection circuit of FIG. 14A.

FIG. 14A is a schematic block diagram of an exemplary embodiment of a memory controlled programmable sample selection circuit 204 of the present invention, and FIG. 14B illustrates timing diagrams for the sampling process. In this example, the sampling rate $f_s$ is assumed to be eight times faster than the clock rate $f_c$ of the delay time 202, i.e., eight sample data items can be taken from the input waveform during a given clock period life of the delay line 202. In this configuration, eight evenly spaced timing windows are defined by the sampling frequency $f_s$ within the period of the delay clock life. Under control of the memory and control circuit 206, during each cycle of $f_c$, a single sample is taken during one of the timing windows.

The memory and control circuitry 206 includes a three-bit BCD counter 216 which is clocked to count at the sampling frequency $f_s$. The three outputs 218 from the counter 216 provide inputs to a 3-to-8 decoder 220, which provides a high-level output on one of its eight output lines 222 when enabled to indicate the decoded decimal value of the BCD inputs. An 8-to-1 MUX selects one of the decoder outputs to provide the sample select signal on line 1126 to the sampling NMOS transistor 214.

The line selected by the MUX 224 is controlled at its select lines by the three data outputs 228 of a memory 210. As shown in FIG. 14B, if the memory output word is (0,0,0), a single pulse is provided in the sample select signal on line 226 at the first sampling window. If the memory word is (0,0,1), the single pulse is provided at the second sampling window, and so forth. The gate of the NMOS transistor 214 is connected to the sample select signal. The drain is connected to the input waveform (returned echoes), and the source is connected to the delay line 202 to provide the sampled signal data.

The eight 3-bit selecting memory words are stored in addressable locations in the memory 210. During each cycle of the delay line clock, a location of the memory 210 is addressed via address lines 232 to output the selected 3-bit selection word on lines 228 according to the desired sampling window. The control circuitry 230 sets the address lines to the appropriate address according to the required sampling window location. Upon setting the address lines, the control circuitry 230 also sends out an enable signal on line 234 for every period of the delay clock to enable the outputs of the decoder 220, MUX 224 and memory 210 such that the pulse of the sample selection signal on line 1126 is located at the appropriate window. Since the control circuits 230 can select a memory address for every cycle of the delay, the spacing between samples can be precisely controlled to be uniform or nonuniform or have any desired pattern.

In one embodiment, the control circuits 230 include their own internal storage circuits which holds the sequence of addresses output by the control circuits 230 to generate the sample pulse during the appropriate timing windows. The address sequence is downloaded to the storage circuit from the central memory 230 of the beam forming circuits 226 before each scan line is executed. The storage circuit can be a memory such as a RAM, or it can be a shift register. In either case, the storage circuit is clocked at the delay line clock rate $f_c$ to output the address required to sample data during the correct timing window.

Figure 15:
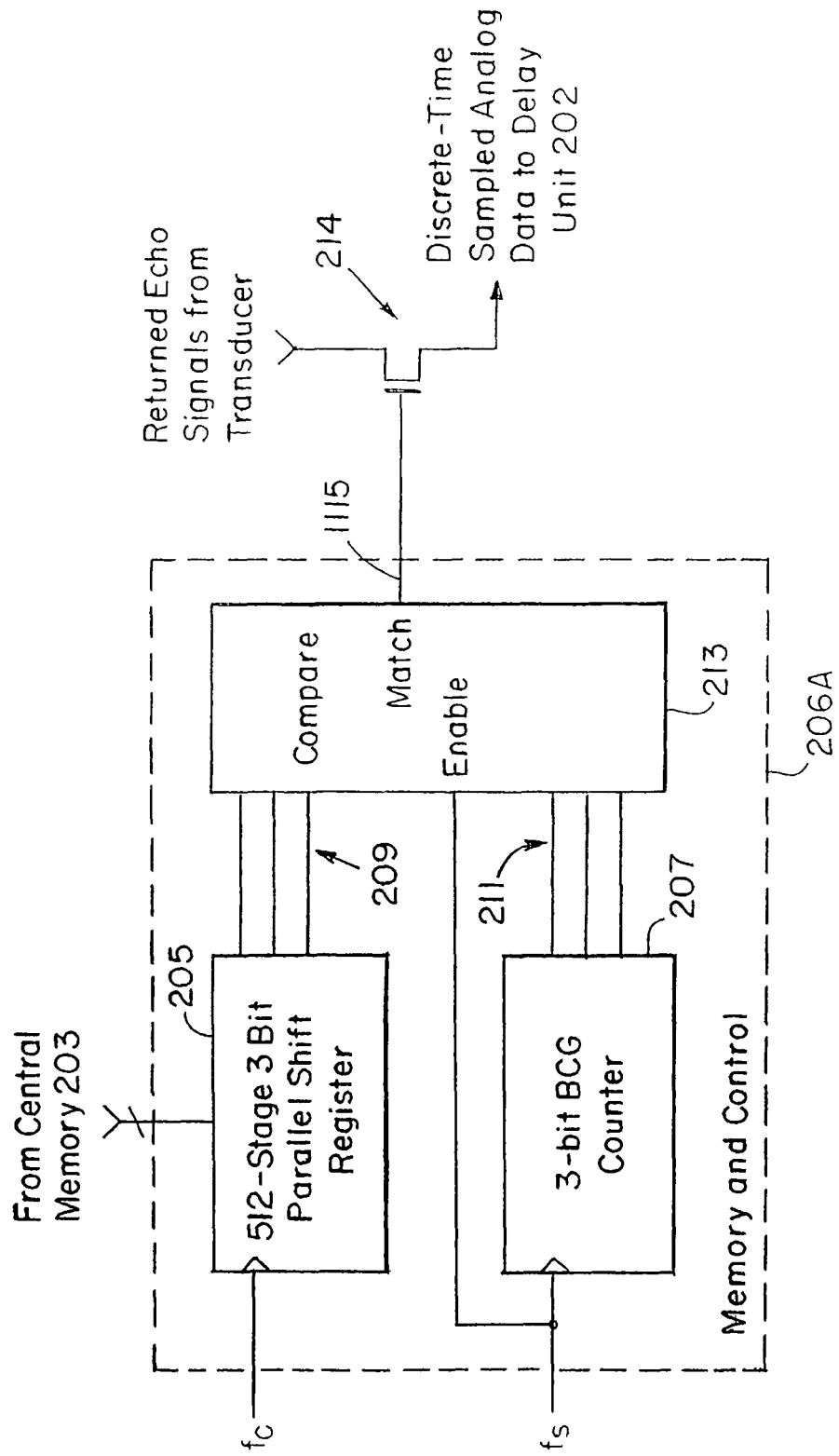
FIG. 15 is a schematic detailed block diagram of an alternative preferred embodiment of memory and control circuitry in accordance with the invention.

FIG. 15 is a detailed schematic block diagram of an alternative preferred form of the memory and control circuitry 206A to that shown in FIG. 14A. This alternative form of the memory and control circuit 206A includes a storage circuit such as shift register 205. In this embodiment, the shift register 205 shifts out a 3-bit pre-stored word on every cycle of the clock of the delay unit 202 at the delay unit clock rate $f_c$. The output words shifted out of the shift register 205 on output lines 209 are stored in the register 205 before each scan line is executed. The words are downloaded from the central memory 203 according to the delays which are to be used for the scan line. In one embodiment, the number of words stored in the shift register 205 for each scan line is equal to the number of focus points along each scan line. In one preferred embodiment, there are 512 focus points and, hence, 512 3-bit words. That is, the shift register 205 is a 512-stage 3-bit register.

The memory and control circuitry 206A also includes a 3-bit BCD counter 207 which is clocked at the selection sampling rate $f_s$. The counter 207 outputs 3-bit BCD words in sequence as it is clocked by the clock signal at the $f_s$ rate. In the example described above, the sampling rate $f_s$ is eight times the delay clock rate $f_c$; therefore, for each word on the output lines 209 of the shift register 205, the eight 3-bit BCD words $0_{10}$ through $7_{10}$ are output on the output lines 211.

The outputs 209 from the shift register 205 and the outputs 211 from the counter 207 are forwarded to a comparison circuit 213 which compares the two 3-bit words to determine if they are identical. When they are identical, a match is indicated by the comparison circuit 213 outputting a positive pulse on output line 1115. The pulse is applied to the sampling NMOS transistor 214 to sample the returned echo signals from the appropriate acoustic transducer 18. The discrete-time sampled analog data is forwarded to the appropriate corresponding delay unit 202.

The positive pulse on line 1115 occurs when one of the 3-bit BCD words from the counter 207 matches the 3-bit word from the shift register 205. This will occur during one of the eight possible timing windows into which the delay line clock rate $f_c$ is divided. Hence, the 3-bit word stored in the shift register 205 determines the window during which the returning echo data will be sampled. Therefore, to control the delays, a predetermined pattern of 3-bit words is stored in the shift register 205 before execution of the particular scan line by downloading from the central memory 203.

Figure 16:
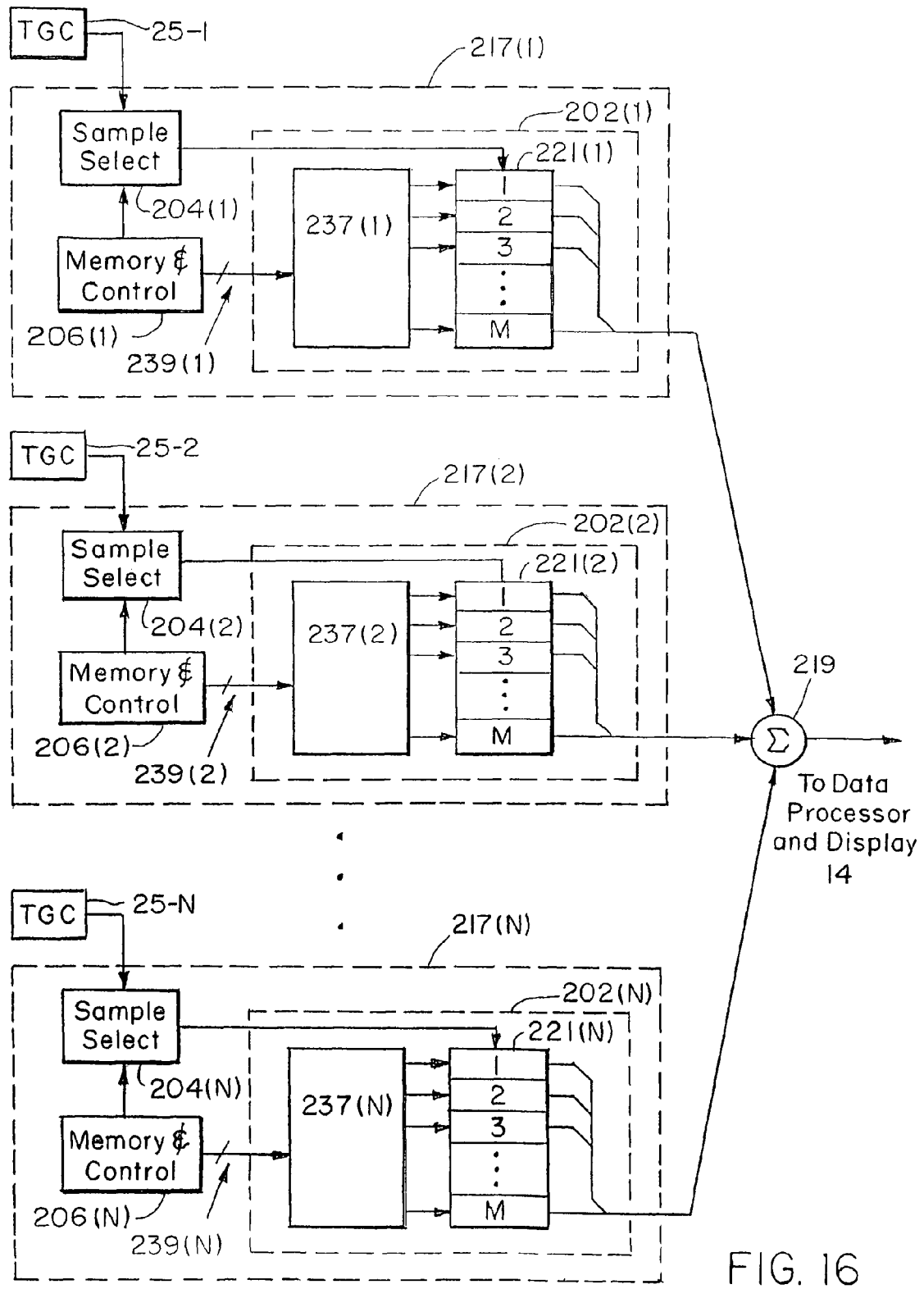
FIG. 16 shows a schematic block diagram of an embodiment of the beam forming circuits of FIG. 13, in which CCD programmable delay lines are employed.

FIG. 16 is a detailed schematic block diagram of a preferred embodiment of the processing channels 217(1)-217(N) of the beam forming circuits 226 of FIGS. 13-15, which shows the details one preferred embodiment of the programmable delay units 202(1)-202(N). In this embodiment, each delay unit 202(1)-202(N) includes an M-stage programmable tapped CCD delay line 221(1)-221(N). At each stage of delay, an output is provided; therefore, for each delay line 221(1)-221(N), there are M-parallel outputs.

In this embodiment, the tapping of each delay line 221(1)-221(N) is controlled by a digital parallel decoder 237(1)-237(N) with M outputs. One of the M selectable outputs is selected according to the decoded decimal value on the BCD input lines 239 from the memory and control circuit 206. For example, a 6-to-64 decoder 237(1)-237(N) can be used to provide an output selection for a 64-stage CCD delay line 221(1)-221(N). At every clock of the delay clock $f_c$, a discrete-time analog sample from the sample select circuit 204(1)-204(N) is delayed by the delay line 221(1)-221(N) and, hence, provided at the output of the stage selected by the decoder 237(1)-237(N). The delay time for each sampled data loaded into the delay line can be continuously changed to provide dynamic focusing. The sampled and delayed data from all channels 217(1)-217(N) is summed in summing circuit 219.

Figure 17:
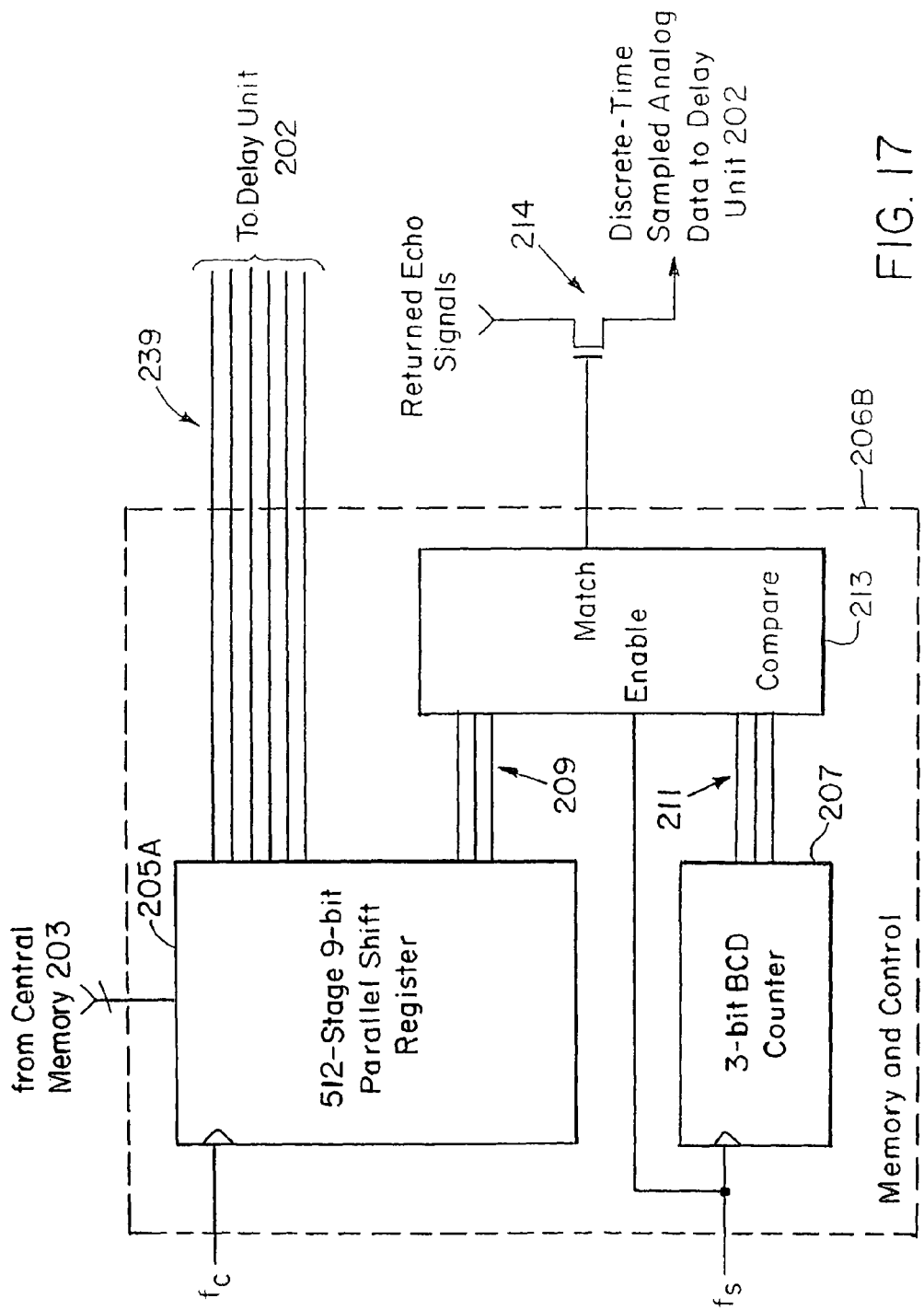
FIG. 17 is a schematic detailed block diagram of another alternative preferred embodiment of memory and control circuitry in accordance with the invention.

In FIG. 16, the input lines 239 to the decoder 237 are shown coming from the memory and control circuit 206. FIG. 17 is a detailed schematic block diagram of an embodiment of the memory and control circuit 206B which generates the decoder input lines 239. The circuit of FIG. 17 is identical to that of FIG. 15 except for the generation of the decoder input line signals 239. In FIG. 17, a preferred 512-stage 9-bit parallel shift register 205A is used in a fashion identical to that of the register 205 in FIG. 15 to generate the 3-bit word on lines 209 used in the comparison circuit 213 to generate the sampling pulse in the desired timing window. Preferably, a 6-bit word is also output simultaneously on lines 239 and forwarded to the delay unit 202. As described above, this 6-bit word is used as an input to the decoder 237 described above to select an appropriate stage of the tapped CCD delay line 221 to introduce the appropriate delay into the sampled signal.

As in the memory and control circuit 206A of FIG. 15, the sampling and delay control words are downloaded to the shift register 205A from the central memory 203 prior to the execution of each scan line. In the case of FIG. 17, where 512 focus points are implemented, 512 9-bit digital words are downloaded before the execution of each scan line. As the register 205A is clocked at the delay unit clock rate $f_c$, 9-bit digital words are output in succession on lines 239 and 209, one 9-bit word at a time. The 3-bit word on lines 209 controls the timing window during which the returned echoes are sampled, and the 6-bit word on lines 239 controls the amount of delay introduced into the sample by the programmable delay unit 202.

Figure 18:
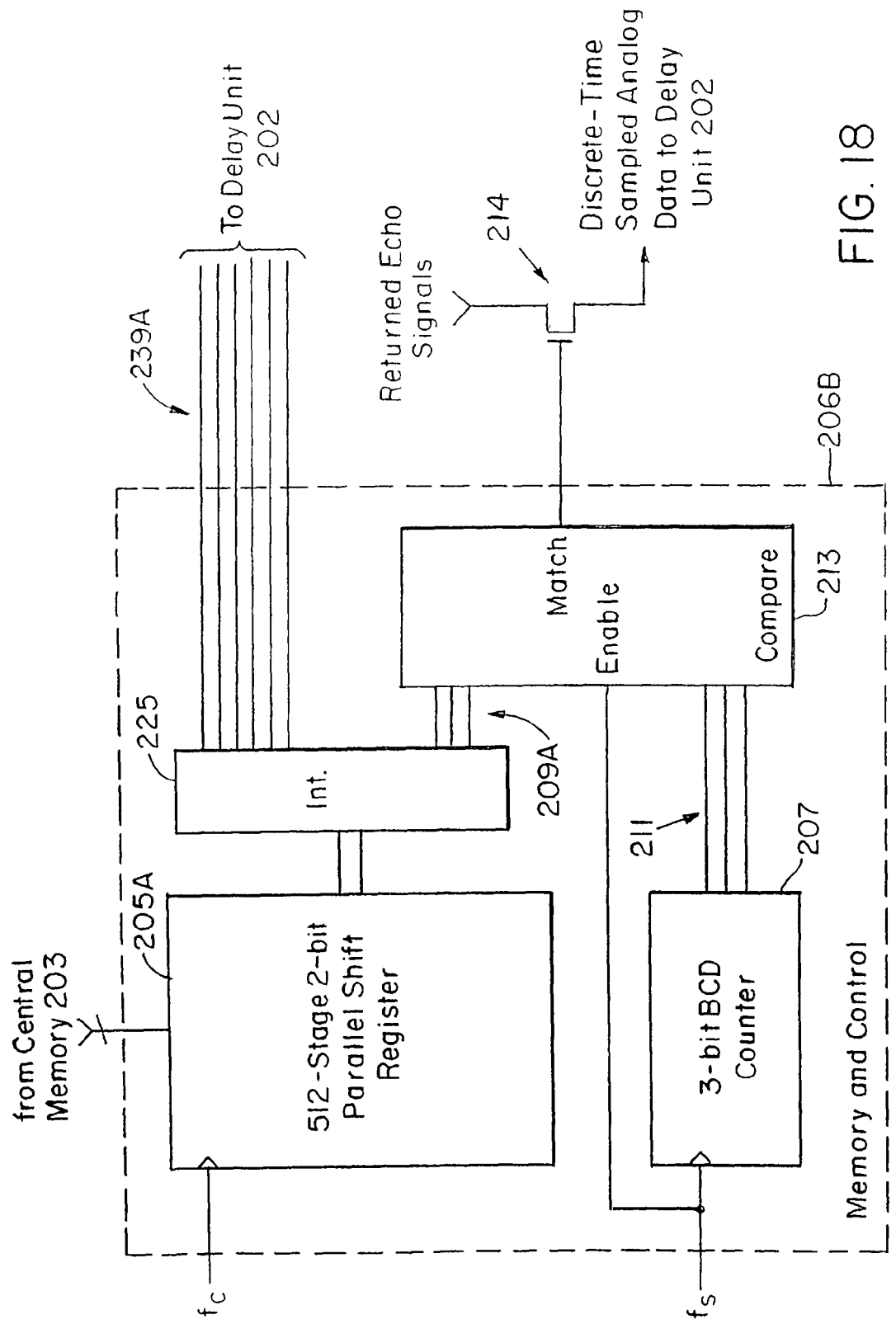
FIG. 18 is a schematic detailed block diagram of another alternative preferred embodiment of memory and control circuitry in accordance with the invention.

FIG. 18 is a detailed block diagram of a variation on the circuit shown in FIG. 17. The alternative memory and control circuit 206C of FIG. 18 reduces the amount of memory space needed in the circuit 206C. Instead of storing 512 9-bit words, 2-bit words can be used. In this embodiment, instead of storing the actual absolute delays for each focus point, the difference between adjacent delays and/or the second difference between the first differences is stored. In the case where the second difference is stored, only two bits are required to store the required delay information. Hence, only 2-bit words need be downloaded from the central memory 203 and stored by the shift register 205B. In this case, the 512-stage shift register is only two bits wide.

Once again, the register 205B is clocked at the rate of the delay clock $f_c$. The 2 bit word is output by the register 205B to an integration circuit 225 which can include a dual-stage adder circuit used to recover the actual delays from the stored first and second difference. The integration step generates a 6-bit word on lines 239A, which is used as the control inputs to the decoder 237 in the programmable delay unit 202. The three additional bits generated on lines 209A are used as described above in the comparison circuit 213 to generate a sampling pulse at the appropriate timing window.

Figure 19:
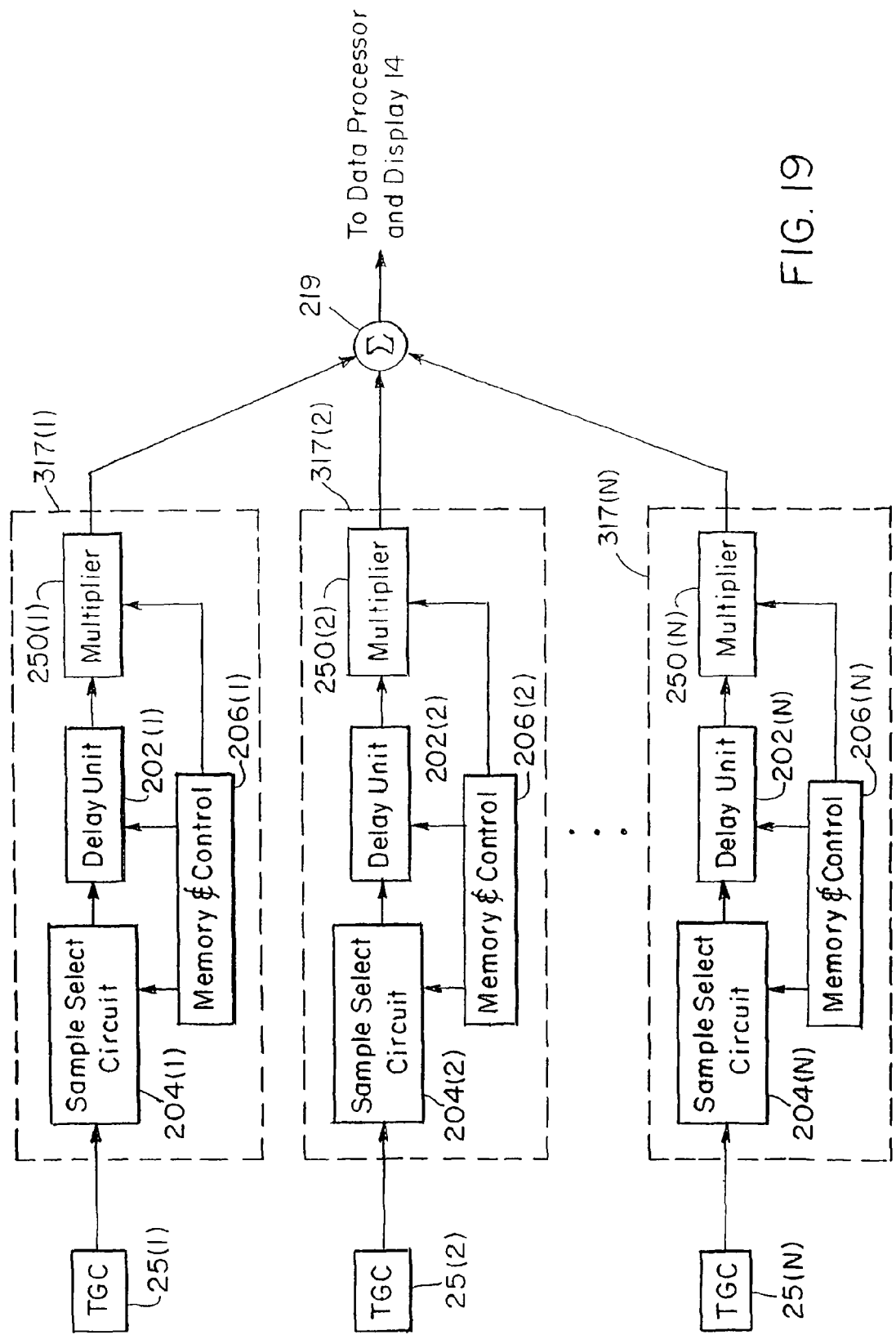
FIG. 19 shows a block diagram of an alternative embodiment of the present invention in which the selected outputs of each of the beam forming and focusing circuits are applied to respective multiplier weighting circuits.
Figure 20:
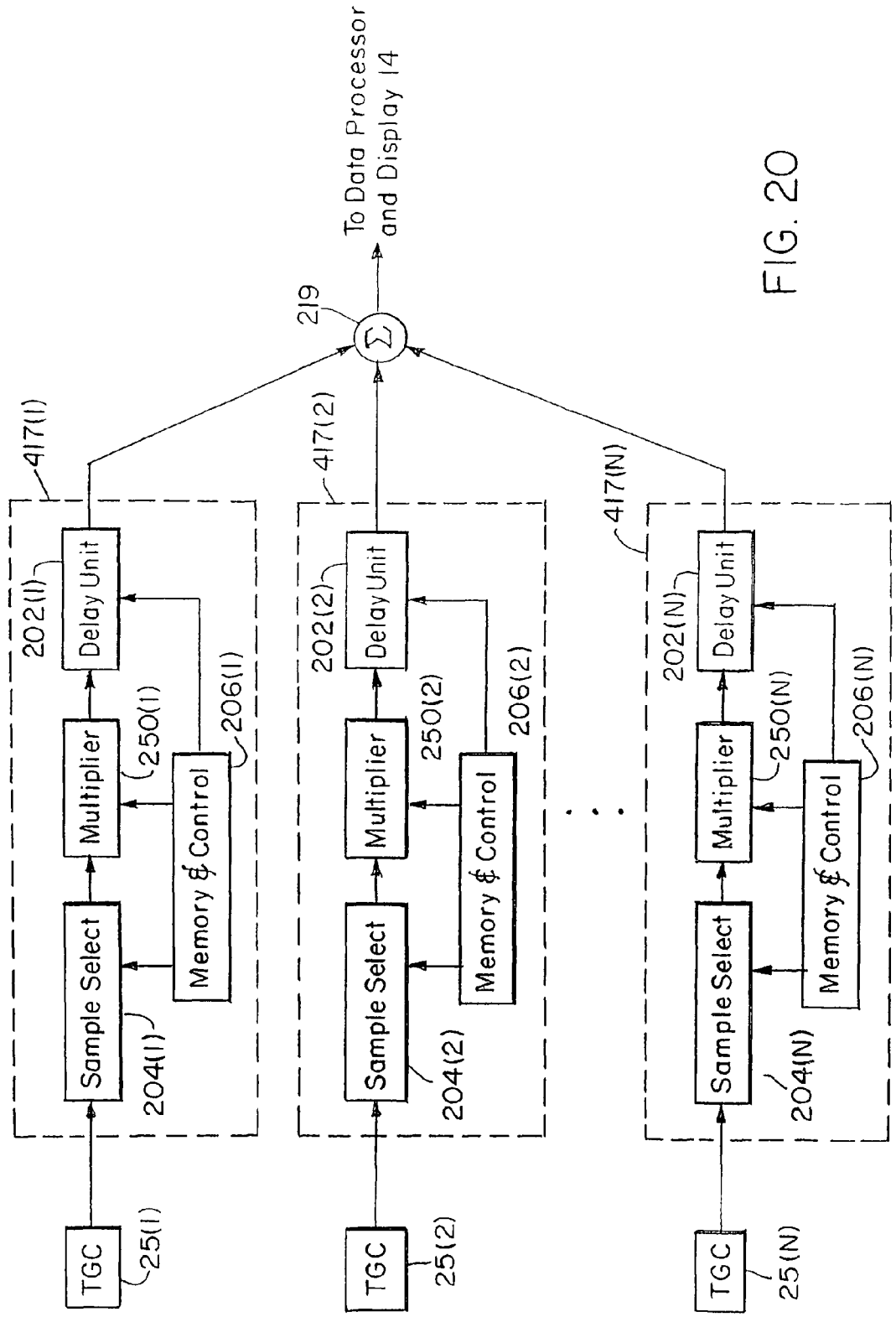
FIG. 20 shows a block diagram of an alternative embodiment of the present invention in which the multiplier weighting circuit is placed to the input of the delay unit.

Another embodiment of the delay processing circuitry is shown in FIG. 19. FIG. 19 is a schematic block diagram of a modification of the circuitry of FIG. 13 in which a multiplier 250(1)-250(N) is included at the output of each programmable delay unit 202(1)-202(N). This implementation allows the use of apodization, such as by incorporating a Hamming weighting at the receiver array to reduce the sidelobe level and generate better quality imagery. The weighting function of the multiplicand of each multiplier is provided by an on-chip buffer memory contained in memory and control circuits 206(1)-206(N). The outputs of all the multipliers 250(1)-250(N) are summed together at summing circuit 219 to form a beam output. It is important to note the apodization can be performed either at the input or at the output of the delay unit 202(1)-202(N). In FIG. 20, an input weighted delay structure is shown.

Figure 21:
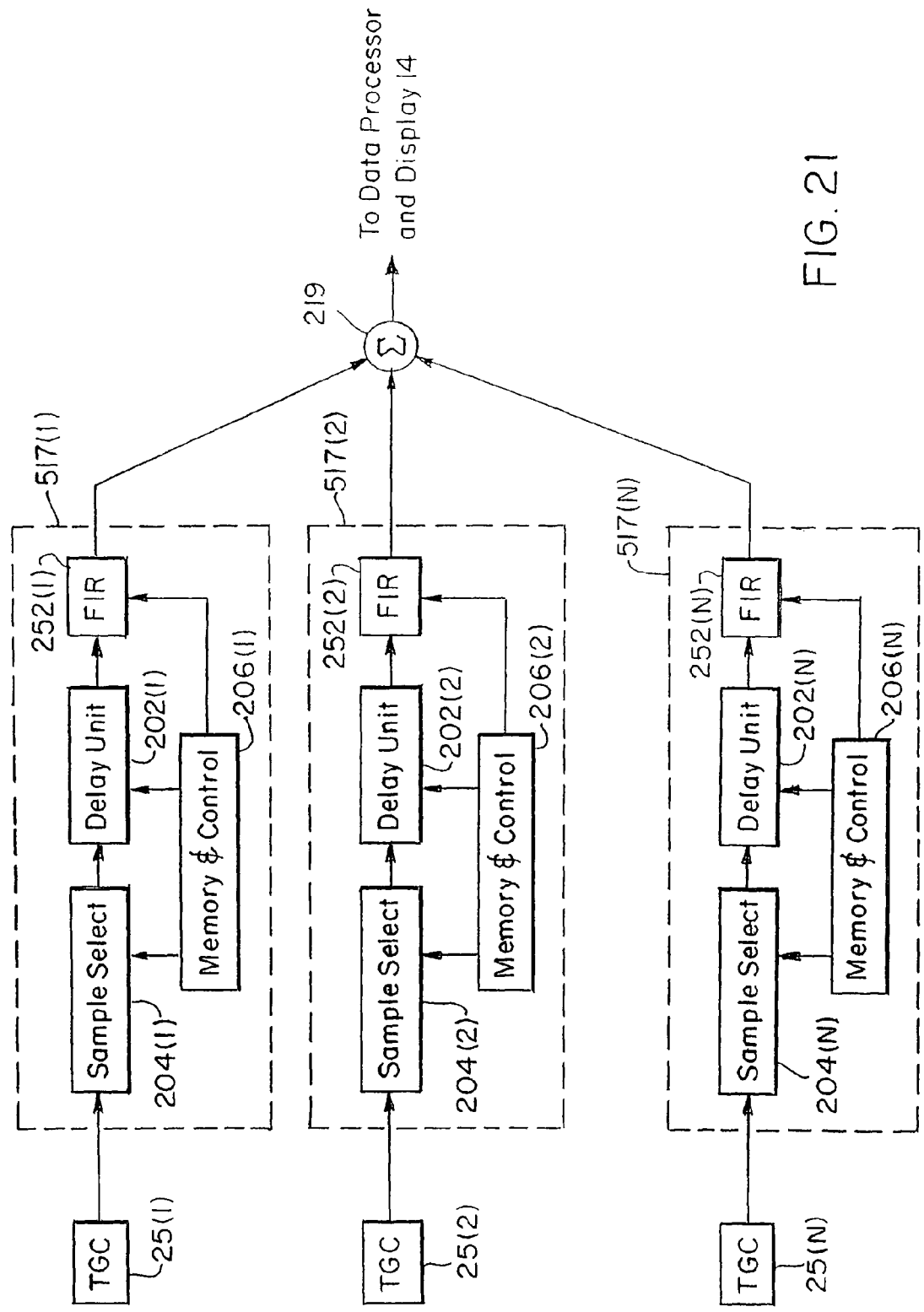
FIG. 21 shows a block diagram of an alternative implementation of the present invention, in which a finite-impulse response (FIR) filter for time-domain interpolation is placed following the delay units.

In all the implementations described above in connection with FIGS. 13-20, the minimum delay resolution is determined by the sampling rate $f_s$. Another implementation which provides an effective delay time smaller than $t_c$ is shown in FIG. 21. As can be seen in FIG. 21, a finite-impulse-response (FIR) filter 252(1)-252(N) is added to the output of the programmable delay circuit 202(1)-202(N). The FIR filter 252(1)-252(N) can be used to generate time-domain interpolated image samples and effectively achieve delay resolution smaller than $t_c$. For example, if four interpolated samples are generated by the FIR filter 252(1)-252(N), the delay resolution is then t/4.

Figure 22:
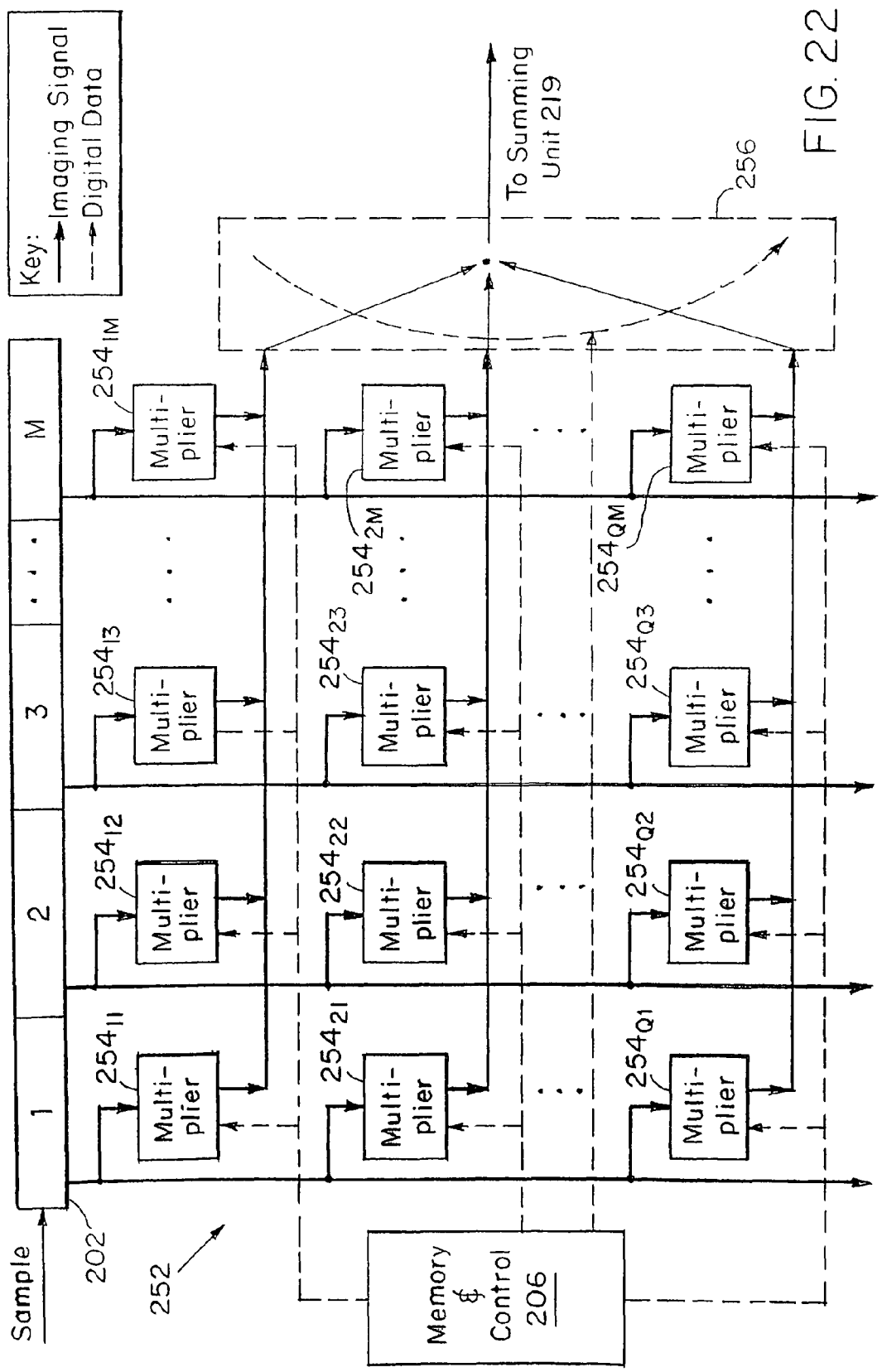
FIG. 22 shows a block diagram of a FIR filter implementation in which fixed weight multipliers are used for input sample interpolation.

FIG. 22 contains a detailed schematic block diagram of one exemplary embodiment of an interpolation FIR filter 252 in accordance with the invention with fixed-weighted multipliers 254. In general, a multiplier requires two inputs, and the output of a multiplier is the product of the two inputs. In a fixed-weight multiplier 254, however, the multiplicand is fixed and only one input is needed. Its output is the input multiplied by the same multiplicand.

An M-stage delay line 202 is used to hold and shift sampled and delayed returned echoes. At each stage of delay, there is a bank of Q fixed-weight multipliers 254, i.e., there are M×Q multipliers 254. Thus, as shown in FIG. 22, the multipliers 254 can be viewed as forming a two-dimensional array having Q rows and M columns. Each multiplier $254_{ij}$ can be identified by a coordinate i,j, where i is the row of multipliers and j is the delay stage of the delay line 202, or column of the array.

As can be seen in FIG. 22, all the multipliers 254 on the same column share a common input, which corresponds to one of the input samples. All the multipliers 254 on the same row share a common output, which corresponds to one of the interpolated samples. It follows then, at every clock, there are Q interpolated samples. A sample select circuit 256 can be placed at the parallel output ports to select one of the interpolated samples and then applies it to the summing unit 219.

Figure 23:
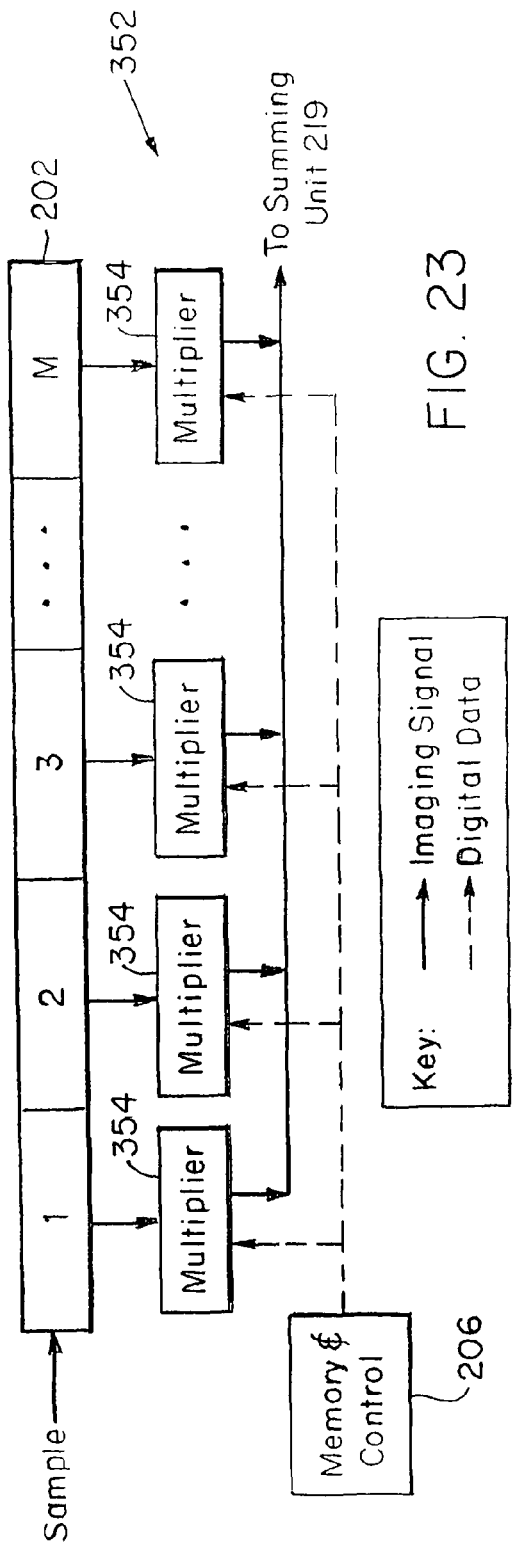
FIG. 23 shows a block diagram of an alternative FIR filter implementation in which programmable multipliers are used for input sample interpolation.

FIG. 23 shows the schematic block diagram of another exemplary embodiment of the interpolation FIR filter 352 with programmable multipliers 354. Again, an M stage delay line 202 is used to hold and shift sampled and delayed returned echoes. At each stage of delay, there is a programmable multiplier 354b where k=1, 2, . . . , M. As can be seen in FIG. 20, all the multipliers $354_k$ share a common output which corresponds to the interpolated sample of the inputs. Time-domain interpolated samples can be generated based on the programmed weights.

As described above, the ultrasound signal is received and digitized in its natural polar (r,θ) form. For display, this representation is inconvenient, so it is converted into a rectangular (x,y) representation for further processing. The rectangular representation is digitally corrected for the dynamic range and brightness of various displays and hardcopy devices. The data can also be stored and retrieved for redisplay. In making the conversion between polar and rectangular coordinates, the (x,y) values must be computed from the (r,θ) values since the points on the (r,θ) array and the rectangular (x,y) grid are not coincident.

In prior scan conversion systems, each point on the (x,y) grid is visited and its value is computed from the values of the four nearest neighbors on the (r,θ) array by simple linear interpolation. This is accomplished by use of a finite state machine to generate the (x,y) traversal pattern, a bidirectional shift register to hold the (r,θ) data samples in a large number of digital logic and memory units to control the process and ensure that the correct asynchronously received samples of (r,θ) data arrive for interpolation at the right time for each (x,y) point. This prior implementation can be both inflexible and unnecessarily complex. Despite the extensive control hardware, only a single path through the (x,y) array is possible. This means that full advantage of different ultrasound scan frequencies and, hence, imaging depths, cannot be taken. That is, different data are forced into the same format regardless of physical reality.

In the scan conversion circuitry 28 of the present invention (see FIG. 4), hardware complexity and cost are drastically reduced through the use of a number theoretic scheme for reliably generating the (x,y) grid traversal path in natural order, i.e., using the (r,θ) samples as they are acquired. This approach provides greater flexibility and better fidelity to the actual medical data, as it permits the array traversals to be designed so that they do not impose an unnatural image reconstruction scheme. This scan conversion circuitry 28 of the present invention uses a Farey-sequence generator process, which generates the (x,y) coordinates in the order in which they are encountered in the scanning.

Assume that the system received the first two scan rays; it is desired to identify all the (x,y) integer pairs situated within the wedge for 0<y≦L. A process which uses a Farey sequences to generate all (x,y) pairs within two successive arrays with 0<y≦L in the order of increasing angle is described here. The process exploits the fact that certain (x,y) pairs lie along the same angle, so it generates only (a,b) pairs which are mutually prime and then sets the rest of (x,y) pairs by (x,y)=n(a,b) for n=1, 2, . . . until (n+1) b>L. To better understand how this is accomplished, let us define a Farey sequence.

Definition: The sequence of rational numbers whose denominator does not exceed L, arranged in increasing numerical order, is called the Farey sequence of order L.

If u/v is a fraction in lowest terms and v≦L, we will call u/v a Farey fraction of order L. Therefore, Farey fraction is in lowest terms; thus, its numerator and denominator are mutually prime. The theory of Farey series is described in detail in G. H. Hardy and E. M. Wright, *An Introduction to the Theory of Numbers*, Oxford University Press, London 1938, pp. 23-24, which is incorporated herein by reference.

Of relevance to the present invention is the following relationship. Let a/b, c/d, e/f be three successive Farey fractions of order L and let $$Z = \left[\frac{L+b}{d}\right], \text{ where } [\ ] = \text{greatest integer function} \quad (1)$$

$$e = Zc - a, \, f = Cd - b. \quad (2)$$

Equations 1 and 2 permit us to begin with any two successive Farey fractions and iterate through all the rest within the slice.

Figure 24:
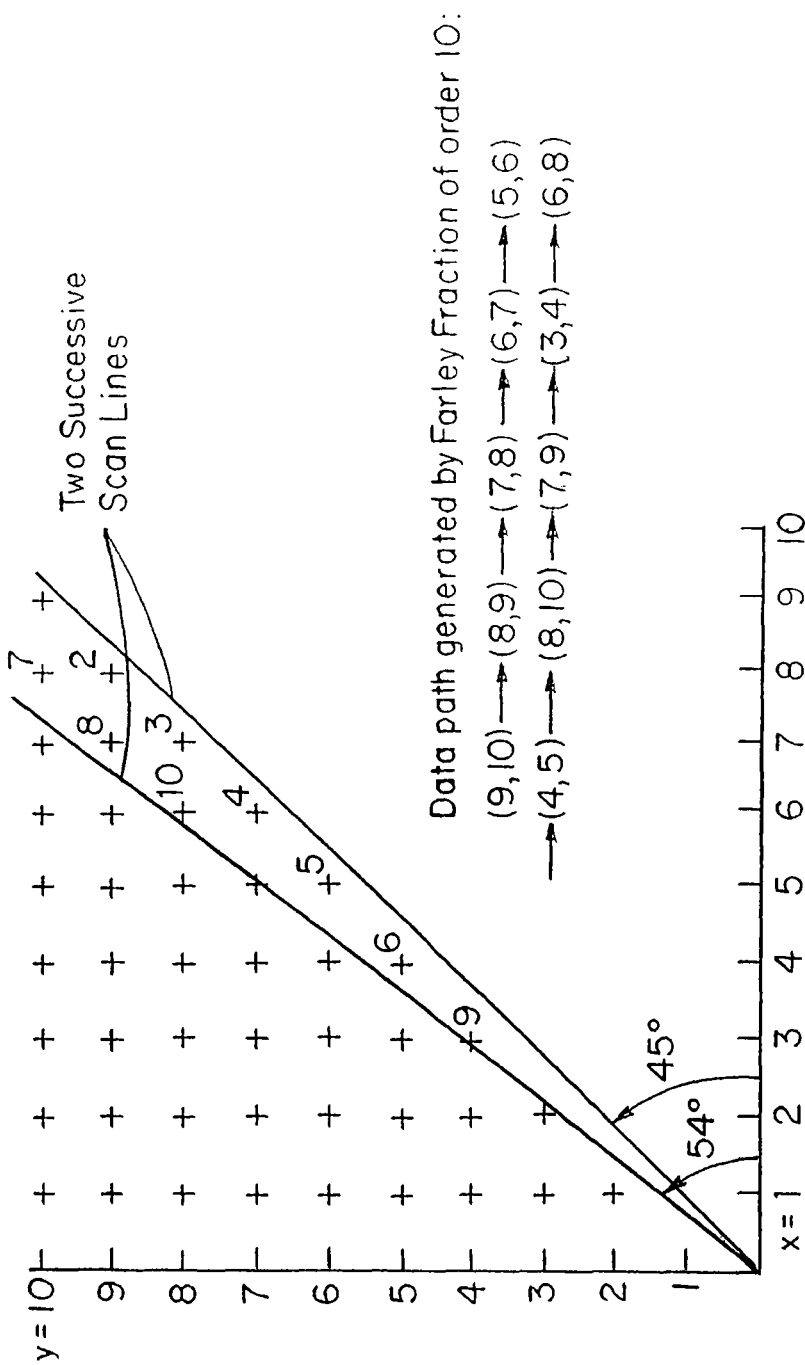
FIG. 24 is a schematic diagram showing the scan conversion process of the invention.

A simple example of using Farey fractions of order 10 to generate all the (x,y) display points within the 46°-54° arc on a 10×10 grid is shown in FIG. 24. Substituting the values for the first two successive Farey fractions of the order L=10, a=1, b=1, and c=L−1=9, d=L=10 into Equations 1 and 2, one obtains the next Farey fraction with e=8, f=9. Now, repeating the same calculation with a=9, b=10, and c=8, d=9, yields the next Farey fractions with e=7, f=8. It is straightforward to generate all the (x,y) pairs within the given arc. If the user wants to map the same rays into a finer display grid (for example, onto a 20×20 display points), we use the same routine but with L=20 i.e., use the Farey function of order 20 to generate all the (x,y) display points. Simple arithmetic will show that the (x,y)-pairs are (19,20), (18,19), (17,18) . . . . As can be seen in FIG. 21, all the grid points within the two successive scan lines are generated in natural order of increasing angle, i.e., $$\operatorname{atan}\frac{10}{9} \langle \operatorname{atan}\frac{9}{8} \langle \operatorname{atan}\frac{8}{7} \langle \operatorname{atan}\frac{7}{6} \langle \operatorname{atan}\frac{6}{5} \langle \operatorname{atan}\frac{5}{4} \langle \operatorname{atan}\frac{9}{7} \langle \operatorname{atan}\frac{4}{3}$$

This characteristic allows a scan conversion system that automatically adapts to variation in scan angle Φo. Systems with programmable, non-uniformly spaced scan arrays are possible with the Farey sequence implementation. In one embodiment of the invention, the data processing and display unit 14 is programmed to carry out the scan conversion process.

As mentioned above, the ultrasound imaging system 10 of the present invention also includes a continuous or pulsed Doppler processor 36 which allows for generation of color flow maps. Thus, moving targets (particularly flowing blood) can be displayed, letting physicians see the body's inner functions without surgery.

Figure 25:
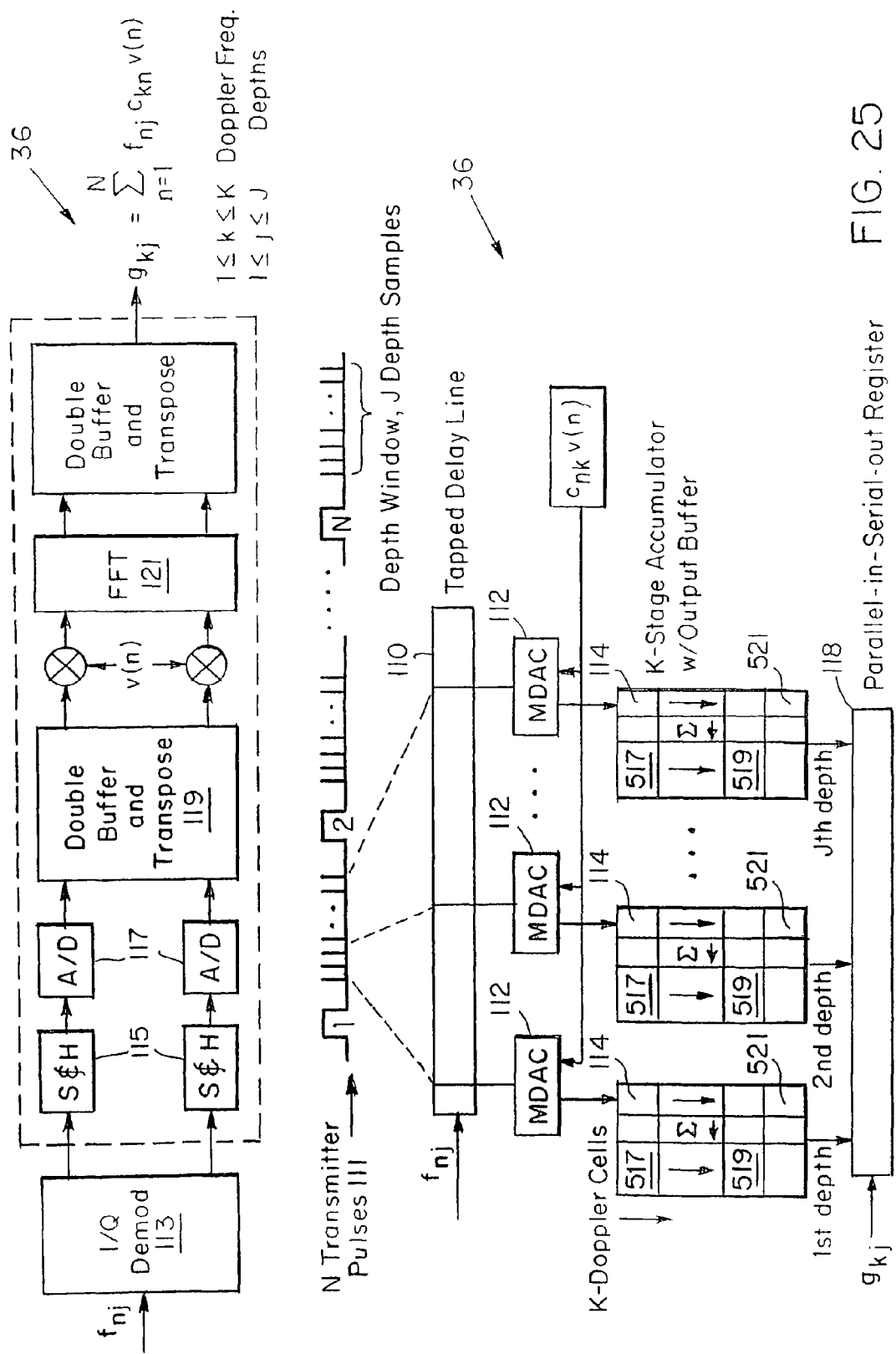
FIG. 25 is a schematic functional block diagram of a pulsed Doppler processing unit in accordance with the present invention.

The generic waveform 111 for pulsed Doppler ultrasound imaging is shown in FIG. 25. The waveform consists of a burst of N pulses with as many as J depth samples collected for each pulse in the burst. FIG. 25 also shows a block diagram of the pulsed Doppler signal processor 36 for this imaging technique, where the returned echoes received by each transducer are sampled and coherently summed prior to in-phase and quadrature demodulation at 113. The demodulated returns are converted to a digital representation at sample-and-hold circuits 115 and A/D converters 117, and then stored in a buffer memory 119 until all the pulse returns comprising a coherent interval are received. The N pulse returns collected for each depth are then read from memory, a weighting sequence, v(n), is applied to control Doppler sidelobes, and a N-point FFT is computed at 121. During the time the depth samples from one coherent interval are being processed through the Doppler filter, returns from the next coherent interval are arriving and are stored in a second input buffer.

The integrated Doppler processing device described herein performs all of the functions indicated in the dotted box of FIG. 25, except for A/D conversion, which is not necessary because the device provides the analog sampled data function. The remaining circuitry and the operation thereof is described in U.S. Pat. No. 4,464,726 to Alice M. Chiang, issued Aug. 7, 1984, entitled "Charge Domain Parallel Processing Network," which is incorporated herein by reference. This pulsed-Doppler processor (PDP) device has the capability to compute a matrix-matrix product, and therefore has a broad range of capabilities. The device computes the product of two real valued matrices by summing the outer products formed by pairing columns of the first matrix with corresponding rows of the second matrix.

In order to describe the application of the PDP to the Doppler filtering problem, we first cast the Doppler filtering equation into a sum of real-valued matrix operations. The Doppler filtering is accomplished by computing a Discrete Fourier Transform (DFT) of the weighted pulse returns for each depth of interest. If we denote the depth Doppler samples g(k,j), where k is the Doppler index, $0 \leq k \leq N-1$, and j is the depth index, then $$g(k, j) = \sum_{n=0}^{N-1} v(n) f(n, j) \exp(-j2\pi k n / N) \quad (3)$$

The weighting function can be combined with the DFT kernel to obtain a matrix of Doppler filter transform coefficients with elements given by $$w(k,n) = w n = v(n) \exp(-j2\pi k n / N) \quad (4)$$

The real and imaginary components of the Doppler filtered signal can now be written as $$g_{r,kj} = \sum_{n=0}^{N-1} (w_{r,kn} f_{r,nj} - w_{i,kn} f_{i,nj}) \quad (5)$$

$$g_{r,kj} = \sum_{n=0}^{N-1} (w_{r,kn} f_{r,nj} + w_{i,kn} f_{i,nj}) \quad (6)$$

In equations 5 and 6, the indices of the double-indexed variables may all be viewed as matrix indices. Therefore, in matrix representation, the Doppler filtering can be expressed as matrix product operation. It can be seen that the PDP device can be used to perform each of the four matrix multiplications thereby implementing the Doppler filtering operation.

The PDP device 36 of the invention includes a J-stage CCD tapped delay line 110, J CCD multiplying D/A converters (MDACs) 112, J×K accumulators 114, J×K Doppler sample buffer 517, and a parallel-in-serial out (PISO) output shift register 118. The MDACs share a common 8-bit digital input on which elements from the coefficient matrix are supplied. The tapped delay line 110 performs the function of a sample-and-hold converting the continuous-time analog input signal to a sampled analog signal.

In operation, the device 36 functions as follows: either the real or imaginary component of the returned echo is applied to the input of the tapped delay line 110. At the start of the depth window, the video is sampled at the appropriate rate and the successive depth samples are shifted into the tapped delay line 110. Once the depth samples from the first pulse return interval (PRI) are loaded, each element in the first column of the transform coefficient matrix W is sequentially applied to the common input of the MDACs 112. The products formed at the output of each MDAC 112 are loaded into a serial-in-parallel-out (SIPO) shift register 521. The collection of J×K products computed in this fashion represent an outer product matrix. These products are transferred from the SIPOs to CCD summing wells which will accumulate the outer product elements from subsequent PRIs. The process is repeated until all pulse returns (rows of F) have been processed.

At this point, each group of K accumulators 114 holds the K Doppler samples for a specific depth cell. The Doppler samples are simultaneously clocked into the accumulator output PISO shift registers 519. These registers act as a buffer to hold the J×K depth-Doppler samples, so processing can immediately begin on the next coherent interval of data. Finally, the accumulator shift registers 521 are clocked in parallel transferring all the depth samples for a given Doppler cell into the device output PISO shift register 118. Samples are serially read out of the PDP device in range order, which is the desired order for flow-map display.

A prototype PDP-A device for 16-depth samples has been fabricated. The PDPA can be used to process returns of a burst waveform with as many as 16 range samples collected for each pulse in the burst. The capability of detecting weak moving targets in the presence of a strong DC clutter has been successfully demonstrated by the prototype PDP device.

Figure 26:
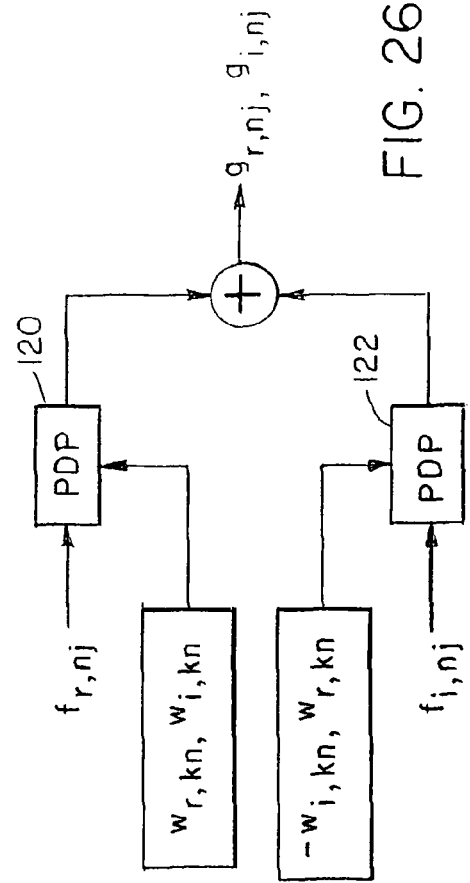
FIG. 26 is a schematic block diagram of a color flow map chip implementation using dual pulsed Doppler processors in accordance with the present invention.

A two-PDP implementation for color flow mapping in an ultrasound imaging system is shown in FIG. 26. In this device, during one PRI the top PDP component 120 computes all the terms of the form $w_r f_r$ and $w_i f_r$ as shown in equations 5 and 6, while the bottom component 122 computes terms of the form $-w_r f_r$ and $w_i f_r$. The outputs of each component are then summed to alternately obtain $g_r$ and $g_j$. As mentioned above, the imaging system of the invention also includes video compression circuitry 34 which conditions the data and transforms it into a compressed format to permit it to be transferred to a remote location. In a preferred embodiment, the video data compression circuitry is of the type described in U.S. Pat. Nos. 5,126,962 to Alice M. Chiang, issued Jun. 30, 1992, entitled "Discrete Cosine Transform Processing System," and 5,030,953 to Alice M. Chiang, issued Jul. 9, 1991, entitled "Charge Domain Block Matching Processor," both of which are incorporated herein by reference.

Figure 27:
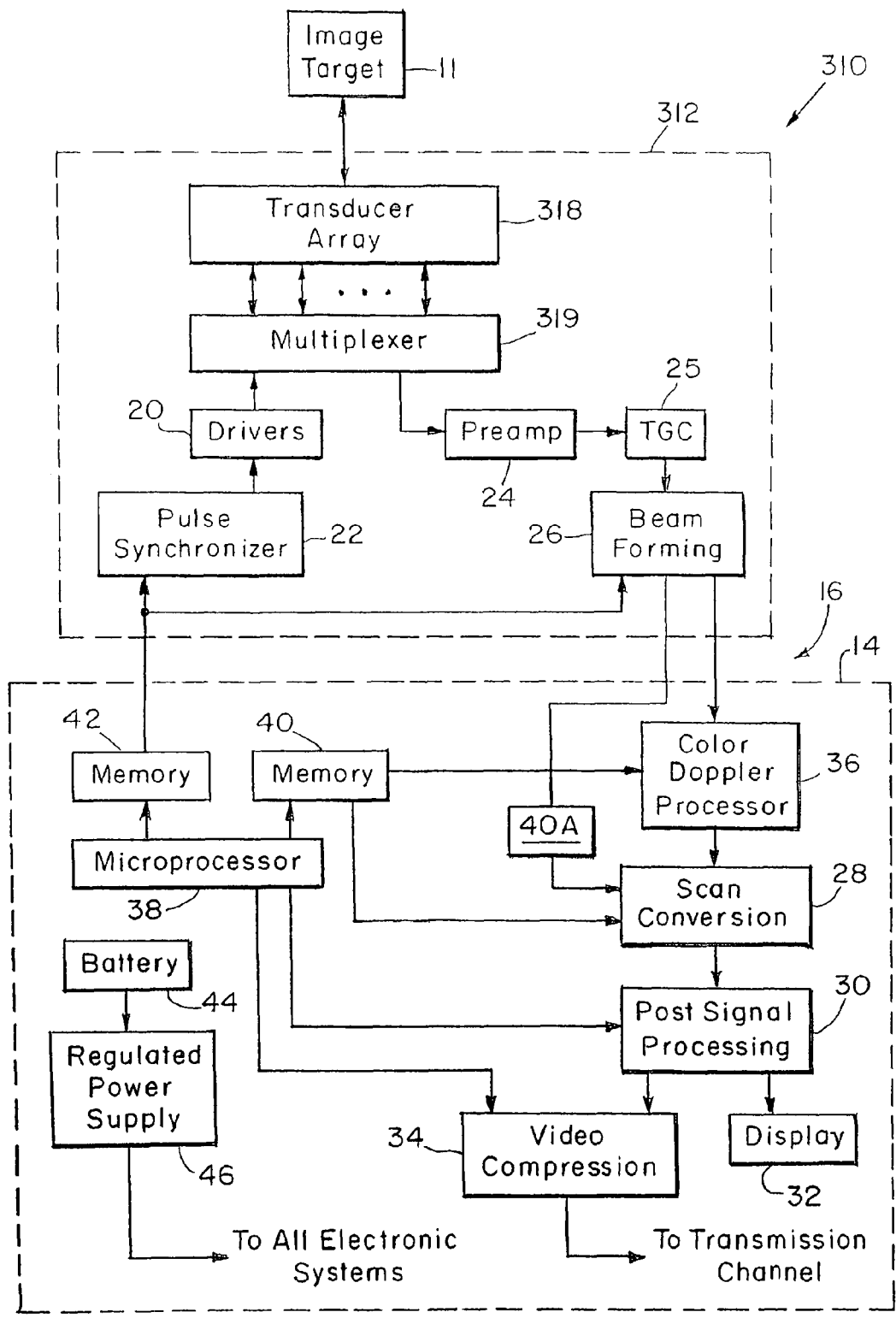
FIG. 27 is a schematic functional block diagram of an alternative preferred embodiment of the ultrasound imaging system of the invention.

FIG. 27 is a schematic functional block diagram of an alternative preferred embodiment of the ultrasound imaging system of the invention. In the embodiment of FIG. 27, a multiplexer 319 is added to the scan head 312 between the ultrasonic transducer array 318 and the drivers 20 and preamplification circuitry 24. In this embodiment, signals are processed from only a portion of the transducer array 318 at any given time. For example, with a 128-element array 318, in one embodiment, only 64 elements will be processed at a time. The multiplexer 319 is used to route the 64 signals to the preamplification 24 and subsequent circuits. The multiplexer 319 is also used to route the driver pulses from the drivers 20 to the 64 elements of the array 318 currently being driven. In this embodiment, referred to herein as the sub-aperture scanning embodiment, circuit complexity is substantially reduced since processing channels need only be provided for the number of elements which are being processed, in this example, 64. Images are formed in this embodiment by scanning across the transducer array 318 and selectively activating groups of adjacent elements to transmit and receive ultrasonic signals.

During sub-aperture scanning, image quality can be degraded by the introduction of image clutter caused by energy in the image obtained through the side lobes rather than the main lobe of the array response. To solve this problem, spatial windowing filters are applied to the array processing to eliminate or reduce the energy from the side lobes. One type of window varies dynamically in width according to the number of active elements. Another window is a non-varying truncated window.

Figure 28:
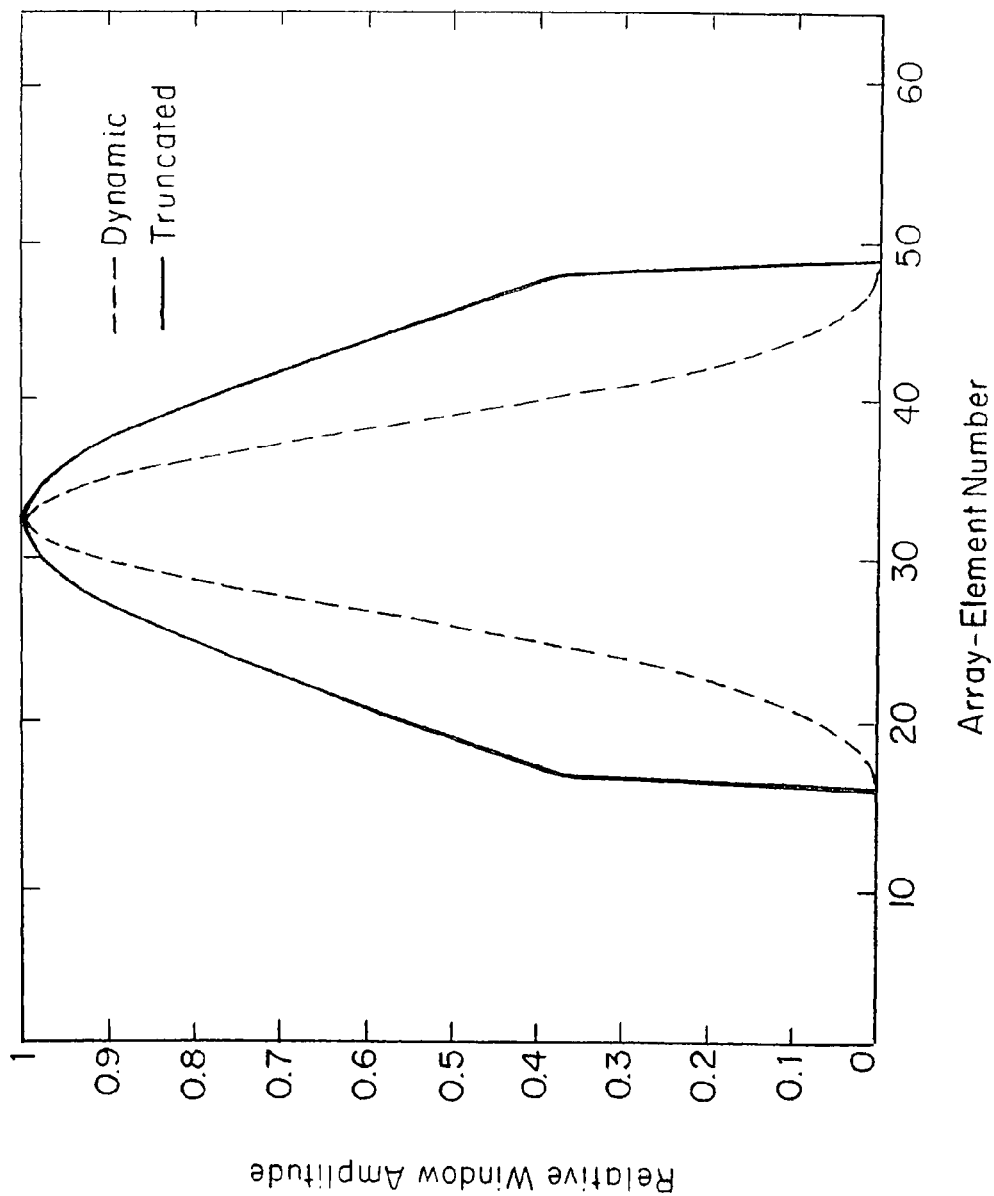
FIG. 28 is a plot comparing truncated non-varying spatial windows and dynamic spatial windows used during sub-aperture scanning in accordance with the present invention.

FIG. 28 is a plot showing the response of both types of windows. In the portable ultrasound system of the invention, the spatial window is designed to match the maximum number of sub-aperture array elements and is not dynamically varied with a change in the number of active elements. The rationale for this implementation is that the reduction in the received (or transmitted) energy using dynamic-spatial windowing produces poorer quality images compared with images obtained using a truncated, non-varying spatial window. For both cases, the reduction in image clutter is nearly equal. Consequently, using a truncated, non-varying spatial window is advantageous because it is simpler to implement and produces better quality images. For the example shown in FIG. 28 (using a 64-element sub-aperture and a Blackman-Harris window), the dynamic window provides less than half the energy (42%) on transmit or receive of the nonvarying, truncated window.

Figure 29A:
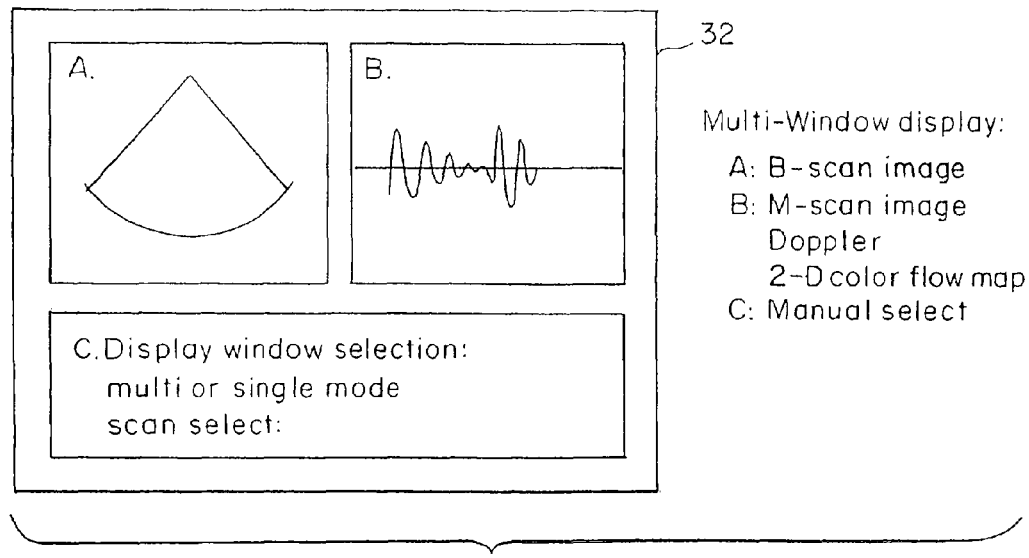
FIGS. 29A and 29B are schematic pictorial views of two user-selectable display presentation formats used in the ultrasound imaging system of the invention.
Figure 29B:
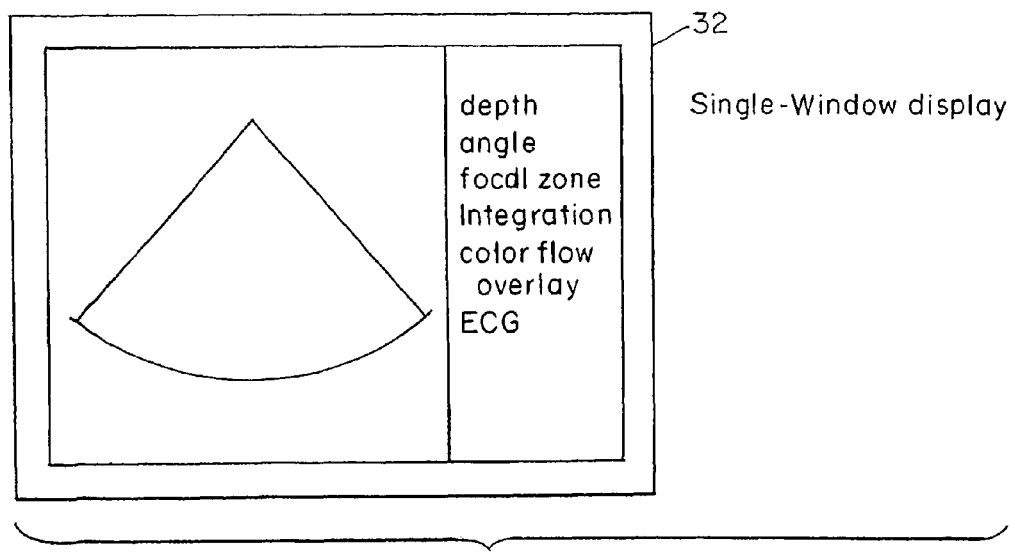

FIGS. 29A and 29B are schematic pictorial views of display formats which can be presented on the display 32 of the invention. Rather than storing a single display format as is done in prior ultrasound imaging systems, the system of the present invention has multiple window display formats which can be selected by the user. FIG. 29A shows a selectable multi-window display in which three information windows are presented simultaneously on the display. Window A shows the standard B-scan image, while window B shows an M-scan image of a Doppler two-dimensional color flow map. Window C is a user information window which communicates command selections to the user and facilitates the user's manual selections. FIG. 29B is a single-window optional display in which the entire display is used to present only a B-scan image. Optionally, the display can show both the B-mode and color doppler scans simultaneously by overlaying the two displays or by showing them side-by-side using a split screen feature.

Figure 30A:
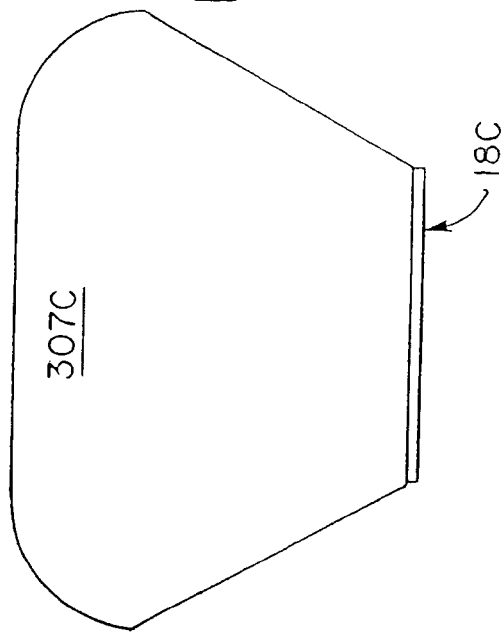
FIG. 30A is a schematic illustration of the relationship between a linear ultrasound transducer array and a rectangular scan region in accordance with the present invention.

FIGS. 30A-30D are schematic diagrams illustrating the relationship between the various transducer array configurations used in the present invention and their corresponding scan image regions. FIG. 30A shows a linear array 18A which produces a rectangular scanning image region 307A. Such an array typically includes 128 transducers. For each scan line, a set of delays is introduced which define the focus points for the image. Because the array is linear and the region is rectangular, the delays for each scan line are typically identical. Hence, in accordance with the present invention, delay values need only be downloaded from the central memory 203 to the local memory and control circuits 206(1)-206(N) once for the entire image. Alternatively, the linear array 18A can be used as a phased array in which different beam steering delay values are introduced for each scan line.

Figure 30B:
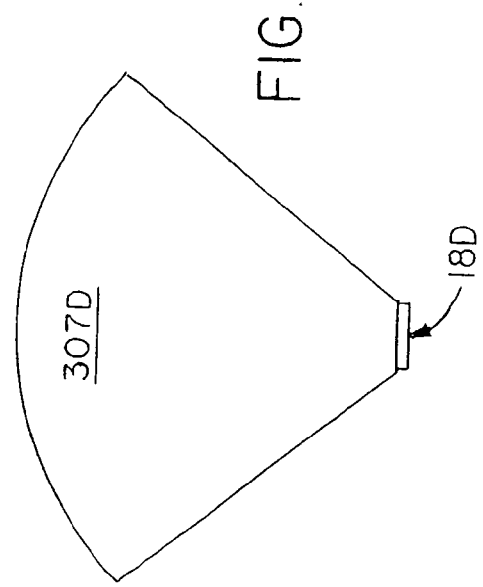
FIG. 30B is a schematic illustration of the relationship between a curved ultrasound transducer array and a curved scan region in accordance with the present invention.

FIG. 30B is a schematic diagram showing the relationship between a curved transducer array 18B and the resulting sectional curved image scan region 307B. Once again, the array 18B typically includes 128 adjacent transducers. Once again, the delays introduced for each scan line can be identical or they can be varied to perform a phased array scanning process.

Figure 30C:
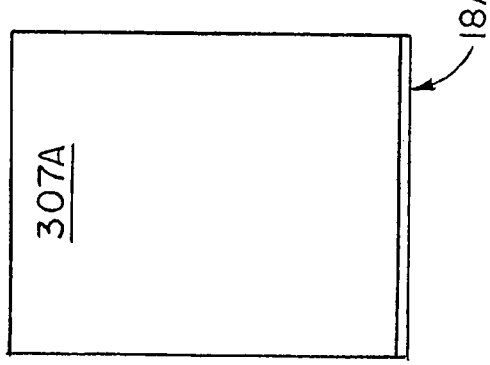
FIG. 30C is a schematic illustration of the relationship between a linear ultrasound transducer array and a trapezoidal scan region in accordance with the present invention.

FIG. 30C shows the relationship between a linear transducer array 18C and a trapezoidal image region 307C. In this embodiment, the array 18C is typically formed from 192 adjacent transducers, instead of 128. The linear array is used to produce the trapezoidal scan region 307C by combining linear scanning as shown in FIG. 30A with phased array scanning. In one embodiment, the 64 transducers on opposite ends of the array 18C are used in a phased array configuration to achieve the curved angular portions of the region 307C at its ends. The middle 64 transducers are used in the linear scanning mode to complete the rectangular portion of the region 307C. Thus, the trapezoidal region 307C is achieved using the sub-aperture scanning approach described above in which only 64 transducers are active at anyone time. In one embodiment, adjacent groups of 64 transducers are activated alternately. That is, first, transducers 164 become active. Next, transducers 64-128 become active. In the next step, transducers 2-65 are activated, and then transducers 65-129 are activated. This pattern continues until transducers 128-192 are activated. Next, the scanning process begins over again at transducers 1-64.

Figure 30D:
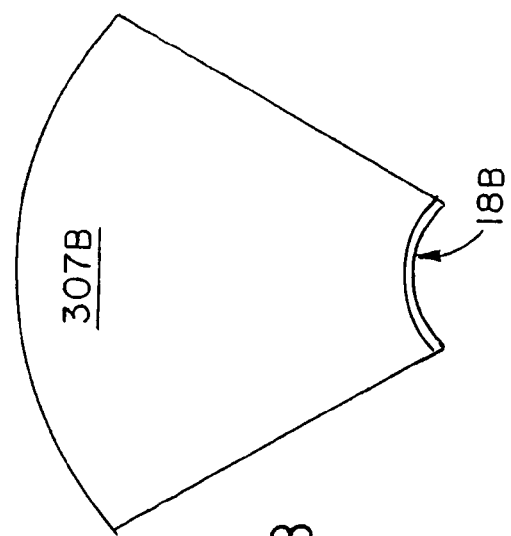
FIG. 30D is a schematic illustration of a phased array scan region.

FIG. 30D shows a short linear array of transducers 18D used to perform phased array imaging in accordance with the invention. The linear array 18D is used via phased array beam steering processing to produce the angular slice region 307D shown in FIG. 30D.

Figure 31:
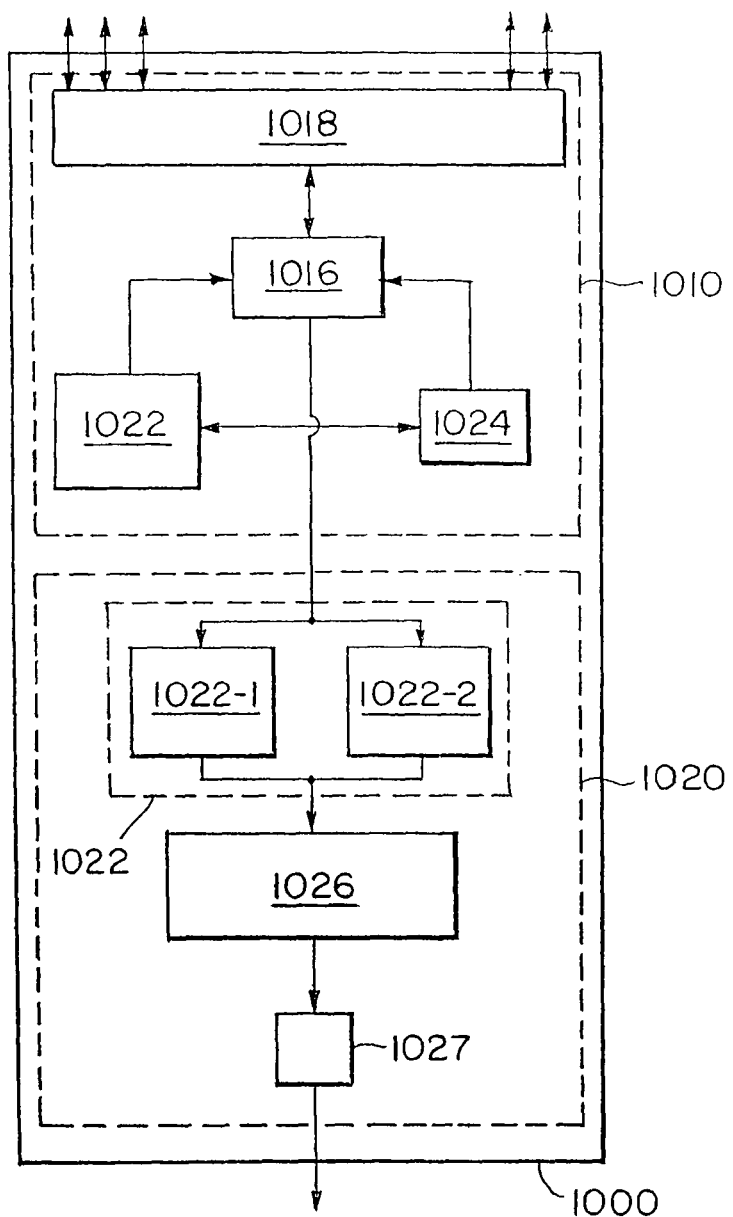
FIG. 31 is a schematic functional block diagram of a circuit board in accordance with the present invention.

FIG. 31 is a schematic functional block diagram of a circuit board in accordance with the invention. The circuit board 1000 is preferably a multi-layer circuit board about two-by-four inches in dimension. It is preferably double sided and is populated using surface-mount technology. The circuitry can functionally be divided into a transmission circuit 1010 and receiver circuit 1020. The transmission circuit 1010 includes a pulse synchronizer circuit 1022 coupled to a high voltage driver/pulser circuit 1024. The driver/pulser 1024 is connected through a transmit/receive (T/R) switch 1016 to a multiplexer module 1018.

The pulser 1024 generates a series of high voltage pulses under the control of the delay processing circuitry of the pulse synchronizer circuit 1022. The pulses are transferred to the array of transducers 18 via the T/R switch 1016 and multiplexer 1018 to generate the ultrasonic signals. The T/R switch 1016 operates to ensure that the high voltage pulses of the pulser 1024 do not reach the sensitive receive circuitry 1020. It provides, via a diode protection structure, overvoltage protection to the pre-amp TGC circuits in the receive circuit 1020. The T/R switch 1016 includes isolation electronics used during sub-aperture scanning to isolate unused transducer elements from used elements. The circuitry also prevents crosstalk between processing channels caused by spurious signals.

The receiver circuit 1020 includes a pre-amp and TGC circuit module 1022, a beam former module 1026 and an optional analog-to-digital converter 1027. As illustrated, the pre-amp and TGC 1022 is represented by two chips 1022-1, 1022-2. Each of the pre-amp and TGC chips process half of the channels used at a given time. The number of actual chips representing the pre-amp and TGC circuit 1022 is driven by the fabrication process. Preferably, the pre-amp and TGC circuit 1022 is fabricated as a single chip.

The beam forming module 1026 can include the beam forming circuitry described above in connection with any of the embodiments. The module 1026 preferably is formed on a single chip and contains all the circuitry necessary to perform the beam forming functions described above.

The transmission circuit 1010 and the low voltage receiving circuit 1020 can each be fabricated as a single chip. By reducing the chip count in the circuit, the size of the circuit board 1000 can be reduced. The circuit board 1000 also contains surface mount discrete components, such as resistors, capacitors, inductors, etc., or their integrated equivalents.

Figure 32:
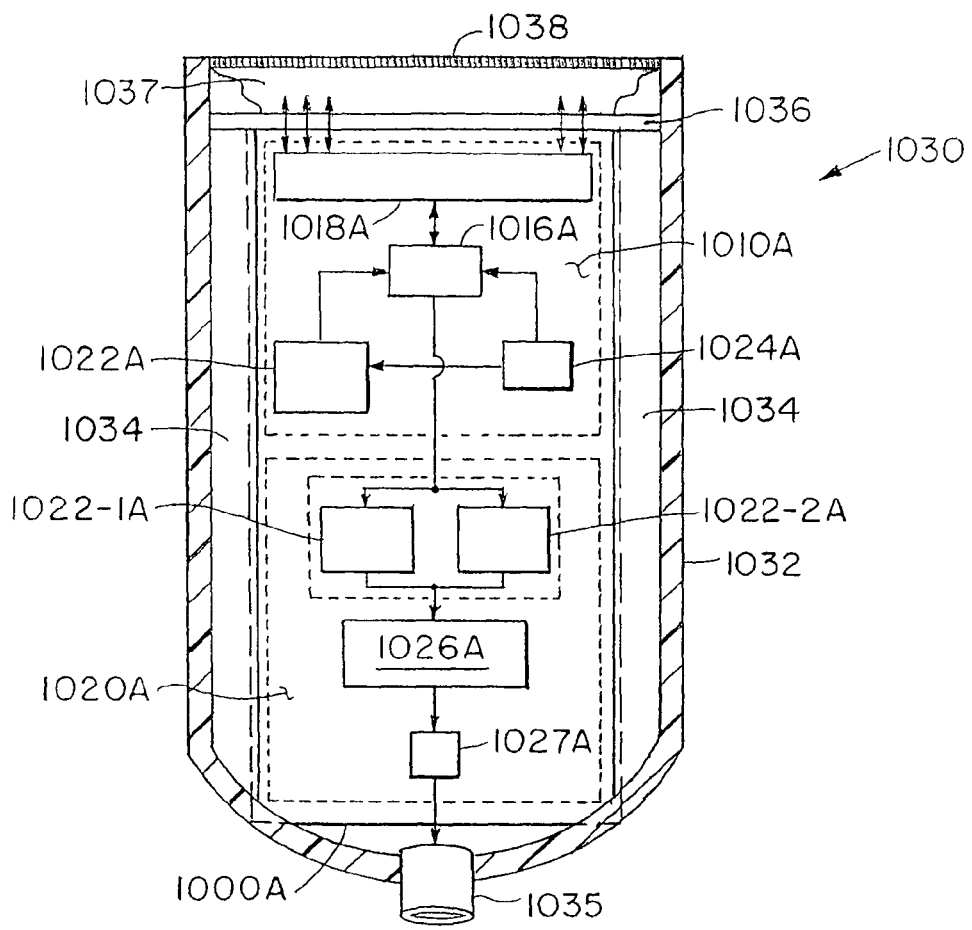
FIG. 32 is a schematic partial cross-sectional diagram of one embodiment of a linear scan head in accordance with the present invention.

FIG. 32 is a cross-sectional schematic diagram of one embodiment of a linear scan head shown partially in cross section. The scan head 1030 is enclosed by a plastic housing 1032. As illustrated, a circuit board 1000A is held in place within the housing 1032 by supporting members 1034. The circuit board 1000A connects to a bus connector 1036, which is connected by a flexible ribbon cable or printed flex cable 1037 to a linear array of transducers 1038. A coax cable connector 1035 couples the scan head 1030 to external electronics. Alternatively, a connector for twisted pair conductors can be used.

Figure 33:
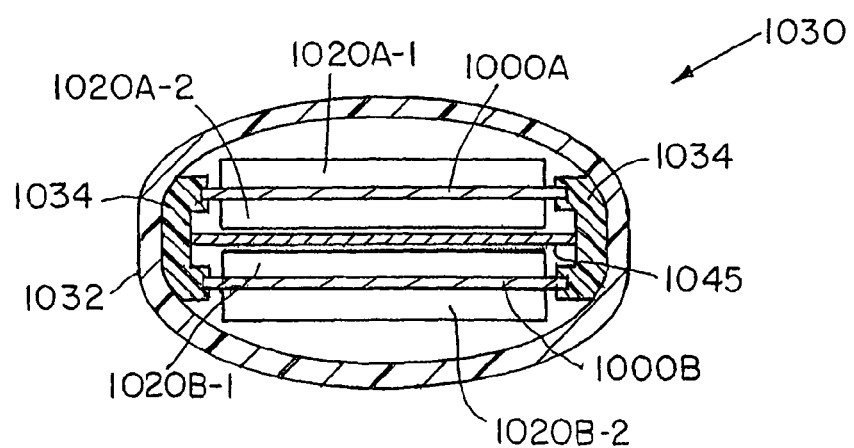
FIG. 33 is a schematic side cross-sectional view of the scan head of FIG. 31.

FIG. 33 is another cross-sectional view of the scan head 1030 of FIG. 32. As illustrated, the supporting members 1034 hold two double sided circuit boards 1000A, 1000B. Two or more boards can be single or double sided, and stacked side-by-side or offset to maximize use of the available space, depending upon the specific application. The circuit boards are separated by a heat conducting layer 1045 which acts as a heat sink for the circuitry. A heat conductor filler can also be inserted within the housing The supporting members 1034 are preferably fabricated from a low friction material such as teflon to facilitate the insertion and removal of the circuit boards 1000A, 1000B. Each side of the circuit boards can preferably process 64 channels of information from the transducers 1038. Therefore, as illustrated, two double sided circuit boards 1000A, 1000B can support 256 transducers.

Figure 34:
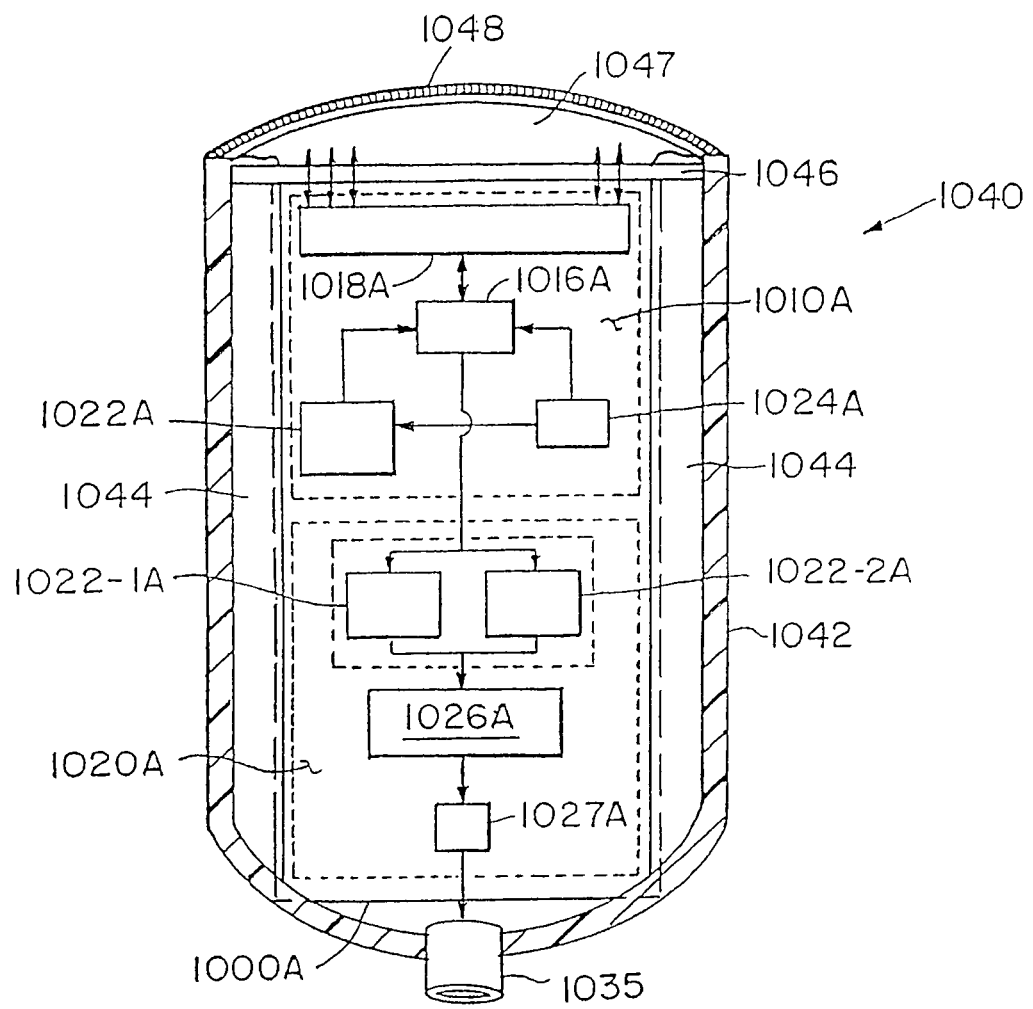
FIG. 34 is a schematic partial cross-sectional view of a scan head using a curve transducer array in accordance with the present invention.

FIG. 34 is a preferred embodiment of a curved transducer scan head shown partially in cross section. The scan head 1040 is formed by a plastic housing 1042. Note that the handle section can have an external ribbing to provide a better gripping surface and optionally can be used to vent heat from the housing. A circuit board 1000A is held in place by teflon support members 1044. The circuit board 1000A is connected to a coax connector 1035 (or a twisted pair connector) and a bus connector 1046. The bus connector 1046 is connected to a curved array of transducers 1048 by a printed flex cable 1047.

Figure 35:
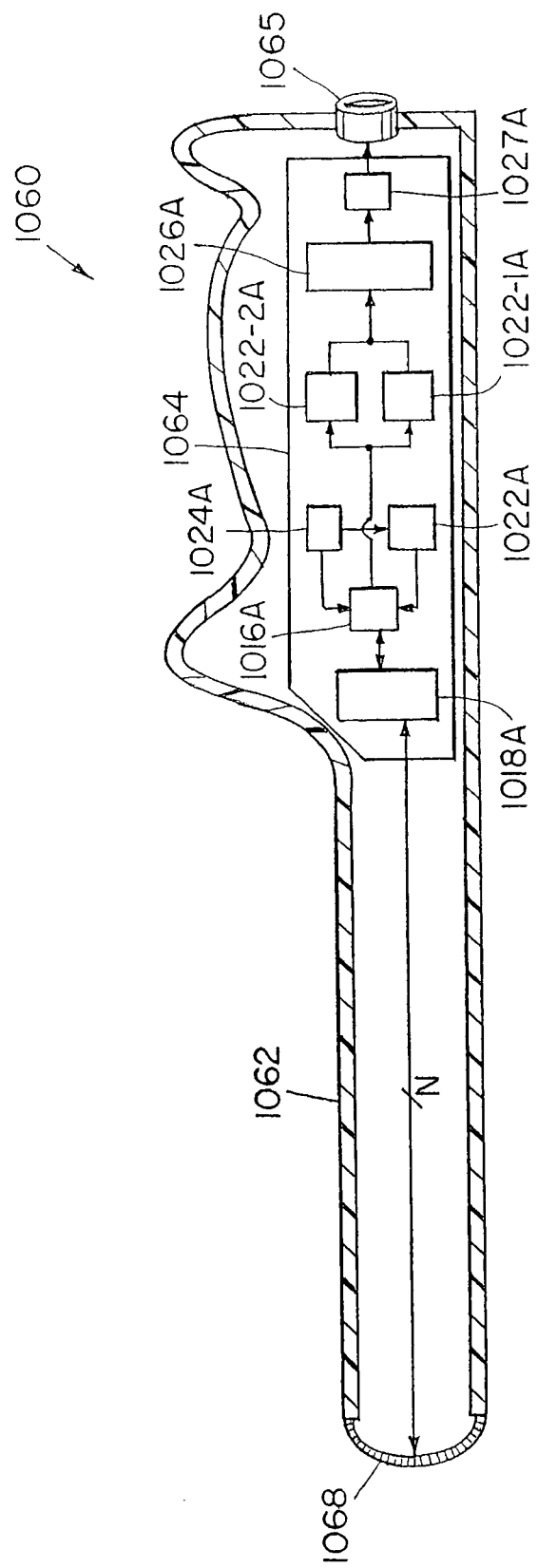
FIG. 35 is a schematic cross-sectional diagram of an internal ultrasonic probe in accordance with the present invention.

FIG. 35 is a schematic diagram of an insertable ultrasonic probe shown partially in cross section. The probe 1060 is defined by a plastic housing 1062 divided into an elongate probe for insertion into a lumen or body cavity and a handle section to be gripped by an operator. A circuit board 1064 is secured within the handle of the probe 1060 and is connected to a coax connector 1065 and to an array of transducers 1068. Except for being smaller in size to fit with the handle, the circuit board 1064 is functionally identical to the circuit board 1000 of FIG. 30. Preferably there are 128 transducers (N=128) in the array 1068. In that case, a double-sided circuit board 1064 having 64 channels of processing on each side is sufficient to operate the probe.

Figure 36:
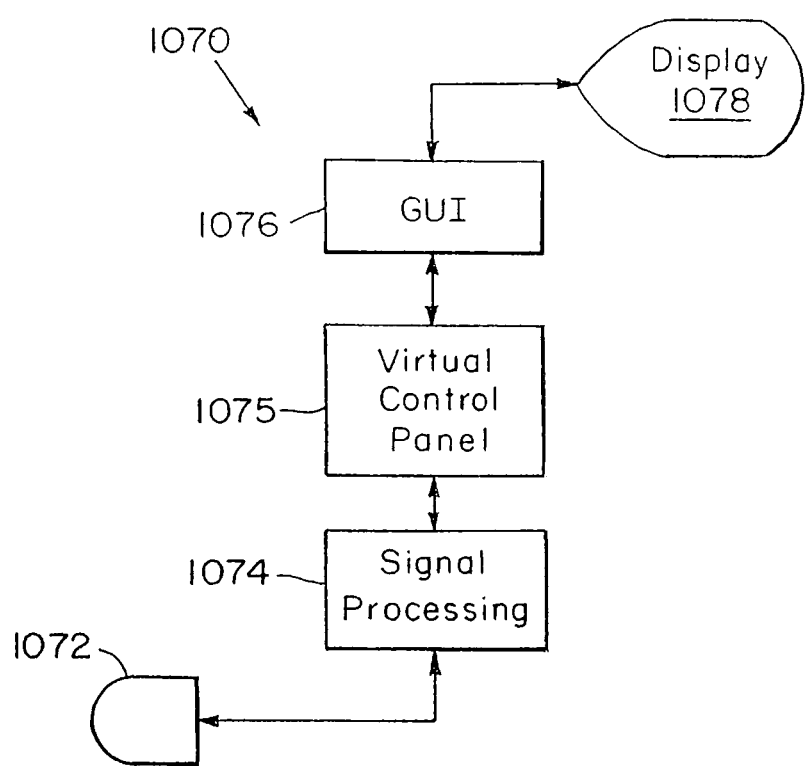
FIG. 36 is a top-level flow diagram illustrating the logical flow of the software used to control the operation of the present invention.

FIG. 36 is a block diagram of the software required to operate the ultrasonic devices described herein. Illustrated is ultrasonic scanner 1072 and a user display 1078. A signal processing module 1074 provides hardware specific control such as control of digital signal processors, custom chips and system timing. The user display 1078 is driven by a graphical user interface (Gill) 1076, such as those compatible with windows operating systems. A virtual control panel 1075 provides an interface between the graphical user interface 1076 and the hardware interface 1074.

A typical display provides the user with the capability to freeze a frame of data, print a frame of data, or archive a frame of data to a disk. The user can also highlight a region for color doppler imaging and audio doppler processing. The user can also manually vary the received data as a function of depth. Preferably, there are eight depth zones. The user can also vary the number of transmission focal zones (from 1-8 zones), vary the image contract and the image brightness.

More specifically, the user can select an imaging mode. A B-mode is provided to adjust brightness or conventional image display. A C-mode is provided to control color doppler flow either as an overlay or as a side-by-side image. An M-mode is provided to control time-varying doppler images in an independent image mode. An audio doppler mode can be set to either on or off to supplement the B-mode and C-mode displays.

The user can also set up the transducer array to determine image display size and shape. Selections are based on whether the transducer array is a curved-linear, linear or phased array.

The user can also enter and display patient information. The patient data is then is then used to label the displays. The computer used to provide display of the images can be programmed with a software module to display patient management and imaging data in a Windows format. The user is presented with a variety of pull down menus operated with a mouse.

The user can also set up the imaging mode based on the particular application of the scanner. The user can adjust the image depth and transmission power automatically based on whether the imaging is for cardiac, radiologic, obstetric, gynecological, or for peripheral vascular applications. The user can also set the image depth and transmission manually for custom applications.

Figure 37:
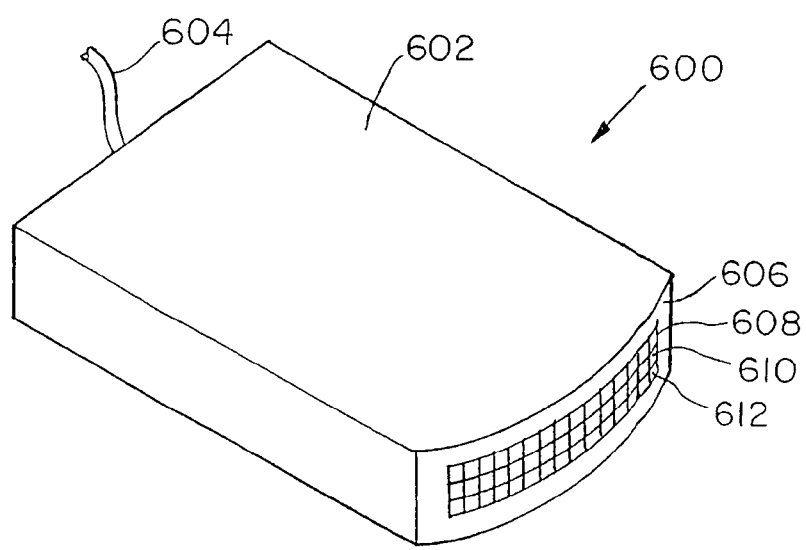
FIG. 37 is a perspective view of a two dimensional transducer array in accordance with the invention.

Another preferred embodiment of the invention relates to an ultrasound imaging device having two or more adjacent rows of transducers to form a two dimensional transducer array. As illustrated in the hand-held device 600 of FIG. 37, the transducer section 606 of the housing 600 contains three rows 608, 610 and 612 of transducers. The rows 608, 610 and 612 can be of different lengths. For example, rows 608 and 612 can be shorter than the middle row 610 (e.g. the middle row can be 1.5 times the length of the shorter row). The spacing between adjacent rows can also be the same or greater than the spacing between transducers within any given row. The coarser inter-row spacing can provide effective focusing of the ultrasound signal emitted by the transducer array. As described in connection with previous embodiments each row of transducers can be connected to the chip carrier or circuit board in the housing one or more flex cables.

Figure 38:
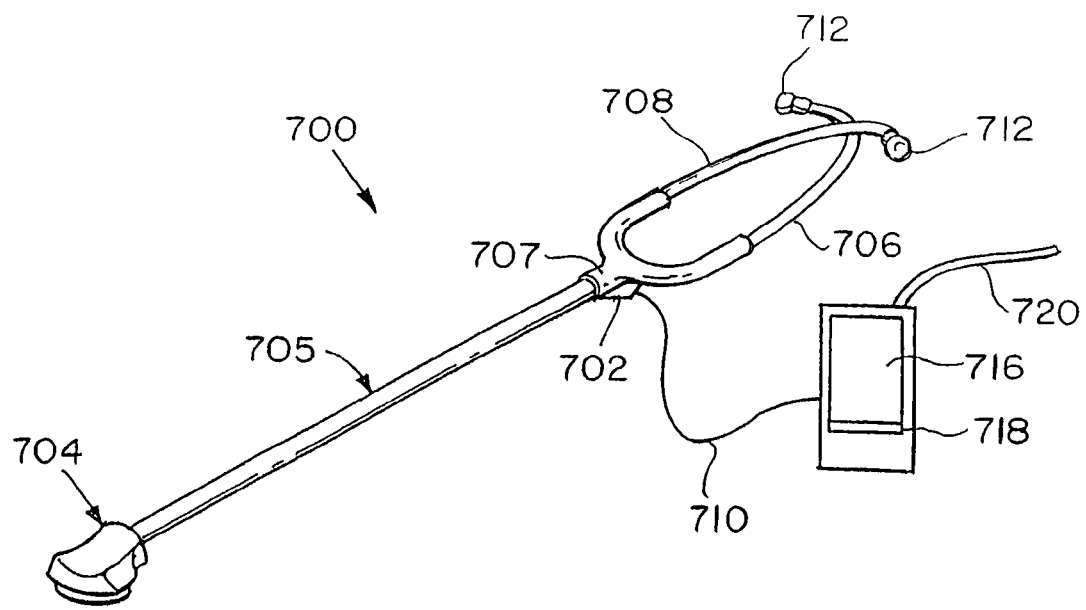
FIG. 38 is a schematic illustration of an electronic ultrasound stethoscope in accordance with the invention.

Another preferred embodiment of the invention relates to a portable ultrasound stethoscope system 700 illustrated in FIG. 38. This system incorporates a transducer array, synchronizing and driver circuitry for the array and beam forming circuitry in the acoustic sensor housing 704, or chestpiece, of the stethoscope.

The sensor housing 704 of the stethoscope is connected to two earpieces 712 to provide audio information to the user. A central tube 705 connects housing 704 to Y-connector 707. The earpieces 712 are mounted on tubes 706, 708 that extend from Y-connector 707. A connector housing 702 connects the stethoscope to the cable 710. The connector housing 702 can be integrally formed or attached to Y-connector 707 or it can be attached to housing 704. A transducer mounted in the V-connector 707 can be used to generate audio that is delivered along tubes 706, 708 to earpieces 712. The stethoscope can be used to provide standard acoustic information, electronic audio information, and/or ultrasound information.

The beam forming circuitry in the sensor housing 704 of the stethoscope generates a spatial representation of a region of interest that is delivered along cable 710 to a hand-held display device 714 such as a personal digital assistant. The display housing 714 contains a processor for generating ultrasound images as described previously herein, preferably an M-mode display or a Doppler display. The user can generate simultaneous audio and image data of the region of interest which can be stored in memory or transferred by modem along cable 720 to a separate system.

Power can be provided by a battery within the display housing 714, within the sensor housing 704, or within the connector housing 702. The housing 714 can include a flat panel display 716 such as a liquid crystal display and a user interface 718 such as a keypad or mouse control.

Another preferred embodiment of the invention is the ultrasound system 800 illustrated in connection with FIGS. 39A and 39B. In this embodiment a transducer element or array 802 is secured to a patient's skin 810 with a patch 805. The patch 805 can have an adhesive border 806 to secure the patch 805 to the skin of the patient. The array 802 is connected by cable 808 or wireless connection to a body worn housing 804 which can record and/or transmit the data to another receiver location. The patch can have a single transducer element, or a single or multilinear array as described previously, or can have an annular array 812 as depicted in the patch 814 of FIG. 39B. The patch can include beam forming and focusing circuitry as described previously in the present application. Power to the transducer system and associated circuitry can be provided using a battery that can be located within housing 804.

Another preferred embodiment of the invention relates to a flexible ultrasound probe or catheter system for insertion into body lumens or cavities. Such a system 900 is illustrated in connection with FIGS. 40A and 40B. System 900 includes a flexible shaft 902 having a proximal end 905 connected to housing 904 and a distal end 907. Processing circuitry as described previously is located within housing 904. Housing 904 is connected to a user interface 906 and a display 908 with cable 910. The distal end 907 of the probe shaft includes a distal section 912 in which the transducer array 918 and a chip carrier or circuit board assembly 916 are located. The chip carrier 916 is connected to a cable 920 that delivers control signals to the pulse synchronizer, driver circuits, and beam forming and focusing circuits as described previously in the application and delivers the summed electrical representation of the region of interest to the processing circuitry in the housing 904. The outer wall 922 of the shaft is sealed to isolate internal components from the working environment.

The transducer array can be radially directed, or alternatively, can be distally directed along the catheter axis. A lumen 914 can be optionally included to provide for use with a fiber optic viewing system, a guidewire, or other treatment or surgical instruments.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An ultrasound imaging system comprising:
a hand-held probe housing having a transducer array circuit including a transducer array that detects ultrasound signals;
a beam transmission integrated circuit that controls transmission of ultrasound signals by the transducer array;
a sampling circuit that samples detected ultrasound signals to generate sampled ultrasound signals;
a beamformer integrated circuit that delays the sampled ultrasound signals and generates delayed, sampled ultrasound signals;
a summing circuit that generates an electronic representation of the region of interest with the delayed, sampled ultrasound signals;
a hand-held data processor housing having a memory, a battery and a data processor, the data processor generating Doppler ultrasound images from the electronic representation of the region of interest with a graphical user interface (GUI);
a cable electronically connecting the hand-held probe housing to the hand-held data processor housing; and
a display on the hand-held data processor housing for displaying ultrasound images with the graphical-user interface, the ultrasound images being transferred to the display using the data processor.

2. The system of claim 1 wherein the hand-held probe housing comprises at least one of a linear array probe, a curved array probe, and a phased array probe.

3. The system of claim 1 further comprising a second cable connecting an interface circuit and the probe housing.

4. The system of claim 1 wherein the beamformer circuit further comprises a charge coupled device (CCD) beamformer circuit.

5. The method of claim 1 further comprising an analog to digital converter such that digital data is directed to the data processor.

6. The system of claim 1 wherein the data processor further comprises a personal computer.

7. The system of claim 1 wherein the hand-held data processor housing further comprises a laptop computer.

8. The system of claim 1 wherein the data processor further comprises a Doppler processor.

9. The system of claim 1 further comprising a filter that filters the electronic representation.

10. The system of claim 1 further comprising a demodulator that demodulates the ultrasound signals.

11. The system of claim 1 further comprising a beamformer control circuit in the data processor housing that sends beamformer control signals to the beamformer integrated circuit that is positioned in the probe housing.

12. The system of claim 1 wherein the beamformer circuit further comprises a plurality of programmable tapped delay lines.

13. The system of claim 1 wherein the battery provides power to the data processor.

14. The system of claim 1 further comprising a scan conversion circuit that converts the electronic representation from polar coordinates to rectangular coordinates.

15. The system of claim 1 wherein the data processor housing further comprises a keyboard and the display comprises a flat panel display.

16. The system of claim 1 wherein the display is integral with the data processor housing and the beamformer integrated circuit is positioned in the probe housing.

17. The system of claim 1 further comprising a second display that is located at a site remote from the data processor.

18. The system of claim 1 wherein the graphical user interface is adapted to process a plurality of images of the region of interest for display such that a user can select one of the images for display on the display.

19. The system of claims 18 further comprising a second memory that stores the selected image.

20. The system of claim 18 wherein the plurality of images further comprises images of moving objects processed using a Doppler processor.

21. The system of claim 1 wherein the electronic representation of the region of interest further comprises digital signal data.

22. The system of claim 1 further comprising a video compression device in communication with the data processor.

23. An ultrasound imaging system comprising:
   a hand-held probe housing having a transducer array, the transducer array receiving signals from a region of interest and that generates an input signal;
   a beam transmission integrated circuit that controls transmission of ultrasound signals by the transducer array;
   a sampling circuit that samples the input signal to generate sampled ultrasound signals;
   a beamformer integrated circuit that delays the sampled ultrasound signals to generate delayed, sampled ultrasound signals;
   a summing circuit that generates an electronic representation of the region of interest with the delayed, sampled ultrasound signals; and
   a cable that connects the hand-held probe housing to a hand-held computer, the hand-held computer having a memory, a battery, a data processor, and a liquid crystal display such that the electronic representation is processed with the data processor to generate ultrasound images using a graphical user interface, the ultrasound images being displayed on the display.

24. The system of claim 23 wherein the hand-held probe housing comprises at least one of a linear array probe, a curved array probe, and a phased array probe.

25. The system of claim 23 further comprising a second cable that connects an interface unit and the probe housing.

26. The system of claim 23 wherein the beamformer integrated circuit further comprises a charge coupled device (CCD) beamformer circuit.

27. The system of claim 23 wherein the computer is adapted to execute a scan conversion program.

28. The system of claim 23 wherein the computer comprises a laptop computer.

29. The system of claim 23 wherein the data processor further comprises a Doppler processor.

30. The system of claim 23 further comprising a filter in the hand-held computer that filters the delayed signals.

31. The system of claim 23 further comprising a demodulator that demodulates the delayed signals.

32. The system of claim 23 further comprising a beamformer control circuit that transmits signals from the computer to the beamformer integrated circuit that is positioned in the probe housing.

33. The system of claim 23 wherein the transducer array comprises a plurality of rows, each row comprising a linear array.

34. The system of claim 23 wherein the transducer array comprises a plurality of parallel rows such that one of the rows is longer than another row.

35. The system of claim 23 further comprising a virtual control panel.

36. The system of claim 35 wherein the virtual control panel further comprises a plurality of images of the region of interest for display and a display selection window.

37. The system of claim 36 further comprising a control signal memory.

38. The system of claim 36 wherein the plurality of images further comprises images of moving objects processed using a Doppler processor.

39. The system of claim 23 further comprising a disk data storage system such that images can be stored on a disk.

40. The system of claim 23 wherein the display comprises a flat panel display.

41. The system of claim 23 wherein the probe housing, cable and computer have a weight not exceeding ten pounds.

42. The system of claim 23 wherein the computer further comprises a doppler processor.

43. The system of claim 23 further comprising a modem for remote transmission of image data.

44. The system of claim 23 wherein the battery provides power to the computer and the probe housing.

45. The system of claim 23 wherein the display is integral with the computer.

46. The system of claim 23 wherein the virtual control panel is operable to select from a plurality of scan windows.

47. The system of claim 23 further comprising a video compression device in communication with the data processor.

* * * * *